US008337941B2

(12) United States Patent
Gubernator et al.

(10) Patent No.: US 8,337,941 B2
(45) Date of Patent: Dec. 25, 2012

(54) FLUORESCENT SUBSTRATES FOR MONOAMINE TRANSPORTERS AS OPTICAL FALSE NEUROTRANSMITTERS

(75) Inventors: Niko Gert Gubernator, New York, NY (US); Dalibor Sames, New York, NY (US); David Sulzer, New York, NY (US); Paul Vadola, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 500 days.

(21) Appl. No.: 12/309,724

(22) PCT Filed: Jul. 27, 2007

(86) PCT No.: PCT/US2007/017014
§ 371 (c)(1),
(2), (4) Date: Jan. 27, 2009

(87) PCT Pub. No.: WO2008/013997
PCT Pub. Date: Jan. 31, 2008

(65) Prior Publication Data
US 2010/0035279 A1    Feb. 11, 2010

Related U.S. Application Data

(60) Provisional application No. 60/834,356, filed on Jul. 27, 2006.

(51) Int. Cl.
*C07D 405/04* (2006.01)
*C07D 311/02* (2006.01)
*B05D 5/12* (2006.01)

(52) U.S. Cl. ........ 427/66; 428/917; 546/268.1; 549/284

(58) Field of Classification Search ............... 546/268.1; 549/284; 428/917
See application file for complete search history.

(56) References Cited

U.S. PATENT DOCUMENTS

| 3,899,529 | A | 8/1975 | Witzel et al. |
| 5,989,535 | A | 11/1999 | Nayak |
| 2004/0058983 | A1* | 3/2004 | Vuorela et al. ............ 514/456 |
| 2005/0170442 | A1 | 8/2005 | Kupcho et al. |
| 2008/0194522 | A1 | 8/2008 | Chen et al. |
| 2009/0005436 | A1 | 1/2009 | Carotti et al. |
| 2009/0267026 | A1 | 10/2009 | Goto et al. |
| 2010/0048604 | A1 | 2/2010 | Yee et al. |

FOREIGN PATENT DOCUMENTS

| JP | 02-043521 | 2/1990 |
| JP | 05-263072 | 10/1993 |
| WO | WO/2011/094560 A1 | 8/2011 |

OTHER PUBLICATIONS

International Search Report issued by the International Searching Authority (ISA/US) on Sep. 19, 2008 in connection with International Application No. PCT/US2007/017014.
Written Opinion of the International Searching Authority issued by the International Searching Authority (ISA/US) on Sep. 19, 2008 in connection with International Application No. PCT/US2007/017014.
PCT International Publication No. WO/2006/026368, published on Mar. 9, 2006.
International Search Report in connection with PCT/US05/30276 issued Jun. 20, 2006.
International Preliminary Report on Patentability in connection with PCT/US2005/30276 issued Feb. 28, 2007.
Written Opinion issued Jun. 20, 2006 in connection with PCT/US05/30276.
PCT International Publication No. WO/2006/023821, published on Mar. 2, 2006.
PCT International Publication No. WO/2007/022263 A1, published on Feb. 22, 2007.
International Search Report in connection with PCT/US2006/031979 issued Jan. 8, 2007.
International Preliminary Report on Patentability in connection with PCT/US2006/031979 issued Feb. 20, 2008.
Written Opinion issued Jan. 8, 2007 in connection with PCT/US2006/031979.
International Search Report in connection with PCT/US05/29722 issued Jul. 25, 2008.
Written Opinion issued Jul. 25, 2008 in connection with PCT/US05/29722.

(Continued)

*Primary Examiner* — Susannah Chung
(74) *Attorney, Agent, or Firm* — John P. White; Cooper & Dunham LLP

(57) ABSTRACT

The present invention relates to compounds of the general structure: wherein Y is O, X is O, bond α is absent and bond β is present, or Y is H, X is CH, bond α is present, and bond β is absent; atom Z is a carbon and bonds χ, δ and γ are present, or is a nitrogen and bonds χ, δ and γ are absent; $R_1$ is —H, —OH, —O—$R_7$, —N(H)—$R_8$, —N(H)—$(CH_2)_n$—$NH_2$, —N($R_9$)($R_{10}$), or a piperazine cation; $R_2$ is either covalently bound to $R_9$, or is —H, or is covalently bound to $R_3$ so as to form a substituted or unsubstituted pyrrole or $R_2$ is covalently bound to $R_9$ or $R_8$ or $R_7$; or $R_1$ and $R_2$ are covalently joined to form an aromatic ring; $R_3$ is either covalently bound to $R_2$ so as to form a pyrrole, or is, inter alia, —H, —OH, alkyl, or when Z is nitrogen $R_3$ is =O; $R_4$ is, inter alia, —H, —OH, or —$R_{11}NH_2$; $R_5$ is, inter alia, —H, —OH, or —$R_{12}NH_2$, and $R_6$ is either is covalently bound to $R_{10}$ or is —H, or $R_6$ is covalently bound to $R_{10}$ or $R_8$ or $R_7$. This invention also provides processes for making the compounds as well as methods for monitoring activity of monoamine transporters or treating monoamine transporter-associated diseases by employing the compounds.

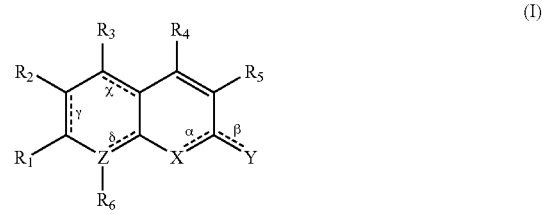

(I)

8 Claims, 39 Drawing Sheets

OTHER PUBLICATIONS

Notification of Transmittal of the International Search Report and the Written Opinion of the International Searching Authority, of the Declaration in connection with PCT/US05/29722 issued Jul. 25, 2008.

CAS Online, Document No. 48:14743, Reg. No. 14415-44-2 (1954).

CAS Online, Document No. 115:182261, Reg. No. 136449-44-0 (1991).

CAS Online, Document No. 118:52524, Reg. No. 14415-44-2 (1993).

CAS Online, Document No. 69:93083 (1968).

Zhou, X. Synthesis and NKT Cell Stimulating Properties of Fluorophore- and Biotin-Appended 6"-amino-6"deoxy-galactosylceramides. Org. Lett. Mar. 2002, vol. 4, No. 8, pp. 1267-1270.

Nitz, M. Enantioselective synthesis and application of the highly fluorescent and environment-sensitive amino acid 6-(2-diemthylaminonaphthoyl)alanine (DANA). Science. Jul. 2002, vol. 296 (5573), pp. 1700-1703.

Yee, D.J. et al. "New tools for molecular imaging of redox metabolism: Development of a fluorogenic probe fpr 3-alpha-hydroxysteroid dehydrogenases." J. Am. Chem. Soc. (2004), vol. 126, pp. 2282-2283.

Prabhakar Rao B.V.V.S.N. et al "Theoretical study on naphthyl-phenylacetylenes for second-order nonlinear optical applications." Can. J. Chem. (1997), vol. 75, pp. 1041-1046.

PCT International Publication No. WO/2008/013997 A2, published on Jan. 1, 2008.

Notification Concerning Transmittal of International Preliminary Report on Patentablity in connection with PCT/US2007/017014 issued Feb. 5, 2009.

Notification Concerning Transmittal of International Preliminary Report on Patentablity in connection with PCT/US2005/029722 issued Mar. 5, 2009.

Notification of Transmittal of the International Search Report and the Written Opinion of the International Searching Authority, or Declaration issued on May 4, 2011 in connection with International Application PCT/US2011/022951.

Partilla et al. "Interaction of Amphetamines and Related Compounds at the Vesicular Monoamine Transporter." Journal of Pharmacology and Experimental Therapeutics 2006, vol. 319, No. 1, 237-256.

Lee et al. "Development of pH-Responsive Fluorescent False Neurotransmitters." J. Am. Chem. Soc. 2010, vol. 132, 8828-8830.

Edenharder et al. "Inhibition of the Mutagenicity of 2-Nitrofluorene, 3-Nitrofluoranthene and 1-Nitropyrene by Flavonoids, Coumarins, Quinones and Other Phenolic Compounds" Food and Chemical Toxicology 1997, vol. 35, 357-372.

Office Action issued Apr. 5, 2011 in connection with U.S. Appl. No. 11/661,152.

Chen et al. "Design of Optical Switches as Metabolic Indicators: Fluorogenic Probes for Monoamine Oxidases (MAO A and MAO B)" J. Am. Chem. Soc. 2005, vol. 127, 4544-4545.

Final Office Action issued Oct. 18, 2011 in connection with U.S. Appl. No. 11/661,152.

Raj et. al. "Mechanism of Biochemical Action of Substituted 4-Methylbenzopyran-2-ones. Part I: Dioxygenated 4-Methyl Coumarins as Superb Antioxidant and Radical Scavenging Agents" Bioorganic & Medicinal Chemistry 1998, vol. 6, p. 833-839.

* cited by examiner

| | ε (M₋₁cm₋₁) | λ_max (nm) | λ_em (nm) |
|---|---|---|---|
| | 1465 +/- 49 | 317, 330 | 356 |

50  Measured in pH 7.4 PBS Buffer

| | ε (M₋₁cm₋₁) | λ_max (nm) | λ_em (nm) |
|---|---|---|---|
| 55 | 818 +/- 11 | 319, 330 | 424 |

Measured in pH 7.4 PBS Buffer

511

500 nM, 10 ms

Measured in pH 7.4 PBS Buffer

| ε (M₋₁cm₋₁) | λ$_{max}$ (nm) | λ$_{em}$ (nm) |
|---|---|---|
| 14442 +/- 243 | 343 | 446 |

Measured in pH 7.4 PBS Buffer

| ε (M₋₁cm₋₁) | λ_max (nm) | λ_em (nm) |
|---|---|---|
| 7081 +/- 709 | 357 | 507 |

Measured in pH 7.4 PBS Buffer

112

$\epsilon$ (M$_{-1}$cm$_{-1}$)   $\lambda_{max}$ (nm)   $\lambda_{em}$ (nm)
34027 +/- 1002   493   530

Acridine Orange

| ε (M$_{-1}$cm$_{-1}$) | λ$_{max}$ (nm) | λ$_{em}$ (nm) |
|---|---|---|
| 2987 +/- 217 | 388, 407 | 419, 445 |

Measured in pH 7.4 PBS Buffer

112
$\lambda_{ex} = 357$ nm
$\lambda_{em} = 507$ nm

511
$\lambda_{ex} = 407$ nm
$\lambda_{em} = 502$ nm

Acridine Orange
$\lambda_{ex} = 493$ nm
$\lambda_{em} = 530$ nm

511

| ε (M₋₁cm₋₁) | λ$_{max}$ (nm) | λ$_{em}$ (nm) |
| --- | --- | --- |
| 14528 +/- 684 | 407 | 502 |

Measured in pH 7.4 PBS Buffer

A.

B.

C.

FLUORESCENT SUBSTRATES FOR MONOAMINE TRANSPORTERS AS OPTICAL FALSE NEUROTRANSMITTERS

This application is a §371 national stage of PCT International Application No. PCT/US2007/017014, filed Jul. 27, 2007, and claims the benefit of U.S. Provisional Application No. 60/834,356, filed Jul. 27, 2006, the contents of all of which are hereby incorporated by reference into this application. Throughout this application, various publications are referenced by number in parentheses. Full citations for these references may be found at the end of the experimental section. The disclosures of these publications in their entireties are hereby incorporated by reference into this application in order to more fully describe the state of the art as known to those skilled therein as of the date of the invention described and claimed herein.

The invention disclosed herein was made with Government support under Grant Nos. DA10154 and DA007418 from the National Institute of Drug Abuse and NS-038370 from the National Institute of Neurological Disorders and Stroke. Accordingly, the U.S. Government has certain rights in this invention.

BACKGROUND OF THE INVENTION

The termination of neurotransmitter action is determined by a number of factors, including their reuptake into nerve terminals by monoamine transporters, their dilution by diffusion out of the synaptic cleft, and their metabolism by Monoamine Oxidase. Specific monoamine transporters located in the neuronal plasma membrane terminate the action of neurotransmitters by transporting them back into presynaptic terminals. Once inside the presynaptic terminal, vesicular monoamine transporters mediate their filling into secretory vesicles. All characterized monoaminergic cells utilize the vesicular monoamine transporter (VMAT) to accumulate monoamines from the cytoplasm into vesicles. These VMATs are polytopic membrane proteins, which act as electrogenic antiporters (exchangers) of protons and monoamines utilizing an acidic and positively polarized granule matrix.

The monoamine transporters of synapses formed by the midbrain dopamine projections are involved in voluntary motor control, reward and learning, and are the primary target of drugs of abuse including amphetamine, nicotine, cocaine as well as therapeutic agents that are used to treat mood disorders. Neuronal death in the substantia nigra is the cause of Alzheimer's disease and a decreased density of dopamine monoamine transporter has been found in Parkinson's, Wilson's, and Lesch-Nyhan's disease, while a decrease in serotonin monoamine transporter level is found in patients suffering from major depression and aggressive behavior.

Some evidence suggests that monoamine transporters recognize compounds other than neurotransmitters as substrates (1). This gave rise to the "false neurotransmitter hypothesis"—that different monoamines are transported into the same vesicle, resulting in the accumulation and release of so-called "false neurotransmitters". If, and to what extent, this apparent promiscuity is a fundamental biochemical property of the monoamine transporters still remains an unanswered question today.

The currently available molecular imaging tools do not enable monitoring of vesicle loading and release with spatial resolution of single terminals. The fluorescent amine acridine orange (21) accumulates in all acidic neuronal compartments, while fluorescent ASP+ stains mitochondria and cytosol but not vesicles (4,5,6,22). Currently, the dopamine transporter (DAT), norepinephrine transporter (NET) and serotonin transporter (SERT) activities are measured by ASP+, a fluorescent analog of MPP+. However, due to ASP+ and acridine orange's shortcomings mentioned above, they cannot be readily used to monitor transmission in living cells or brain slices.

Moreover, current approaches for direct measurement of monoamine release rely on microdialysis and electrochemical methods. Although electrochemical detection of dopamine (DA) release with cyclic voltammetry and amperometry has provided excellent temporal resolution, (38) these methods provide poor spatial resolution in brain tissue as they sample release and uptake of hundreds to thousands of DA terminals.

Herein is described a novel optical approach based on "optical fluorescent transmitters" or "fluorescent false neurotransmitters" ("FFNs") that act as optical tracers, providing the first direct means to directly visualize neurotransmitter uptake, redistribution, and release from individual dopamine terminals. FFNs were designed by targeting the synaptic vesicular monoamine transporter (VMAT2) that transports dopamine and other aminergic neurotransmitters from the cytoplasm into synaptic vesicles. Like dopamine, these probes selectively accumulate in dopamine and other aminergic neurotransmitters from cytoplasm into vesicles. Like dopamine, these probes selectively accumulate in dopamine terminals in the brain in a manner dependent on VMAT2 function and the vesicular pH gradient, and are released upon synaptic firing.

SUMMARY OF THE INVENTION

One embodiment of the invention provides a compound having the following structure:

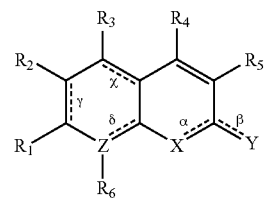

wherein
Y is O, X is O, bond α is absent and bond β is present, or
Y is H, X is CH, bond α is present, and bond β is absent;
atom Z is a carbon and bonds χ, δ and γ are present, or
atom Z is a nitrogen and bonds χ, δ and γ are absent, or
atom Z is a nitrogen and bonds χ, δ and γ are present and γ is absent;
$R_1$ is —H, —OH, —O—$R_7$, —N(H)—$R_8$, —N($R_{34}$)—($CH_2$)$_n$—N($R_{34}$)$_2$, —N($R_{34}$)alkyl, —N($R_{34}$)$_2$, —N($R_9$)($R_{10}$) a piperazine cation, or is bound to $R_{19}$,
   wherein n is an integer,
   wherein $R_7$ and $R_8$ are, independently, alkyl, alkenyl or alkynyl, or $R_7$ and Re are covalently bound to $R_2$ and $R_6$, respectively,
   wherein $R_9$ and $R_{10}$ are, independently, alkyl, alkenyl or alkynyl, or $R_9$ and $R_{10}$ are covalently bound to $R_2$ and $R_6$, respectively,
   where each occurrence of $R_{34}$ is, independently, —H, —$CH_3$ or —$C_2H_5$;
$R_2$ is either covalently bound to $R_9$, or is —H, or is covalently bound to $R_3$ so as to form a substituted or unsubstituted pyrrole, or is $N(R_{19})(R_{20})$ wherein $R_{19}$ and $R_{20}$ are covalently bound to $R_1$ and $R_3$, respectively;

or $R_1$ and $R_2$ are covalently joined to form an unsubstituted or substituted aromatic ring or a saturated ring;

$R_3$ is either covalently bound to $R_2$ so as to form a substituted or unsubstituted pyrrole, or is —H, —OH, alkyl, alkenyl, alkynyl, halo, or is bound to $R_{20}$, or when Z is nitrogen $R_3$ is =O or —H, $R_4$ is —H, —OH, halo, alkyl, alkenyl, alkynyl, —$R_{11}N(R_{35})_2$, —$N(R_{35})R_{17}N(R_{35})_2$, —$R_{17}N(H)R_{18}$, —$R_{11}NR_{13}R_{14}$, —$N(R_{35})$alkyl, —$N(R_{35})_2$, or a piperazine group, wherein $R_{11}$ is a straight or a branched chain alkylene, alkenylene or alkynylene, and wherein the $(R_{35})_2$ group may be attached to any carbon atom of the $R_{11}$ group, wherein $R_{13}$ or $R_{14}$ or both are, independently, methyl or ethyl, wherein $R_{17}$ is a straight or a branched chain alkylene, alkenylene or alkynylene, wherein $R_{18}$ is a straight or a branched chain alkyl, alkenyl or alkynyl, where each occurrence of $R_{35}$ is, independently, —H, —$CH_3$ or —$C_2H_5$;

$R_5$ is —H, —OH, halo, alkyl, alkenyl, alkynyl, —$R_{12}N(R_{36})_2$, $R_{11}NR_{15}R_{16}$, —$N(R_{36})$alkyl, —$N(R_{36})_2$, a piperazine group, a mono-substituted heterocyclyl or —$R_{19}W$, wherein $R_{12}$ is a straight or a branched chain alkylene, alkenylene or alkynylene, and wherein the $NH_2$ group may be attached to any carbon atom of the $R_{12}$ group, wherein $R_{15}$ or $R_{16}$ or both are, independently, methyl or ethyl, wherein $R_{19}$ is a straight or a branched chain alkylene, alkenylene or alkynylene, wherein W is a mono- or di-substituted heterocyclyl group or a mono-substituted heterocyclyl cation, where each occurrence of $R_{36}$ is, independently, —H, —$CH_3$ or —$C_2H_5$; and $R_6$ is either covalently bound to $R_{10}$, is —H, or is absent;

wherein when $R_5$ is —$CH_2$—$CH(CH_3)$—$NH_2$ and $R_2$, $R_3$, $R_4$ and $R_6$ are each —H, $R_1$ is —OH, —O—$R_6$, —N(H)—$R_7$, —N(H)—$(CH_2)_n$—$NH_2$, —$N(R_9)(R_{10})$, —N(H)alkyl, —N(alkyl)$_2$, or a piperazine cation;

wherein the compound contains an $N(R_x)$ or $N(R_x)_2$ group wherein each occurrence of $R_x$ is, independently, —H, —$CH_3$ or —$C_2H_5$.

One embodiment of this invention provides a compound of the structure:

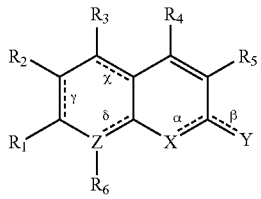

wherein

Y is O, X is O, bond α is absent and bond β is present, or Y is H, X is CH, bond α is present, and bond β is absent; atom Z is a carbon and bonds χ, δ and γ are present, or atom Z is a nitrogen and bonds χ, δ and γ are absent;

$R_1$ is —H, —OH, —O—$R_7$, —N(H)—$R_8$, —N(H)—$(CH_2)_n$—$NH_2$, —$N(R_9)(R_{10})$, or a piperazine cation, wherein n is an integer, wherein $R_7$ and $R_8$ are, independently, alkyl, alkenyl or alkynyl, or $R_7$ and $R_8$ are covalently bound to $R_2$ and $R_6$, respectively, wherein $R_9$ and $R_{10}$ are, independently, alkyl, alkenyl or alkynyl, or $R_9$ and $R_{10}$ are covalently bound to $R_2$ and $R_6$, respectively;

$R_2$ is either covalently bound to $R_9$, or is —H, or is covalently bound to $R_3$ so as to form a substituted or unsubstituted pyrrole;

or $R_1$ and $R_2$ are covalently joined to form an unsubstituted or substituted aromatic ring or a saturated ring;

$R_3$ is either covalently bound to $R_2$ so as to form a substituted or unsubstituted pyrrole, or is —H, —OH, alkyl, alkenyl, alkynyl, halo, or when Z is nitrogen $R_3$ is =O, $R_4$ is —H, —OH, halo, alkyl, alkenyl, alkynyl, —$R_{11}NH_2$, or $R_{11}NR_{13}R_{14}$, wherein $R_{11}$ is a straight or a branched chain alkylene, alkenylene or alkynylene, and wherein the $NH_2$ group may be attached to any carbon atom of the $R_{11}$ group, wherein $R_{13}$ or $R_{14}$ or both are, independently, methyl or ethyl;

$R_5$ is —H, —OH, halo, alkyl, alkenyl, alkynyl, —$R_{12}NH_2$, or $R_{11}NR_{15}R_{16}$, wherein $R_{12}$ is a straight or a branched chain alkylene, alkenylene or alkynylene, and wherein the $NH_2$ group may be attached to any carbon atom of the $R_{12}$ group, wherein $R_{15}$ or $R_{16}$ or both are, independently, methyl or ethyl; and $R_6$ is either covalently bound to $R_{10}$ or is —H;

wherein when $R_5$ is —$CH_2$—$CH(CH_3)$—$NH_2$ and $R_2$, $R_3$, $R_4$ and $R_6$ are each —H, $R_1$ is —OH, —O—$R_6$, —N(H)—$R_7$, —N(H)—$(CH_2)_n$—$NH_2$, —$N(R_9)(R_{10})$, or a piperazine cation; wherein the compound contains an $NH_2$ group.

A compound having the following structure:

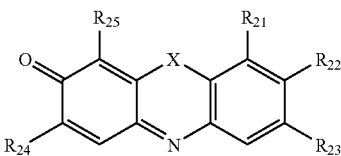

wherein X is O, S or C—$(CH_3)_2$;

$R_{21}$ is —H, -halo, or —$R_{26}N(R_{27})_2$, where $R_{26}$ is a straight or branched chain alkylene and the $(NH_2)$ group may be attached to any carbon atom of $R_{26}$, and wherein each $R_{27}$ is, independently, —H, —$CH_3$ or —$C_2H_5$;

$R_{22}$ is —OH, —$OCH_3$, —$OCH_2CH_3$, —$O(CH_2)_nN(R_{28})_2$, —$N(H)(CH_2)_mN(R_{28})_2$, —$R_{29}N(R_{28})_2$, —$NR_{30}(CH_2)_p N(R_{28})_2$, or a piperazine cation, where $R_{29}$ and $R_{30}$ are, independently, a straight or branched chain alkylene and where the $(NH_2)$ group may be attached to any carbon atom of $R_{29}$ or $R_{30}$, where each $R_{28}$ is, independently, —H, —$CH_3$ or —$C_2H_5$, where n=1 to 8, m=1 to 8 and p=1 to 8;

$R_{23}$ is —H, -halo, or —$R_{31}N(R_{32})_2$, —$OCH_2CH_3$, —$O(CH_2)_nN(R_{32})_2$, —$N(H)(CH_2)_mN(R_{32})_2$, —$NR_{33}(CH_2)_pN(R_{32})_2$, or a piperazine cation, where $R_{31}$ and $R_{33}$ are, independently, a straight or branched chain alkylene and where the $(NH_2)$ group may be attached to any carbon atom of $R_{31}$ or $R_{33}$, where each $R_{32}$ is, independently, —H, —CH$_3$ or —C$_2$H$_5$, where n=1 to 8, m=1 to 8 and p=1 to 8;

$R_{24}$ and $R_{25}$ are, independently, —H or -halo.

DETAILED DESCRIPTION

Figure 1:
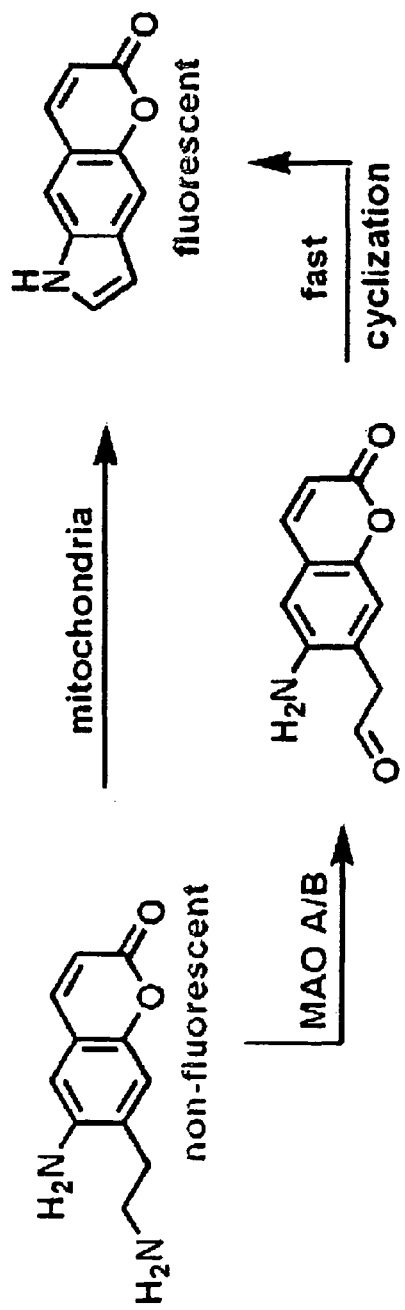
FIG. 1: An example of design of fluorogenic metabolic indicators; a selective probe for monoamine oxidase (MAO) based on a built-in redox optical switch.

Abbreviations used in the specification:
VMAT—Vesicular Monoamine Transporter
DAT—Dopamine Transporter
NET—Norepinephrine transporter
SERT—Serotonin Transporter
A compound having the following structure:

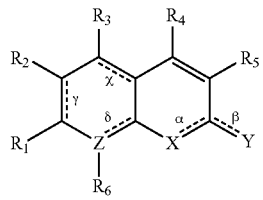

wherein

Y is O, X is O, bond α is absent and bond β is present, or Y is H, X is CH, bond α is present, and bond β is absent;
atom Z is a carbon and bonds χ, δ and γ are present, or atom Z is a nitrogen and bonds χ, δ and γ are absent, or atom Z is a nitrogen and bonds χ and δ are present and γ is absent;

$R_1$ is —H, —OH, —O—$R_7$, —N(H)—$R_8$, —N(H)—$(CH_2)_n$—$NH_2$, —N(H)alkyl, —N(alkyl)$_2$, —N($R_9$)($R_{10}$) a piperazine cation, or is bound to $R_{19}$,
wherein n is an integer,
wherein $R_7$ and $R_8$ are, independently, alkyl, alkenyl or alkynyl, or $R_7$ and $R_8$ are covalently bound to $R_2$ and $R_6$, respectively,
wherein $R_9$ and $R_{10}$ are, independently, alkyl, alkenyl or alkynyl, or $R_9$ and $R_{10}$ are covalently bound to $R_2$ and $R_6$, respectively;

$R_2$ is either covalently bound to $R_9$, or is —H, or is covalently bound to $R_3$ so as to form a substituted or unsubstituted pyrrole, or is N($R_{19}$)($R_{20}$) wherein $R_{19}$ and $R_{20}$ are covalently bound to $R_1$ and $R_3$, respectively; or $R_1$ and $R_2$ are covalently joined to form an unsubstituted or substituted aromatic ring or a saturated ring;

$R_3$ is either covalently bound to $R_2$ so as to form a substituted or unsubstituted pyrrole, or is —H, —OH, alkyl, alkenyl, alkynyl, halo, or is bound to $R_{20}$, or when Z is nitrogen $R_3$ is =O or —H, $R_4$ is —H, —OH, halo, alkyl, alkenyl, alkynyl, 13 $R_{11}NH_2$, —NHR$_{17}$NH$_2$, —R$_{17}$N(H)R$_{18}$, —R$_{11}$NR$_{13}$R$_{14}$, —N(H)alkyl, —N(alkyl)$_2$, or a piperazine group,
wherein $R_{11}$ is a straight or a branched chain alkylene, alkenylene or alkynylene,
and wherein the NH$_2$ group may be attached to any carbon atom of the $R_{11}$ group,
wherein $R_{13}$ or $R_{14}$ or both are, independently, methyl or ethyl,
wherein $R_{17}$ is a straight or a branched chain alkylene, alkenylene or alkynylene and
wherein $R_{18}$ is a straight or a branched chain alkyl, alkenyl or alkynyl;

$R_5$ is —H, —OH, halo, alkyl, alkenyl, alkynyl, —$R_{12}NH_2$, $R_{11}NR_{15}R_{16}$, —N(H)alkyl, —N(alkyl)$_2$, a piperazine group, a mono-substituted heterocyclyl or —$R_{19}W$,
wherein $R_{12}$ is a straight or a branched chain alkylene, alkenylene or alkynylene,
and wherein the NH$_2$ group may be attached to any carbon atom of the $R_{12}$ group,
wherein $R_{15}$ or $R_{16}$ or both are, independently, methyl or ethyl,
wherein $R_{19}$ is a straight or a branched chain alkylene, alkenylene or alkynylene,
wherein W is a mono- or di-substituted heterocyclyl group or a mono-substituted heterocyclyl cation; and
$R_6$ is either covalently bound to $R_{10}$, is —H, or is absent;
wherein when $R_5$ is —CH$_2$—CH(CH$_3$)—NH$_2$ and $R_2$, $R_3$, $R_4$ and $R_6$ are each —H, $R_1$ is —OH, —O—$R_6$, —N(H)—$R_7$, —N(H)—(CH$_2$)$_n$—NH$_2$, —N($R_9$)($R_{10}$), —N(H)alkyl, —N(alkyl)$_2$, or a piperazine cation;
wherein the compound contains an NH$_2$ group or an NH group.

In an embodiment $R_5$ is a mono-substituted heterocyclyl group wherein the heteroatom is nitrogen. In an embodiment W is a mono-substituted heterocyclyl group wherein the heteroatom is nitrogen. In an embodiment W is a di-substituted heterocyclyl group wherein the heteroatoms are each nitrogen. In an embodiment W is a piperazine group. In an embodiment $R_1$ is —N(CH$_3$)$_2$, —OCH$_3$, or —N($R_9$)($R_{10}$) wherein $R_9$ and $R_{10}$ are each —C$_3$H$_6$— and are covalently bound to $R_2$ and $R_6$, respectively. In an embodiment $R_2$ is —N($R_{19}$)($R_{20}$) wherein $R_{19}$ and $R_{20}$ are each —C$_3$H$_6$— and are covalently bound to $R_1$ and $R_3$, respectively. In an embodiment $R_1$ and $R_2$ are covalently joined to form an unsubstituted six-membered aromatic ring. In an embodiment $R_4$ is —H, —CH$_2$CH$_2$NHCH$_3$, —CH$_2$CH(CH$_3$)NH$_2$, —NHCH$_3$CH$_2$NH$_2$, —CH$_2$NH$_2$, or a piperazine group. In an embodiment $R_5$ is —CH$_2$CH$_2$NH$_2$, a piperazine group, a piperazine cation, a pyrrolidin-2-yl group, a piperidinyl group. In an embodiment —N(H)alkyl is —N(H)CH$_3$ or —NH(CH$_2$CH$_3$). In an embodiment —N(alkyl)$_2$ is —N(CH$_3$)$_2$ or —N(CH$_2$CH$_3$)$_2$. In an embodiment $R_3$ is —H. In an embodiment $R_6$ is —H.

In an embodiment the compound has the structure:

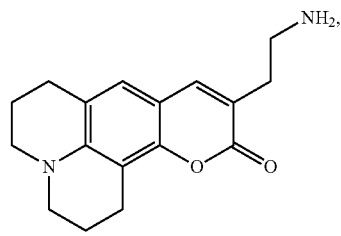

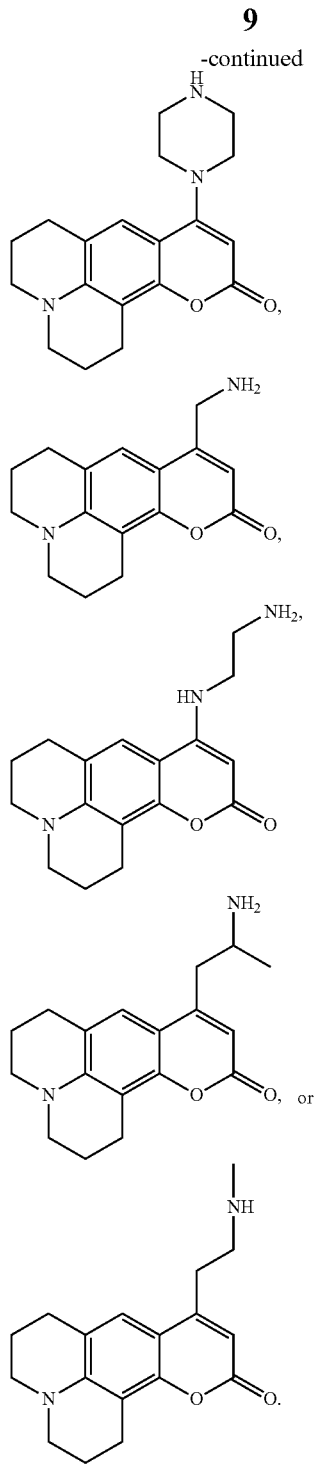
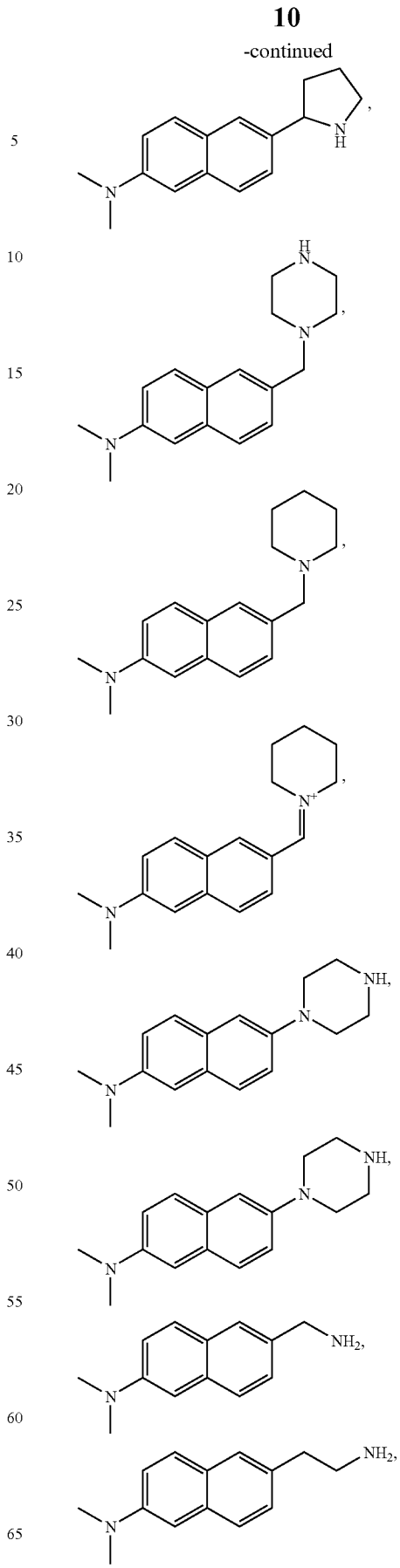
In an embodiment the compound has the structure:
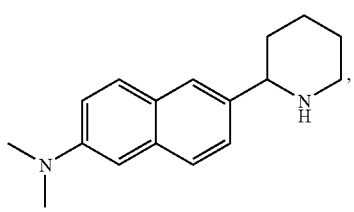

-continued

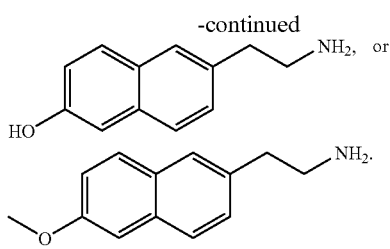

In one embodiment, this invention provides compounds of the general structure:

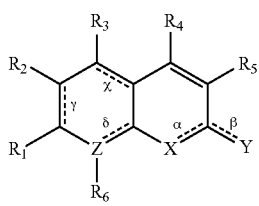

wherein
Y is O, X is O, bond α is absent and bond β is present, or
Y is H, X is CH, bond α is present, and bond β is absent;
atom Z is a carbon and bonds χ, δ and γ are present, or
atom Z is a nitrogen and bonds χ, δ and γ are absent;
$R_1$ is —H, —OH, —O—$R_7$, —N(H)—$R_8$, —N(H)—$(CH_2)_n$—$NH_2$, N($R_9$)($R_{10}$), or a piperazine cation,
  wherein n is an integer,
  wherein $R_7$ and $R_8$ are, independently, alkyl, alkenyl or alkynyl, or $R_7$ and $R_8$ are covalently bound to $R_2$ and $R_6$, respectively,
  wherein $R_9$ and $R_{10}$ are, independently, alkyl, alkenyl or alkynyl, or $R_9$ and $R_{10}$ are covalently bound to $R_2$ and $R_6$, respectively;
$R_2$ is either covalently bound to $R_9$, or is —H, or is covalently bound to $R_3$ so as to form a substituted or unsubstituted pyrrole;
or $R_1$ and $R_2$ are covalently joined to form an unsubstituted or substituted aromatic ring or a saturated ring;
$R_3$ is either covalently bound to $R_2$ so as to form a substituted or unsubstituted pyrrole, or is —H, —OH, alkyl, alkenyl, alkynyl, halo, or when Z is nitrogen $R_3$ is =O,
$R_4$ is —H, —OH, halo, alkyl, alkenyl, alkynyl, —$R_{11}NH_2$, or $R_{11}NR_{13}R_{14}$,
  wherein $R_{11}$ is a straight or a branched chain alkylene, alkenylene or alkynylene,
  and wherein the $NH_2$ group may be attached to any carbon atom of the $R_{11}$ group,
  wherein $R_{13}$ or $R_{14}$ or both are, independently, methyl or ethyl;
$R_5$ is —H, —OH, halo, alkyl, alkenyl, alkynyl, —$R_{12}NH_2$, or $R_{11}NR_{15}R_{16}$,
  wherein $R_{12}$ is a straight or a branched chain alkylene, alkenylene or alkynylene,
  and wherein the $NH_2$ group may be attached to any carbon atom of the $R_{12}$ group,
  wherein $R_{15}$ or $R_{16}$ or both are, independently, methyl or ethyl; and
$R_6$ is either covalently bound to $R_{10}$ or is —H;
wherein when $R_5$ is —$CH_2$—$CH(CH_3)$—$NH_2$ and $R_2$, $R_3$, $R_4$ and $R_6$ are each —H, $R_1$ is —OH, —O—$R_6$, —N(H)—$R_7$, —N(H)—$(CH_2)_n$—$NH_2$, —N($R_9$)($R_{10}$), or a piperazine cation;

wherein the compound contains an $NH_2$ group.
In an embodiment, Z is carbon.
In an embodiment the compound has the following structure:

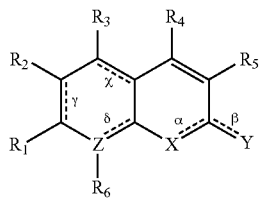

wherein
Y is O, X is O, bond α is absent and bond β is present, or
Y is H, X is CH, bond α is present, and bond β is absent;
atom Z is a carbon and bonds χ, δ and γ are present, or
atom Z is a nitrogen and bonds χ, δ and γ are absent;
$R_1$ is —H, —OH, —O—$R_7$, —N(H)—$R_8$, —N(H)—$(CH_2)_n$—$NH_2$, —N($R_9$)($R_{10}$), or a piperazine cation,
  wherein n is an integer,
  wherein $R_7$ and $R_8$ are, independently, alkyl, alkenyl or alkynyl,
  wherein $R_9$ and $R_{10}$ are, independently, alkyl, alkenyl or alkynyl, or $R_9$ and $R_{10}$ are covalently bound to $R_2$ and $R_6$, respectively;
$R_2$ is either covalently bound to $R_9$, or is —H, or is covalently bound to $R_3$ so as to form a substituted or unsubstituted pyrrole;
or $R_1$ and $R_2$ are covalently joined to form an unsubstituted or substituted aromatic ring;
$R_3$ is either covalently bound to $R_2$ so as to form a substituted or unsubstituted pyrrole, or is —H, —OH, alkyl, alkenyl, alkynyl, halo, or when Z is nitrogen $R_3$ is =O,
$R_4$ is —H, —OH, halo, alkyl, alkenyl, alkynyl, or —$R_{11}NH_2$,
  wherein $R_{11}$I is a straight or a branched chain alkylene, alkenylene or alkynylene,
  and wherein the $NH_2$ group may be attached to any carbon atom of the $R_{11}$ group;
$R_5$ is —H, —OH, halo, alkyl, alkenyl, alkynyl, or —$R_{12}NH_2$,
  wherein $R_{12}$ is a straight or a branched chain alkylene, alkenylene or alkynylene, and wherein the $NH_2$ group may be attached to any carbon atom of the $R_{12}$ group; and
$R_6$ is either covalently bound to $R_{10}$ or is —H;
wherein when $R_5$ is —$CH_2$—$CH(CH_3)$—$NH_2$ and $R_2$, $R_3$, $R_4$ and $R_6$ are each —H, $R_1$ is —OH, —O—$R_6$, —N(H)—$R_7$, —N(H)—$(CH_2)_n$—$NH_2$, —N($R_9$)($R_{10}$), or a piperazine cation;

wherein the compound contains an $NH_2$ group.
In an embodiment, the alpha position of the amino group is methylated.

In an embodiment, the compound has following structure:

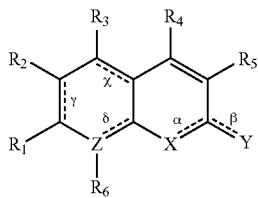

wherein

Y is O, X is O, bond α is absent and bond β is present, or

Y is H, X is CH, bond α is present, and bond β is absent;

Z is a carbon and bonds χ, δ and γ are present, or

Z is a nitrogen and bonds χ, δ and γ are absent;

$R_1$ is —H, —OH, —O—$CH_3$, —N(H)—$C_2H_4$—$NH_2$, a piperazine cation, or —N($R_9$)($R_{10}$) wherein $R_9$ and $R_{10}$ are each propylene and are covalently bound to $R_2$ and $R_6$, respectively;

$R_2$ is —H, or is covalently bound to $R_3$ so as to form a pyrrole substituted with an aminoethyl group, or is covalently bound to $R_9$;

or $R_1$ and $R_2$ are covalently joined to form an unsubstituted six-membered aromatic ring;

$R_3$ is —H, =O, or is covalently bound to $R_2$ so as to form a pyrrole substituted with an aminoethyl group;

$R_4$ is —H, —OH, —$CH_3$ or —$C_2H_4NH_2$;

$R_5$ is —H, —$C_2H_4NH_2$, or —$CH_2$—CH($CH_3$)—$NH_2$; and $R_6$ is —H, or is covalently bound to $R_{10}$;

wherein when $R_5$ is —$CH_2$—CH($CH_3$)—$NH_2$ and $R_2$, $R_3$, $R_4$ and $R_6$ are each —H, $R_1$ is —OH or —O—$CH_3$, and wherein the compound contains a $NH_2$ group.

This invention provides a compound having the structure:

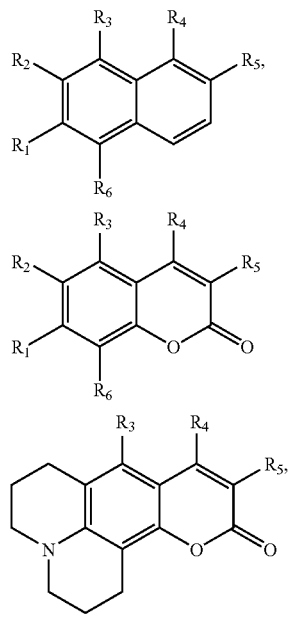

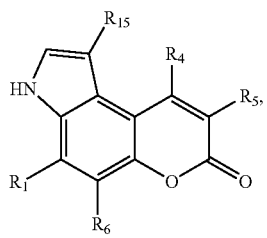

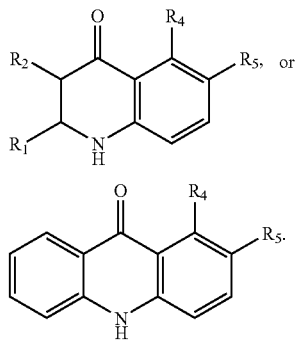

wherein $R_1$-$R_6$ are defined as above.

In one embodiment of the instant compounds, $R_7$ is $CH_3$. In embodiments, $R_{15}$ is H, OH, alklyl, alkenyl or alkenyl, alkylene-$NH_2$, alkenylene-$NH_2$ or alkynylene-$NH_2$. In an embodiment, $R_1$ is —N(H)—$(CH_2)_n$—$NH_2$ and n is 2. In an embodiment, $R_4$ is $CH_3$ or —$C_2H_4NH_2$. In an embodiment, $R_1$ is —N($R_9$)($R_{10}$) wherein $R_8$ and $R_9$ are each —$C_3H_6$— and are covalently bound to $R_2$ and $R_6$, respectively. In an embodiment, $R_2$ and $R_3$ form a pyrrole substituted with an aminoethyl group. In an embodiment, $R_5$ is —$C_2H_4NH_2$. In an embodiment, $R_3$ and $R_5$ are —H and $R_4$ is —$C_2H_4NH_2$. In an embodiment, $R_1$, $R_5$ and $R_6$ are —H, $R_4$ is —$CH_3$, and $R_{15}$ is —$C_2H_4NH_2$. In an embodiment, $R_1$ is a piperazine cation, $R_2$, $R_3$, $R_5$ and $R_6$ are —H, and $R_4$ is —$CH_3$. In an embodiment, $R_1$ is a piperazine cation, $R_2$, $R_3$, $R_5$ and $R_6$ are —H, and $R_4$ is —OH. In an embodiment, $R_1$ is a —O—$CH_3$, $R_2$, $R_3$, $R_4$ and $R_6$ are —H, and $R_5$ is —$CH_2$—CH($CH_3$)—$NH_2$. In an embodiment, $R_1$ is a —OH, $R_2$, $R_3$, $R_4$ and $R_6$ are —H, and $R_5$ is —$CH_2$—CH($CH_3$)—$NH_2$. In an embodiment, $R_4$ is —H, and $R_5$ is —$C_2H_4NH_2$. In an embodiment, $R_1$ and $R_2$ are covalently joined to form an unsubstituted six-membered aromatic ring. In an embodiment, $R_2$, $R_3$, $R_4$, $R_5$ and $R_6$ are —H, and $R_1$ is —N(H)—$C_2H_4$—$NH_2$. In this disclosure, —$CH_2$—CH($CH_3$)—$NH_2$ and —$CH_2$—CH($NH_2$)—$CH_3$ are used interchangeably.

In embodiments, the compound has the structure:

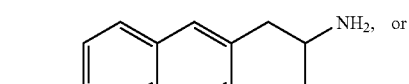

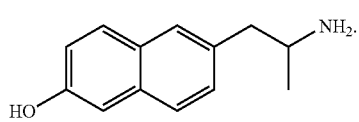

In embodiments, the compound has the structure:

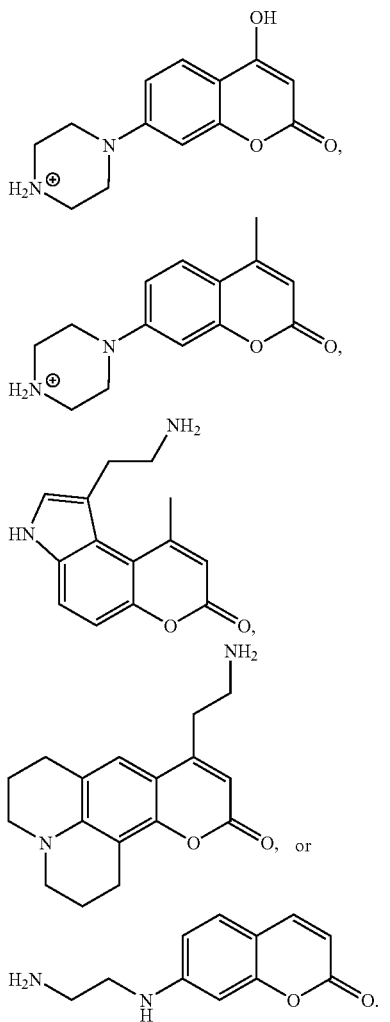

In embodiments, the compound has the structure:

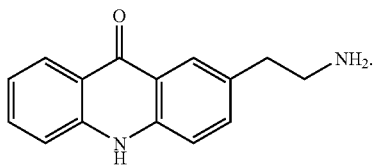

A compound having the following structure:

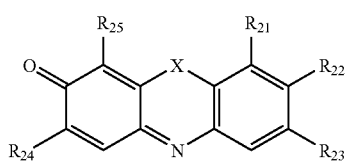

wherein X is O, S or C—(CH$_3$)$_2$;
R$_{21}$ is —H, -halo, or —R$_{26}$N(R$_{27}$)$_2$, where R$_{26}$ is a straight or branched chain alkylene and the N(R$_{27}$)$_2$ group may be attached to any carbon atom of R$_{26}$, and wherein each R$_{27}$ is, independently, —H, —CH$_3$ or —C$_2$H$_5$;

R$_{22}$ is —OH, —OCH$_3$, —OCH$_2$CH$_3$, —O(CH$_2$)$_n$N(R$_{28}$)$_2$, —N(H)(CH$_2$)$_m$N(R$_{28}$)$_2$, —R$_{29}$N(R$_{28}$)$_2$, —NR$_{30}$(CH$_2$)$_p$N(R$_{28}$)$_2$, or a piperazine cation, where R$_{29}$ and R$_{30}$ are, independently, a straight or branched chain alkylene and where the N(R$_{28}$)$_2$ group may be attached to any carbon atom of R$_{29}$ or R$_{30}$, where each R$_{28}$ is, independently, —H, —CH$_3$ or —C$_2$H$_5$, where n=1 to 8, m=1 to 8 and p=1 to 8;

R$_{23}$ is —H, -halo, or —R$_{31}$N(R$_{32}$)$_2$, —OCH$_2$CH$_3$, —O(CH$_2$)$_n$N(R$_{32}$)$_2$, —N(H)(CH$_2$)$_m$N(R$_{32}$)$_2$, —NR$_{33}$(CH$_2$)$_p$N(R$_{32}$)$_2$, or a piperazine cation, where R$_{31}$ and R$_{33}$ are, independently, a straight or branched chain alkylene and where the N(R$_{32}$)$_2$ group may be attached to any carbon atom of R$_{31}$ or R$_{33}$, where each R$_{32}$ is, independently, —H, —CH$_3$ or —C$_2$H$_5$, where n=1 to 8, m=1 to 8 and p=1 to 8;

R$_{24}$ and R$_{25}$ are, independently, —H or -halo.

In an embodiment R$_{30}$ and/or R$_{33}$ is/are —H, —CH$_3$ or —C$_2$H$_5$.

In an embodiment, the compound has the structure:

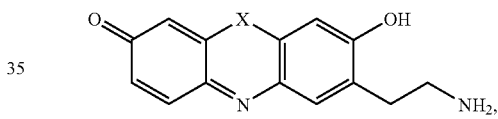

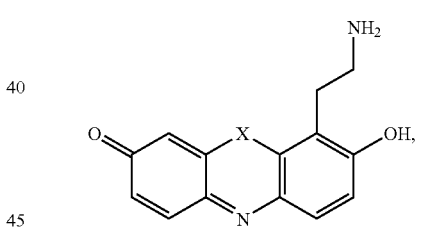

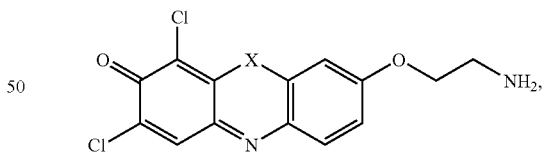

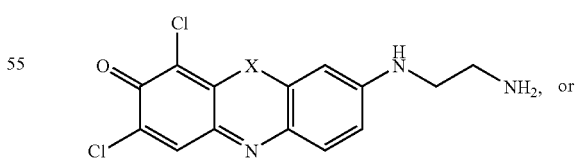

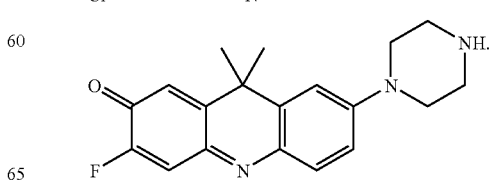

This invention provides a process for producing the instant compound comprising:

a) reacting a compound having the structure:

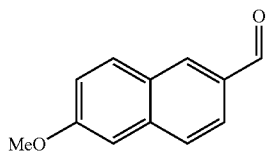

with nitro-ethane so as to produce a product having the structure:

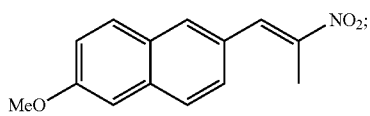

and b) reacting the product of step a) with a suitable reducing agent in a suitable solvent so as to produce a product having the structure:

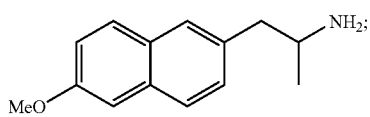

c) optionally, demethylating the product of step b) with BBr₃ in a suitable solvent so as to thereby produce the compound.

In an embodiment, the suitable reducing agent in step b) is LiAlH₄. In an embodiment, the suitable solvent in step b) is THF. In an embodiment, the suitable solvent in step c) is DCM.

This invention provides a process for producing the instant compound comprising demethylating a compound having the structure:

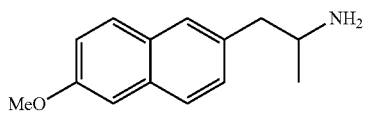

with BBr₃ in a suitable solvent so as to thereby produce the compound

This invention provides a process for producing the instant compound comprising:

a) reacting a compound having the structure:

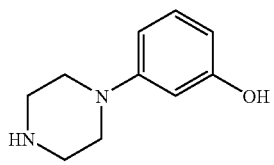

with a suitable protecting group agent in a suitable solvent so as to produce a product having the structure:

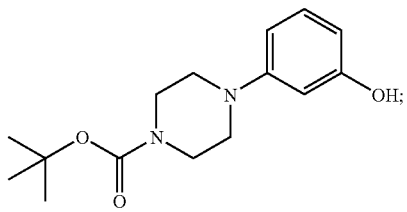

b) reacting the product of step a) with ethyl acetoacetate and a suitable catalyst in a suitable solvent;

c) reacting the product of step b) with a suitable protecting group agent in a suitable solvent so as to produce a product having the structure:

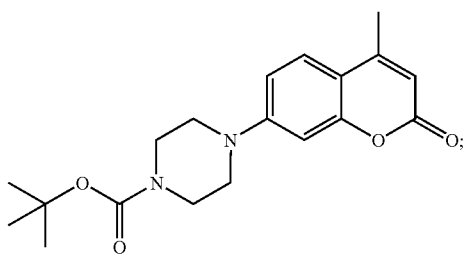

and d) reacting the product of step c) with TFA in dry CH₂Cl₂ so as to thereby produce the compound.

In an embodiment, the suitable protecting group agent in step a) is di-tert-butyl pyrocarbonate. In an embodiment, the suitable solvent in step a) is a mixture of Et₃N and DMF. In an embodiment, the suitable solvent in step b) is EtOH. In an embodiment, the suitable catalyst in step b) is InCl₃. In an embodiment, the suitable protecting group agent in step c) is di-tert-butyl pyrocarbonate. In an embodiment, the suitable solvent in step c) is a mixture of Et₃N and CHCl₃-MeOH.

This invention provides a process for producing the instant compound comprising:

a) reacting a compound having the structure:

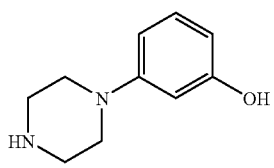

with a suitable protecting group agent in a suitable solvent so as to produce a product having the structure:

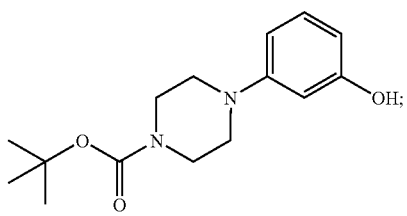

b) reacting the product of step a) with a compound having the structure:

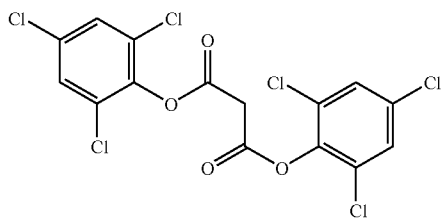

in a suitable solvent; and c) reacting the product of step b) with TFA in dry $CH_2Cl_2$ so as to thereby produce the compound.

In an embodiment, the suitable protecting group agent in step a) is di-tert-butyl pyrocarbonate. In an embodiment, the suitable solvent in step a) is a mixture of $Et_3N$ and DMF. In an embodiment, the suitable solvent in step b) is toluene.

This invention provides a process for producing the instant compound, comprising:

a) reacting a compound having the structure:

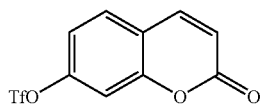

with a compound having the structure:

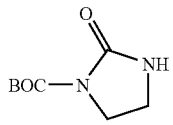

in the presence of Pd(dibenzylideneacetone)$_2$, a compound having the structure:

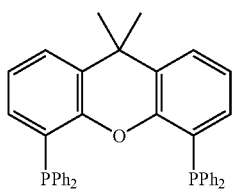

and a suitable base in a suitable solvent so as to produce a product having the structure:

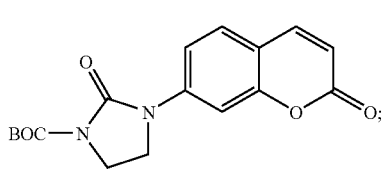

and b) heating the product of step a) in a suitable acid for a time sufficient to produce the compound.

In an embodiment, the suitable base in step a) is $Cs_2CO_3$. In an embodiment, the suitable solvent in step a) is toluene or dioxane. In an embodiment, the suitable acid in step b) is sulfuric acid.

This invention provides a process for producing the instant compound comprising:

a) reacting a compound having the structure:

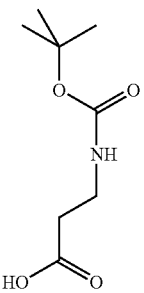

with:

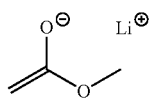

in the presence of carbodiimidazole in a suitable solvent so as to produce a product having the structure:

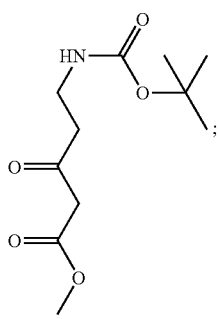

b) reacting the product of step a) with a compound having the structure:

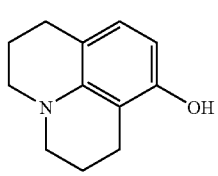

in the presence of InCl$_3$ so as to produce a compound having the structure:

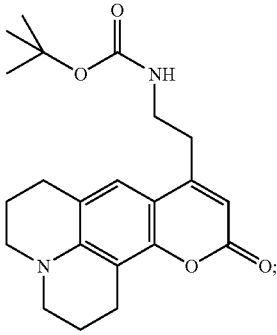

and c) reacting the product of step b) with a suitable acid in dry CH$_2$Cl$_2$ so as to prouce the compound.

In an embodiment, the suitable solvent in step a) is THF. In an embodiment, the suitable acid in step c) is trifluoroacetic acid.

This invention provides a process for producing the instant compound comprising:

a) reacting a compound having the structure:

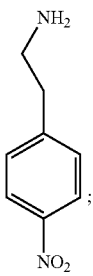

with a suitable protecting group agent in a suitable solvent so as to produce a product having the structure:

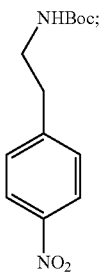

b) reacting the product of step a) with H$_2$ in the presence of a suitable catalyst so as to produce a product having the structure:

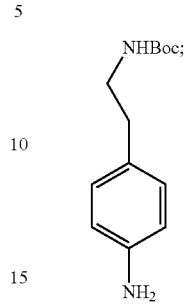

c) reacting the product of step b) with a compound having the structure:

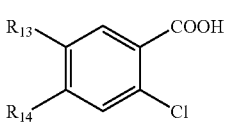

wherein R$_{13}$ and R$_{14}$ are, independently, H, OH, alkyl, alkenyl, or alkenyl, in the presence of a suitable catalyst, a suitable base and a suitable solvent so as to produce a compound having the structure:

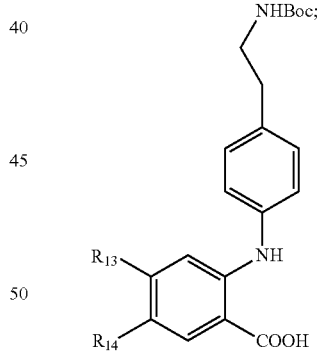

and d) reacting the product of step c) with polyphosphoric acid so as to produce the compound.

In an embodiment, the suitable protecting group agent in step a) is di-tert-butyl pyrocarbonate. In an embodiment, the suitable solvent in step a) is a mixture of Et$_3$N and DMF. In an embodiment, the suitable catalyst in step b) is Pd/C. In an embodiment, the suitable catalyst in step c) is Cu. In an embodiment, suitable base in step c) is K$_2$CO$_3$. In an embodiment, the suitable solvent in step c) is DMF. In an embodiment, R$_{13}$ and R$_{14}$ are both —H.

This invention provides a process for producing the instant compound comprising reacting a compound having the structure:

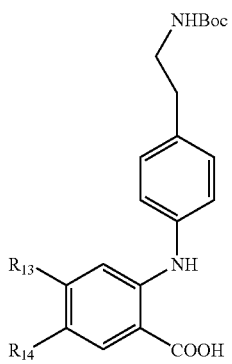

wherein $R_{13}$ and $R_{14}$ are, independently, H, OH, alkyl, alkenyl, or alkenyl, with polyphosphoric acid so as to produce the compound.

This invention provides a compound having the structure:

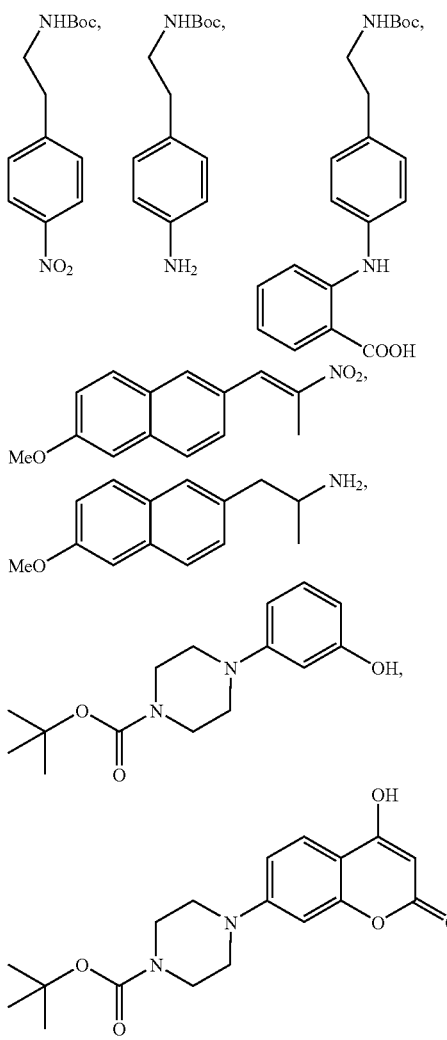

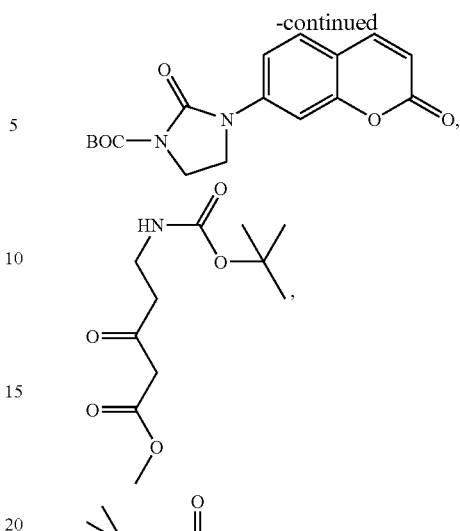

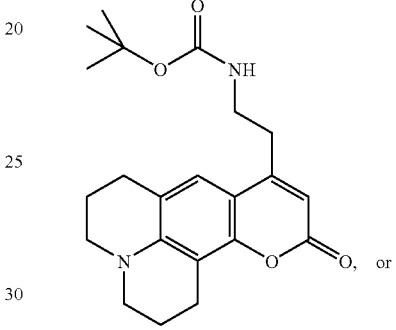

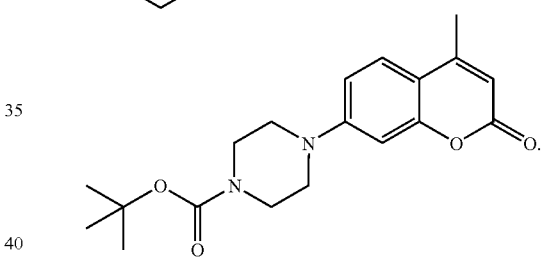

This invention provides a method for detecting an active monoamine transporter in a sample comprising:

a) providing a sample;

b) quantitating fluorescence of the sample;

c) contacting the sample with the instant compound for a time sufficient that an active monoamine transporter present in the sample can uptake the compound;

d) washing the sample so as to remove any of the compound that has not been transported by the active monoamine transporter; and e) quantitating fluorescence of the sample, wherein an increase in the fluorescence of the sample quantitated in step e) over the fluorescence quantified in step b) indicates the presence of an active monoamine transporter.

In an embodiment, the sample is mammalian nervous tissue or mammalian endocrine tissue.

In an embodiment, the active monoamine transporter is a vesicular monoamine transporter 1. In an embodiment, the active monoamine transporter is a vesicular monoamine transporter 2. In an embodiment, wherein the compound used in step c) has the structure:

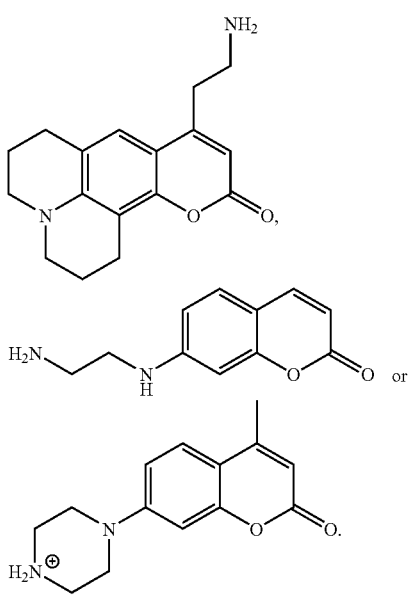

In an embodiment, the active monoamine transporter is a dopamine transporter, norepinephrine transporter or a serotonin transporter. In an embodiment, the active monoamine transporter is a dopamine transporter and compound used in step c) has the structure:

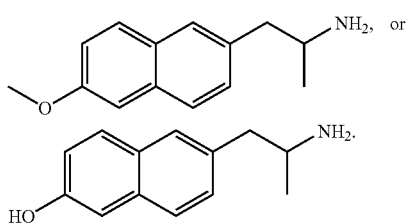

This invention provides a process of identifying a compound which is an inhibitor of a monoamine transporter comprising:
- a) providing a sample comprising a monoamine transporter in a medium;
- b) contacting the sample with the instant compound for a time sufficient that a monoamine transporter present in the sample can transport the compound;
- c) washing the sample so as to remove any of the compound that has not been transported by the monoamine transporter;
- d) quantitating fluorescence of the sample;
- e) contacting the sample with a compound to be tested for activity as an inhibitor of the monoamine transporter;
- f) contacting the sample with the compound as used in step b) under the same conditions set forth in step b);
- g) washing the sample so as to remove any of the compound that has not been transported by the monoamine transporter; and
- h) quantitating fluorescence of the sample,
  wherein no change in, or a decrease in, the fluorescence of the sample quantitated in step h) compared to step d) indicates that the test compound is an inhibitor of the monoamine transporter.

In an embodiment, wherein the sample is mammalian nervous tissue, a vesicular fraction of mammalian nervous tissue, a synaptic fraction of mammalian nervous tissue, an endocrine or a neuroendocrine tissue. In an embodiment, wherein the monoamine transporter is a vesicular monoamine transporter. In an embodiment, the compound used in steps b) and f) has the structure:

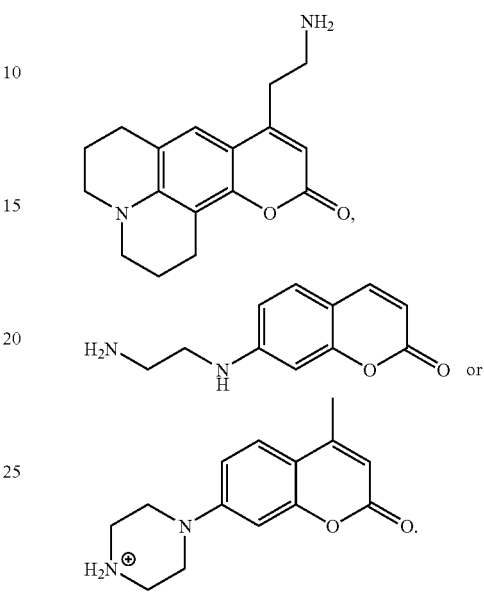

In an embodiment, the monoamine transporter is a dopamine transporter, norepinephrine transporter or a serotonin transporter. In an embodiment, the monoamine transporter is a dopamine transporter and the compound used in steps b) and f) has the structure:

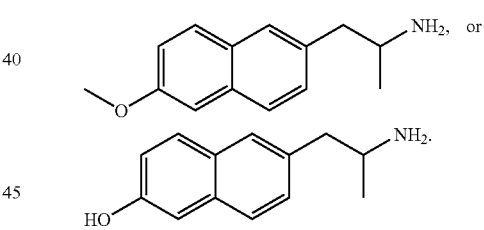

In an embodiment, the method further comprises recovering the compound identified as an inhibitor of the monoamine transporter.

This invention provides a process of identifying a compound which is an enhancer of a monoamine transporter comprising:
- a) providing a sample comprising a monoamine transporter in a medium;
- b) contacting the sample with the instant compound for a time sufficient that a monoamine transporter present in the sample can transport the compound;
- c) washing the sample so as to remove any of the compound that has not been transported by the monoamine transporter;
- d) quantitating fluorescence of the sample;
- e) contacting the sample with a compound to be tested for activity as an enhancer of the monoamine transporter;
- f) contacting the sample with the compound as used in step b) under the same conditions set forth in step b);

g) washing the sample so as to remove any of the compound that has not been transported by the monoamine transporter; and h) quantitating fluorescence of the sample.

wherein an increase in the fluorescence of the sample quantitated in step h) compared to step d) indicates that the test compound is an enhancer of the monoamine transporter.

In an embodiment, the sample is mammalian nervous tissue, a vesicular fraction of mammalian nervous tissue, a synaptic fraction of mammalian nervous tissue an endocrine or a neuroendocrine tissue. In an embodiment, the monoamine transporter is a vesicular monoamine transporter. In an embodiment, the compound used in steps b) and f) has the structure:

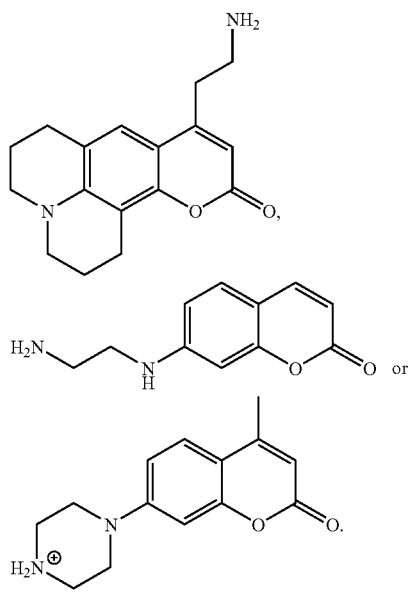

In an embodiment, the monoamine transporter is a dopamine transporter or a serotonin transporter. In an embodiment, the monoamine transporter is a dopamine transporter and the compound used in steps b) and f) has the structure:

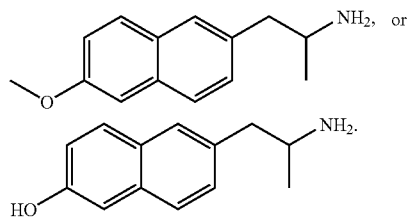

In an embodiment, the method further comprises recovering the compound identified as an enhancer of the monoamine transporter.

This invention provides a method for detecting an active monoamine transporter in a tissue of a subject in vivo comprising:

a) quantitating fluorescence of the tissue;

b) administering to the subject the instant compound so as to contact the tissue with the compound for a time sufficient that an active monoamine transporter present in the tissue can transport the compound; and c) quantitating fluorescence of the tissue, wherein an increase in the fluorescence of the sample quantitated in step c) over the fluorescence quantitated in step a) indicates the presence of an active monoamine transporter in the tissue of the subject.

This invention provides a method for monitoring the activity of a monoamine transporter in a tissue of a subject in vivo comprising:

a) administering to the subject the instant compound so as to contact the tissue with the compound for a time sufficient that an active monoamine transporter present in the tissue can transport the compound; and b) quantitating fluorescence of the tissue at a first point in time and then quantitating fluorescence of the tissue at a second and subsequent point in time, wherein the fluorescence of the tissue quantitated at the first point in time indicates the activity of the monoamine transporter at that point in time, and the fluorescence of the tissue quantitated at the second and subsequent point in time indicates the activity of the monoamine transporter at that point in time, thereby monitoring the activity of the monoamine transporter.

In an embodiment, the method further comprises the step of quantitating fluorescence of the tissue at a $n^{th}$ point in time subsequent to quantitating fluorescence of the tissue at a $n-1^{th}$ time, wherein n is a positive integer.

In an embodiment, the tissue is mammalian nervous tissue, an endocrine tissue or a neuroendocrine tissue. In an embodiment, the monoamine transporter is a vesicular monoamine transporter. In an embodiment, the compound used in step b) has the structure:

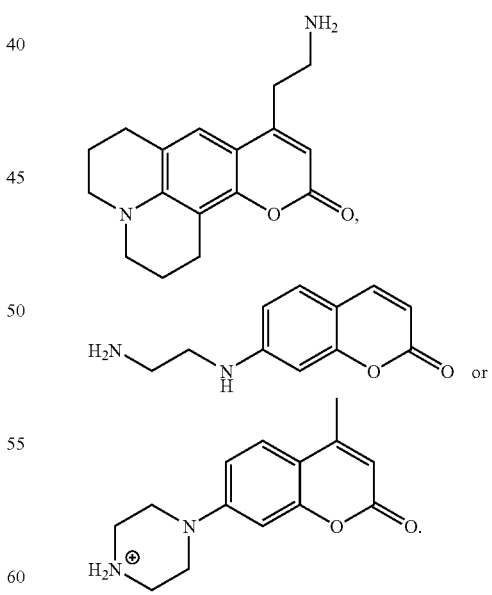

In an embodiment, the active monoamine transporter is a dopamine transporter, a norepinephrine transporter or a serotonin transporter. In an embodiment active monoamine transporter is a dopamine transporter and compound used in step b) has the structure:

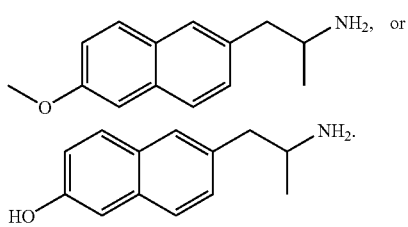

This invention provides a method of diagnosing a disease in a patient, wherein a symptom of the disease is impaired monoamine transporter activity in a tissue of the patient comprising:
  a) contacting the tissue with the instant compound for a time sufficient that a monoamine transporter present in the tissue can uptake the compound;
  b) quantitating fluorescence or rate of change of fluorescence of the tissue; and
  c) comparing the fluorescence or rate of change of fluorescence of the tissue with a reference standard,
  wherein a lower fluorescence or rate of change of fluorescence of the tissue as compared with the reference standard indicates impaired monoamine transporter activity and the presence of the disease in the subject.

A higher fluorescence or rate of change of fluorescence of the tissue as compared with the reference standard indicates enhanced monoamine transport.

In an embodiment, the tissue is in situ or in vitro. In an embodiment, the tissue is mammalian nervous system tissue. In an embodiment, the monoamine transporter is a dopamine transporter or a vesicular monoamine transporter and the disease is Parkinson's, Wilson's, or Lesch-Nyhan's disease. In an embodiment the disease is epilepsy, schizophrenia or restless legs syndrome. In an embodiment, the monoamine transporter is a serotonin transporter or a vesicular monoamine transporter and the disease is depression or aggressive behavior. In an embodiment the transporter is a norepinephrine transporter.

This invention provides a pharmaceutical composition comprising any embodiment or combination thereof of the instant compound and a pharmaceutically acceptable carrier.

This invention provides a kit for detecting monoamine transporter activity in a biological sample comprising any embodiment or combination thereof of the instant compound and instructions for use. This invention provides a kit for monitoring neurotransmission comprising any embodiment or combination thereof of the instant compound and instructions for use.

This invention provides a method of identifying a compound as an inhibitor of a monoamine transporter comprising:
  a) contacting a sample comprising a monoamine transporter with a compound of any one of the instant compounds for a time sufficient that a monoamine transporter present in the sample can transport the compound;
  b) washing the sample so as to remove any of the compound that has not been transported by the monoamine transporter;
  c) quantitating fluorescence of the sample;
  d) contacting the sample with a compound to be tested for activity as an inhibitor of the monoamine transporter;
  e) contacting the sample with the compound as used in step a) under the same conditions set forth in step a);
  f) washing the sample so as to remove any of the compound that has not been transported by the monoamine transporter; and
  g) quantitating fluorescence of the sample, wherein no change in, or a decrease in, the fluorescence of the sample quantitated in step g) compared to step c) indicates that the test compound is an inhibitor of the monoamine transporter.

In an embodiment, the method identifies a compound as an inhibitor of a monoamine transporter useful in the treatment of Parkinson's disease, epilepsy, schizophrenia, depression or restless legs syndrome.

This invention provides a method of treating a neurological disease in a subject, wherein the neurological disease is characterized by reduced neurotransmitter release, comprising administering to the subject a therapeutically effective amount of the compound of any one of the instant compounds.

In an embodiment, the disease is Parkinson's disease. In an embodiment, the neurotransmitter is dopamine, serotonin or norepinephrine. This invention provides a method of activating a receptor comprising contacting the receptor with the compound of any one of the instant compounds.

This invention provides a method of inhibiting a receptor comprising contacting the receptor with the compound of any one of the instant compounds.

In embodiments of the methods the receptor is a dopamine receptor, a serotonin receptor, a norepinephrine receptor or a histamine receptor.

This invention provides a method of determining the efficaciousness of a therapy in altering neurotransmitter activity in the treatment of a neurological disease in a subject comprising:
  a) administering to the subject the compound of any one of the instant compounds;
  b) determining neurotransmitter activity at a site in the subject by measuring the release or uptake of the compound at the site;
  c) treating the subject with the therapy;
  d) administering to the subject the compound of as administered in step a); and
  e) determining neurotransmitter activity at a site in the subject by measuring the release or uptake of the compound at the site,
  wherein a change in the release or uptake of neurotransmitter as measured in step e) compared to that measured in step b) indicates that the therapy is efficacious.

In an embodiment the therapy increases neurotransmitter release. In an embodiment the therapy decreases neurotransmitter release. In an embodiment the therapy increases neurotransmitter uptake. In an embodiment the therapy decreases neurotransmitter uptake. In an embodiment the neurotransmitter is dopamine. In an embodiment the neurotransmitter is serotonin. In an embodiment the release or uptake of the compound is determined by fluorescence microscopy.

This invention provides a method of determining if neurotransmitter is released from a vesicle or synapse comprising:
  a) contacting the vesicle or synapse with a compound of any one of the instant compounds for a time sufficient for the compound to be taken up into the vesicle or synapse;
  b) detecting fluorescence of the compound in the vesicle or synapse;
  c) subjecting the vesicle or synapse to a stimulus known to cause neurotransmitter release; and
  d) detecting fluorescence of the compound in the vesicle or synapse, wherein a decrease in the fluorescence detected in step d) as compared to the fluorescence measured in step b) indicates that the neurotransmitter is released from the vesicle or synapse.

In an embodiment the vesicle is a pre-synaptic vesicle. In an embodiment the vesicle is a large dense core vesicle. In an embodiment the stimulus is an exogenous or endogenous electrical stimulus. In an embodiment the stimulus is neuronal firing. In an embodiment the stimulus is a chemical stimulus. In an embodiment the stimulus is a neurotransmitter stimulus. In an embodiment the vesicle is in a neuron. In an embodiment the synapse is in a brain tissue. In an embodiment the brain tissue is a slice of brain tissue in vitro.

This invention provides a method of determining if neurotransmitter is transported into a synapse or vesicle comprising:
   a) contacting the vesicle or synapse with a compound of any one of the instant compounds for a time sufficient for the compound to be taken up into the vesicle or synapse;
   b) detecting fluorescence of the compound in the vesicle or synapse;
   wherein an increase in the fluorescence detected in the vesicle or synapse indicates that the neurotransmitter is transported into the synapse or vesicle.

In an embodiment of the methods described herein the VMAT is a VMAT1. In an embodiment of the methods described herein the VMAT is a VMAT2.

As used herein, an "increase in fluorescence" of a compound means an increase in the measured level of fluorescence of the compound when the compound is excited with light of a predetermined excitation wavelength(s), or more specifically the emission intensity is directly proportional to brightness. In this case, brightness=$(\epsilon)(\Phi)$, where $\epsilon$ is the extinction coefficient at which the quantum yield is measured and $\Phi$ is the quantum yield.

As used herein, "reference standard" means a normalized value obtained form a standardized sample, and in the case of fluorescence means the normalized fluorescence measured from a sample obtained from a subject without a monoamine transporter deficiency (e.g. VMAT, DAT, SERT or NET) or without impaired monoamine transporter activity, or other standardized sample, as measured by a parallel assay with the same steps and conditions to which the tested sample is being subjected.

As used herein "physiological medium" means any natural or artificially synthesized medium recognizable by one of ordinary skill in the art as supporting monoamine transport activity in the presence of a monoamine. Examples of such include interstitial fluid, cerebrospinal fluid, and phosphate buffered saline.

VMAT as used herein, unless otherwise specified, refers to all VMAT forms, e.g. VMAT1 and VMAT2.

As used herein, a "competitive substrate" in relation to a monoamine transporter is a substance capable of binding to the monoamine transporter's active site in place of the physiological substrate and being transported.

As used herein, a "competitive inhibitor" in relation to a monoamine transporter is a substance capable of binding to the monoamine transporter's active site in place of the physiological substrate but not transported.

As used herein, "diagnosing" a monoamine transporter (e.g. VMAT, DAT, SERT or NET) deficiency or a disease associated with such, means identifying a cell, a tissue, or a sample as having impaired monoamine transporter activity below the level of activity of that monoamine transporter in a non-pathological or non-diseased cell, tissue or sample. Characteristics of psychiatric disease states associated with impaired monoamine transport are described in Diagnostic and Statistical Manual of Mental Disorders DSM-IV-TR Fourth Edition by the American Psychiatric Association, American Psychiatric Publishing, 4th edition (June 2000), herein incorporated by reference.

As used herein "neurotransmitter release" shall mean the release, e.g. by exocytosis, of a neurotransmitter from a synaptic vesicle into, for example, a synaptic cleft.

As used herein "neurotransmitter uptake" shall mean the uptake of a neurotransmitter from, for example, a synaptic cleft into a pre- or post-synaptic terminal (i.e. includes what is termed re-uptake), a glial cell, or any cell comprising a monoamine transporter; or the uptake of a neurotransmitter into a synaptic vesicle.

The methods of the present invention when pertaining to cells, and samples derived or purified therefrom, including monoamine transporter containing fractions, may be performed in vitro. The methods of diagnosis may, in different embodiments, be performed in vivo, in situ, or in vitro. The methods of diagnosis may be performed on human, or non-human mammalian subjects.

The various probes described herein may be monoamine transporter competitive substrates or inhibitors, and may be antagonists or agonists of the monoamine receptors. For example, the probes disclosed herein may serotoninmimetic or dopamimetic.

A "sample" as used herein means a biological material including, but not limited to, a liquid, coma, a cell, a tissue (including blood), or a derivative thereof including, but not limited to, a fraction, a centrifugate, a cellular component, a tissue slice, or a disaggregated tissue, each expected to contain a monoamine transporter.

Such a sample may be removed from a subject, or if stated, maybe in situ.

"Mammalian nervous tissue" includes peripheral and central nervous tissue. Examples of nerves tissue include but are not limited to disaggregated cells, cultured cells and slices of tissue such as hippocampal or substantia nigral.

Fluorescence may be quantitated with any of the many devices known to those of ordinary skill in the art, including, but not limited to photomultipliers, photometers, fluorimeters, CCD-based cameras or optic fiber systems and using fluorescent microscopy. Alternatively, fluorescence may be quantitated by the naked eye with or without the use of a microscope system. Fluorescence may be quantitated in arbitrary units.

Salts and stereoisomers, including enantiomers, of the probes disclosed herein are within the scope of the invention.

The compounds as set forth herein can be methylated at the α-position of the amine. Such methylated compounds are encompassed within the scope of the invention.

Probes in the form of an ion co-exist with suitable counter-ions. For example, in an embodiment, probes 38 and 484 can each co-exist with $CF_3COO^-$.

In an embodiment, the piperazine cation has the structure:

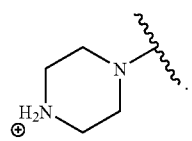

As used herein, a "salt" is salt of the instant compounds which has been modified by making acid or base salts of the compounds. The salt can be pharmaceutically acceptable.

Examples of pharmaceutically acceptable salts include, but are not limited to, mineral or organic acid salts of basic residues such as amines; alkali or organic salts of acidic residues such as carboxcylic acids. The salts can be made using an organic or inorganic acid. Such acid salts are chlorides, bromides, sulfates, nitrates, phosphates, sulfonates, formates, tartrates, maleates, malates, citrates, benzoates, salicylates, ascorbates, and the like. Carboxylate salts are the alkaline earth metal salts, sodium, potassium or lithium.

As used herein, "alkyl" is intended to include both branched and straight-chain saturated aliphatic hydrocarbon groups having the specified number of carbon atoms. Thus, $C_1$-$C_n$ as in "$C_1$-$C_n$ alkyl" is defined to include groups having 1, 2, . . . , or n carbons in a linear or branched arrangement, and specifically includes methyl, ethyl, propyl, butyl, pentyl, hexyl, and so on. For example, $C_1$-$C_6$, as in "$C_1$-$C_6$ alkyl" is defined to include individual moieties having 1, 2, 3, 4, 5, or 6 carbons in a linear or branched arrangement. "Alkoxy" represents an alkyl moiety of indicated number of carbon atoms which is attached to the core through an oxygen bridge.

The term "cycloalkyl" shall mean cyclic rings of alkanes of three to eight total carbon atoms, or any number within this range (i.e., cyclopropyl, cyclobutyl, cyclopentyl, cyclohexyl, cycloheptyl or cyclooctyl).

If no number of carbon atoms is specified, the term "alkenyl" refers to a non-aromatic hydrocarbon radical, straight or branched, containing at least 1 carbon to carbon double bond, and up to the maximum possible number of non-aromatic carbon-carbon double bonds may be present. If the number of carbon atoms is specified, e.g. "$C_2$-$C_n$" alkenyl, each member of the numeric range is disclosed individually as discussed above. Thus, for example, "$C_2$-$C_6$ alkenyl" means an alkenyl radical having 2, 3, 4, 5, or 6 carbon atoms, and up to 1, 2, 3, 4, or 5 carbon-carbon double bonds respectively. Alkenyl groups include ethenyl, propenyl, butenyl and cyclohexenyl.

The term "cycloalkenyl" shall mean cyclic rings of 3 to 10 carbon atoms and at least 1 carbon to carbon double bond (i.e., cyclopropenyl, cyclobutenyl, cyclopenentyl, cyclohexenyl, cycloheptenyl or cycloocentyl).

The term "alkynyl" refers to a hydrocarbon radical straight or branched, containing at least 1 carbon to carbon triple bond, and up to the maximum possible number of non-aromatic carbon-carbon triple bonds may be present. Thus, "$C_2$—$C_6$ alkynyl" means an alkynyl radical radical having 2, 3, 4, 5, or 6 carbon atoms, and for example 1 carbon-carbon triple bond, or having 4 or 5 carbon atoms, and up to 2 carbon-carbon triple bonds, or having 6 carbon atoms, and up to 3 carbon-carbon triple bonds. Alkynyl groups include ethynyl, propynyl and butynyl. As described above with respect to alkyl, the straight or branched portion of the alkynyl group may contain triple bonds and may be substituted if a substituted alkynyl group is indicated.

In differing embodiments of alkyl as used herein the alkyl is a C1-C10 alkyl. In differing embodiments of alkenyl as used herein the alkenyl is a C2-C10 alkenyl. In differing embodiments of alkynyl as used herein the alkenyl is a C2-C10 alkynyl.

The definitions of alkyl, alkenyl and alkynyl are applied mutatis mutandis to the terms alklyene, alkenylene and alkynylene, respectively.

In differing embodiments of alkylene as used herein the alkylene is a C1-C10 alkylene. In differing embodiments of alkenylene as used herein the alkenylene is a C2-C10 alkenylene. In differing embodiments of alkynylene as used herein the alkenylene is a C2-C10 alkynylene. When a range of numbers are given, e.g. 1-10 as in C1-C10, each individual integer member of the whole range is envisaged. Thus, C1-C10, includes C1, C2, C3, C4, C5, C6, C7, C8, C9 and C10, each an individual embodiment.

In one embodiment the alkylene is propylene (—$C_3H_6$—).

As used herein, "aryl" is intended to mean any stable monocyclic, bicyclic or tricyclic carbon ring of up to 10 atoms in each ring, wherein at least one ring is aromatic. Examples of such aryl elements include phenyl, naphthyl, tetrahydronaphthyl, indanyl, biphenyl, phenanthryl, anthryl or acenaphthyl In cases where the aryl substituent is bicyclic and one ring is non-aromatic, it is understood that attachment is via the aromatic ring.

The term "heteroaryl", as used herein, represents a stable monocyclic or bicyclic ring of up to 10 atoms in each ring, wherein at least one ring is aromatic and contains from 1 to 4 heteroatoms selected from the group consisting of O, N and S. Heteroaryl groups within the scope of this definition include but are not limited to: benzoimidazolyl, benzofuranyl, benzofurazanyl, benzopyrazolyl, benzotriazolyl, benzothiophenyl., benzoxazolyl, carbazolyl, carbolinyl, cinnolinyl, furanyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrazolyl, tetrazolopyridyl, thiadiazolyl, thiazolyl, thienyl, triazolyl, azetidinyl, aziridinyl, 1,4-dioxanyl, hexahydroazepinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, tetrahydrothienyl, acridinyl, carbazolyl, cinnolinyl, quinoxalinyl, pyrrazolyl, indolyl, benzotriazolyl, benzothiazolyl, benzoxazolyl, isoxazolyl, isothiazolyl, furanyl, thienyl, benzothienyl, benzofuranyl, quinolinyl, isoquinolinyl, oxazolyl, isoxazolyl, indolyl, pyrazinyl, pyridazinyl, pyridinyl, pyrimidinyl, pyrrolyl, tetra-hydroquinoline. In cases where the heteroaryl substituent is bicyclic and one ring is non-aromatic or contains no heteroatoms, it is understood that attachment is via the aromatic ring or via the heteroatom containing ring, respectively. If the heteroaryl contains nitrogen atoms, it is understood that the corresponding N-oxides thereof are also encompassed by this definition.

"Halo" or "halogen" as used herein is intended to include chloro, fluoro, bromo and iodo.

The term "heterocycle" or "heterocyclyl" as used herein is intended to mean a 5- to 10-membered nonaromatic ring containing from 1 to 4 heteroatoms selected from the group consisting of O, N and S, and includes bicyclic groups. "Heterocyclyl" therefore includes, but is not limited to the following: imidazolyl, piperazinyl, piperidinyl, pyrrolidinyl, morpholinyl, thiomorpholinyl, tetrahydropyranyl, dihydropiperidinyl, tetrahydrothiophenyl and the like. If the heterocycle contains a nitrogen, it is understood that the corresponding N-oxides thereof are also encompassed by this definition.

The alkyl, alkenyl, alkynyl, cycloalkyl, aryl, heteroaryl and heterocyclyl substituents may be substituted or unsubstituted, unless specifically defined otherwise. For example, a (C1-C7) alkyl may be substituted with one or more substituents selected from OH, oxo, halogen, alkoxy, dialkylamino, or heterocyclyl, such as morpholinyl, piperidinyl, and so on. In the compounds of the present invention, alkyl, alkenyl, alkynyl, cycloalkyl, cycloalkenyl, heterocyclyl and heteroaryl groups can be further substituted by replacing one or more hydrogen atoms by alternative non-hydrogen groups. These include, but are not limited to, halo, hydroxy, mercapto, amino, carboxy, cyano and carbamoyl.

The term "substituted" shall be deemed to include multiple degrees of substitution by a named substitutent. Where multiple substituent moieties are disclosed or claimed, the substituted compound can be independently substituted by one or more of the disclosed or claimed substituent moieties, singly or plurally. By independently substituted, it is meant that the (two or more) substituents can be the same or different.

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results.

In embodiments of this invention, unsubstituted substituted aromatic rings include six-membered rings. In an embodiment the ring is substituted by a C1-C10 alkyl, alkenyl or alkynyl, each of which may be linear or branched, and each of which may be substituted themselves with one or more amino groups. In an embodiment the substituted pyrroles groups of this invention are substituted by a C1-C10 alkyl, alkenyl or alkynyl, each of which may be linear or branched, and each of which may be substituted themselves with one or more amino groups. In one embodiment the pyrrole group is substituted with an aminoethyl group.

In an embodiment the alkyl, alkenyl or alkynyl, alkylene, alkenylene or alkynlene groups of this invention have 1, 2, 3, 4, 5, 6, 7, 8, 9 or 10 carbon atoms.

In choosing compounds of the present invention, one of ordinary skill in the art will recognize that the various substituents, i.e. $R^1$, $R^2$, and $R^3$, are to be chosen in conformity with well-known principles of chemical structure connectivity.

All combinations of the various elements disclosed herein are within the scope of the invention.

This invention will be better understood by reference to the Experimental Details which follow, but those skilled in the art will readily appreciate that the specific experiments detailed are only illustrative of the invention as described more fully in the claims which follow thereafter.

EXPERIMENTAL DETAILS

Example 1

Current efforts to advance the understanding of neurotransmission and synaptic plasticity are limited by available experimental approaches that either lack spatial resolution of individual synaptic terminals or provide no information about presynaptic processes controlling vesicular neurotransmitter filling and release—issues that are particularly important for dopamine and other monoamine neurotransmission. We describe a novel optical approach based on fluorescent false neurotransmitters (FFNs) that act as optical tracers, providing the first means to directly visualize neurotransmitter uptake, redistribution, and release from individual dopamine terminals. FFNs were designed by targeting the synaptic vesicular monoamine transporter (VMAT) that transports dopamine and other aminergic neurotransmitters from cytoplasm into synaptic vesicles. Like dopamine, exemplified FFN probe 511 selectively accumulates in chromaffin cell granules and dopamine terminals in the mouse striatum, in a manner dependent on VMAT function and the vesicular pH gradient, and is released upon synaptic firing. Using 511, it is possible to directly measure the fraction of vesicular neurotransmitter released and remaining with the synaptic terminals per stimulus, parameters of vast fundamental interest in neuroscience.

Elucidating the synaptic basis of complex phenomena such as memory, learning, and behavior represents one of the frontier areas in neuroscience. New experimental approaches are required to study presynaptic processes—including vesicle filling, content redistribution, and release—that regulate neurotransmission and contribute to synaptic plasticity. This is particularly relevant to dopamine (DA) and other monoamine neurotransmitters which do not elicit ionotropic post-synaptic currents and are thus poorly resolved by post-synaptic recordings. Synaptic DA release is modulated by numerous mechanisms, including the regulation of quantal size, the probability of synaptic vesicle fusion, and possibly the alteration of the fusion mode between full fusion or kiss-and-run fusion (40). These are in turn regulated by neuronal activity and the level of ongoing activation of auto- and heteroreceptors on the presynaptic terminals. Aberration in presynaptic dopamine stores and release underlie Parkinson's disease as well as important aspects of psychiatric disorders including ADHD, drug addiction, and schizophrenic and amphetamine-triggered psychosis (39).

Current approaches for direct measurement of monoamine release rely on microdialysis and electrochemical methods. Although electrochemical detection of DA release with cyclic voltammetry and amperometry has provided excellent temporal resolution (38, these methods provide poor spatial resolution in brain tissue as they sample release and uptake of hundreds to thousands of DA terminals.

Optical methods, on the other hand, enable monitoring the activity of single synaptic terminals. This is presently achieved with endocytic FM dyes (27) that visualize membrane fusion of recycling synaptic vesicles or synaptopHlorins (28), which are membrane-bound pH sensitive GFP indicators that report on pH shifts of the lumen following vesicle fusion. Notably, both of these methods indicate fusion of synaptic vesicle with the plasma membrane but not the release of vesicular neurotransmitter. Indeed, it has been shown that under some conditions "empty" catecholamine vesicles can fuse with no release of dopamine (29)(30). Thus, while very useful tools for studying vesicle membrane fusion, these approaches provide no direct information about vesicle content and its release, and as such are inadequate for examination of important presynaptic mechanisms modulating neurotransmission of DA and other monoamine neurotransmitters.

Disclosed herein is the design of optical tracers of monoamine neurotransmitters or Fluorescent False Neurotransmitters (FFNs). Classical papers that demonstrated that tyramine and other phenylethylamines were taken up into synaptic vesicles and discharged by exocytosis upon stimulation (31) were relevant to this approach. If these so called false neurotransmitters are designed to be fluorescent, they could serve to directly monitor synaptic function by tracing the endogenous neurotransmitters.

To generate fluorescent probes for selective loading of, for example, dopamine and serotonin vesicles, design was guided by the key structural and physical chemical properties of the natural neurotransmitters. The aminoethyl group (which represents the crucial recognition element for VMAT)

and the polar group on the aromatic system are both present in various structural orientations. See FIG. 2 and (10).

The probes need to be mildly basic to provide the driving force for accumulation in the vesicle and highly polar to prevent passive transport to other acidic compartments such as endosomes, whose membranes do not contain VMAT (5 and 11).

One design route for FFNs is through targeting vesicular monoamine transporter 2 (VMAT2), the key protein that transports monoamine—neurotransmitters from the cytoplasm into synaptic vesicles (32). The driving force for the transport and for achieving high intravesicular concentrations of neurotransmitter is provided by the proton gradient between the synaptic vesicle interior and the cytosol. VMAT2 is not specific; it transports not only different endogenous monoamines (e.g., dopamine, serotonin, norepinephrine, beta-phenethylamine, tyramine, and histamine) but also exogenous synthetic amines (e.g. amphetamine, MDMA) (33). Furthermore, the neurotoxin MPP+ (1-methyl-4-phenyl-pyridium salt), although structurally significantly different from phenethylamines, is also a good VMAT substrate (34). The substantial functional plasticity of VMAT2 was taken as a suggestion that bulkier fluorescent monoamines might also be recognized as substrates.

Figure 2:
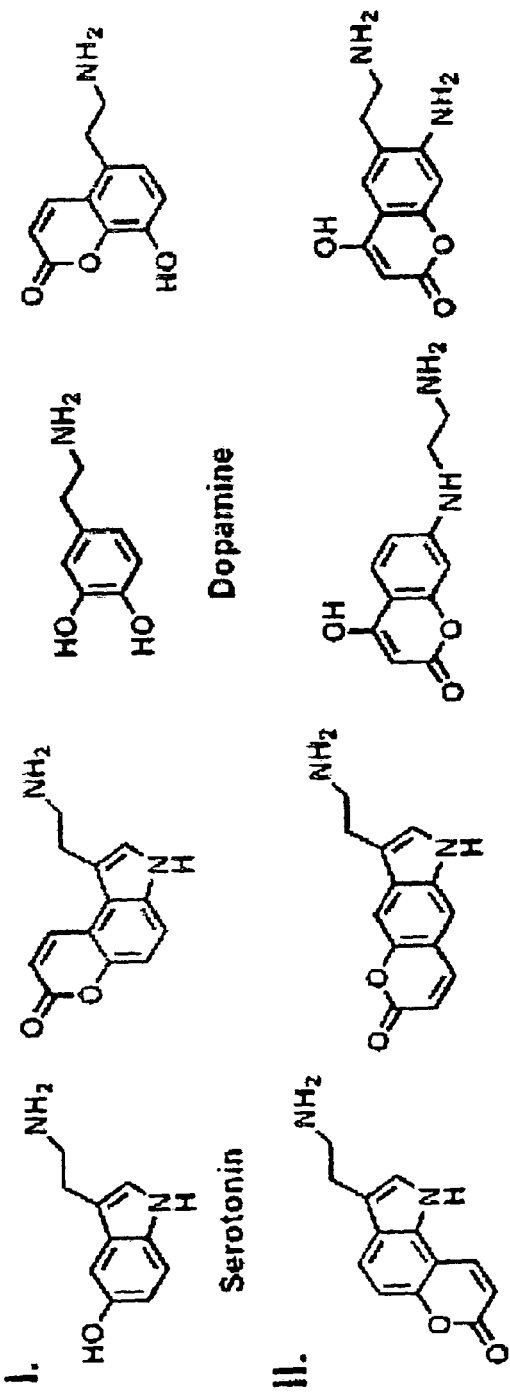
FIG. 2: Fluorescent serotonin and dopamine derivatives.
Figure 12:
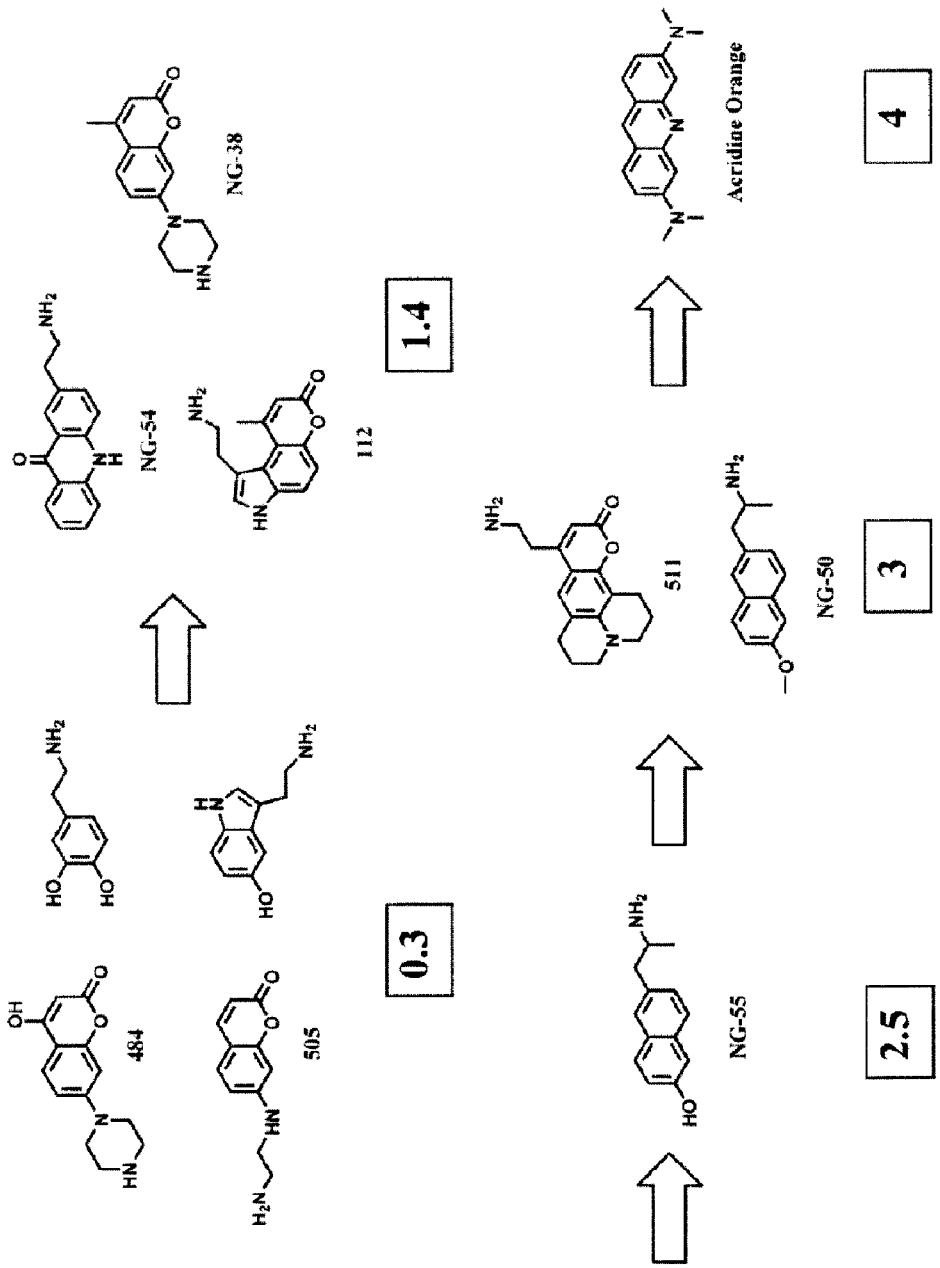
FIG. 12: Estimated polarity of probes and substrates. The synthesized probes are estimated to be as polar as the endogenous substrates (polarity of 0.3) or more polar. (Polarity values estimated using software from the Syracuse Research Corporation).
Figure 13:
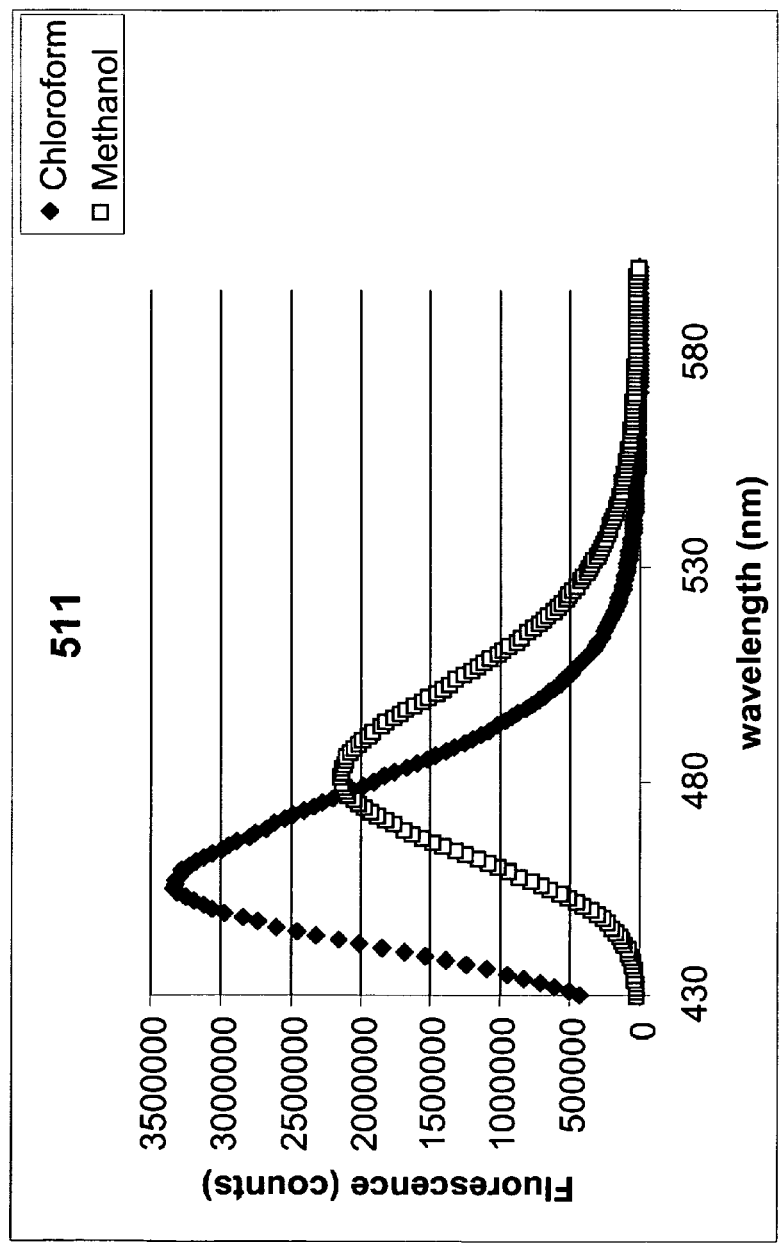
FIG. 13: Fluorescence spectra for probe 511 as measured in chloroform and methanol.
Figure 14:
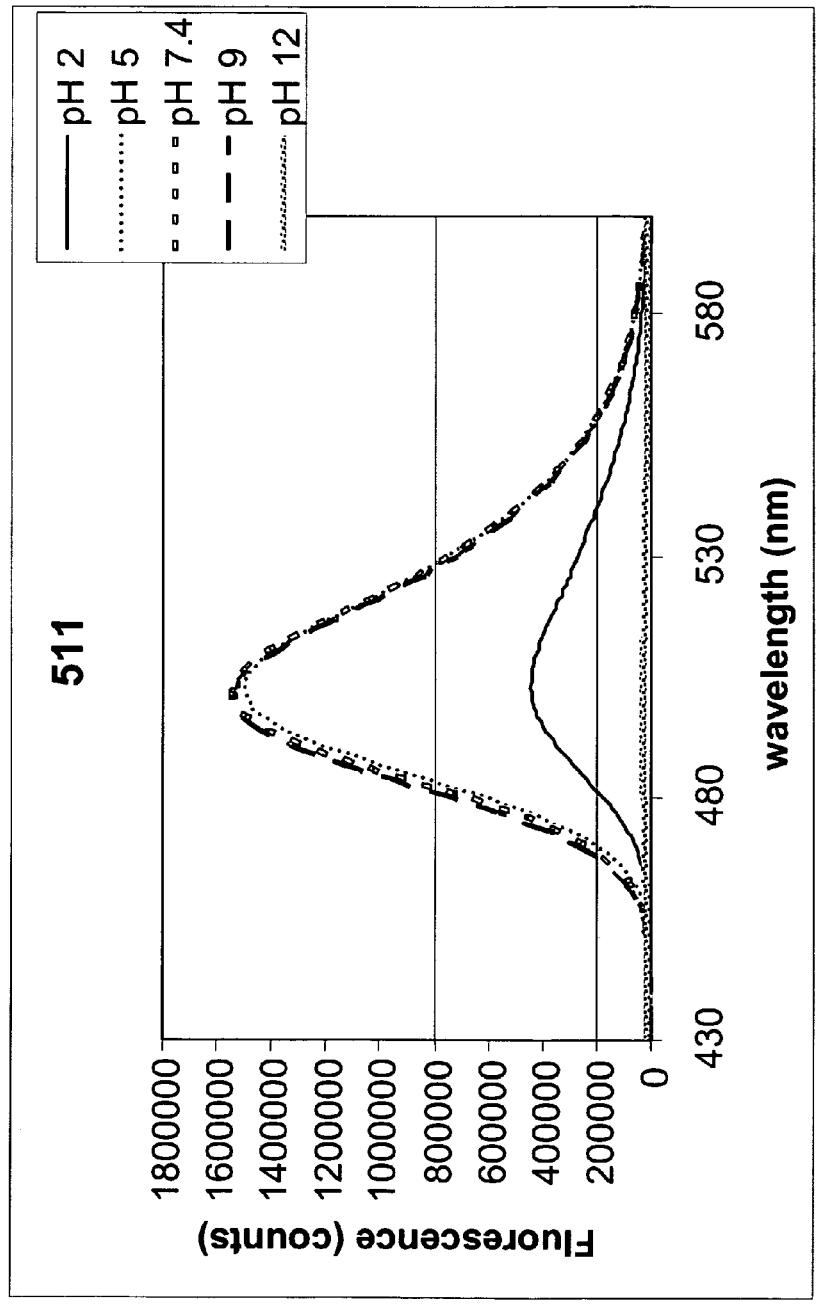
FIG. 14: pH dependency of fluorescence spectra of probe 511. Spectra measured at pH 2, 5, 7.4, 9 and 12, with increased fluorescence seen at alkaline pH values.
Figure 15:
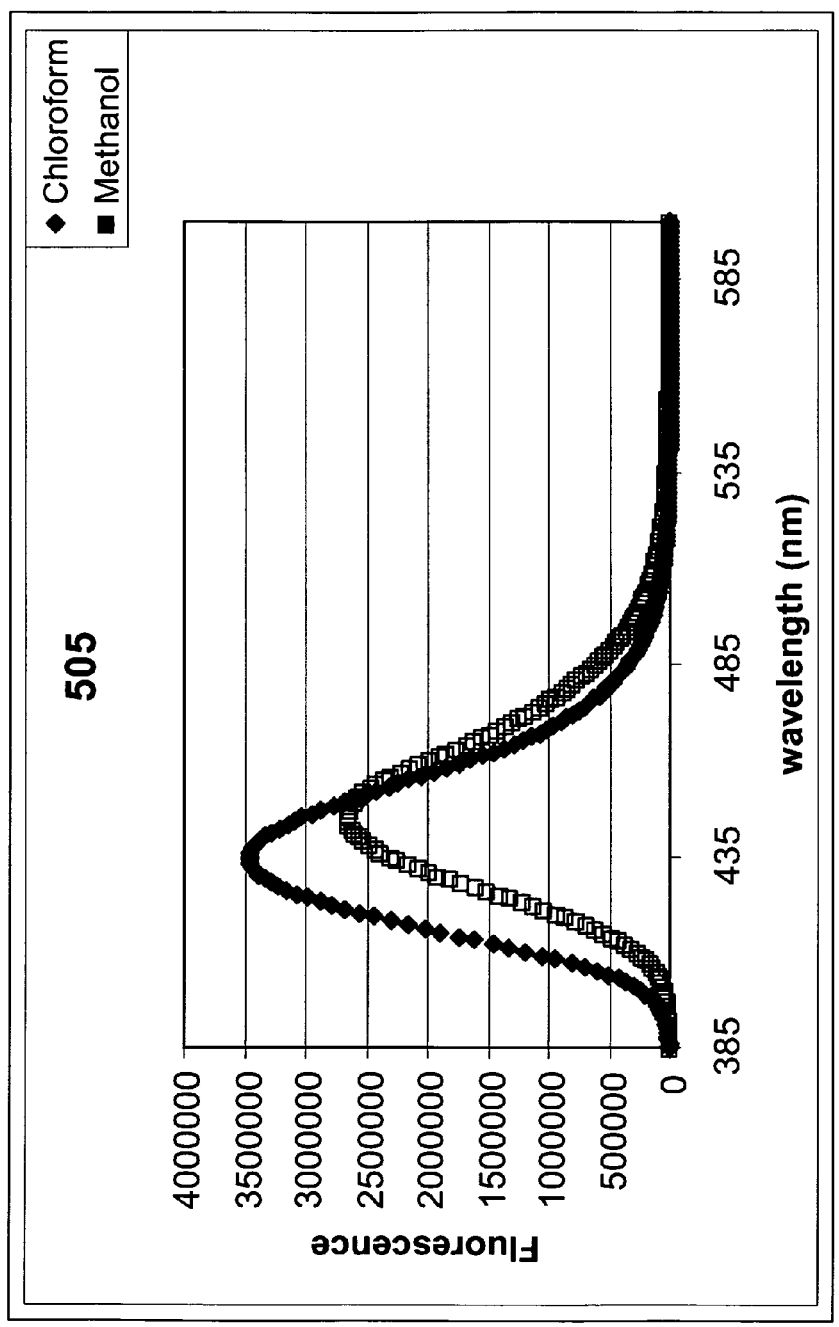
FIG. 15: Fluorescence spectra for probe 505 as measured in chloroform and methanol.
Figure 16:
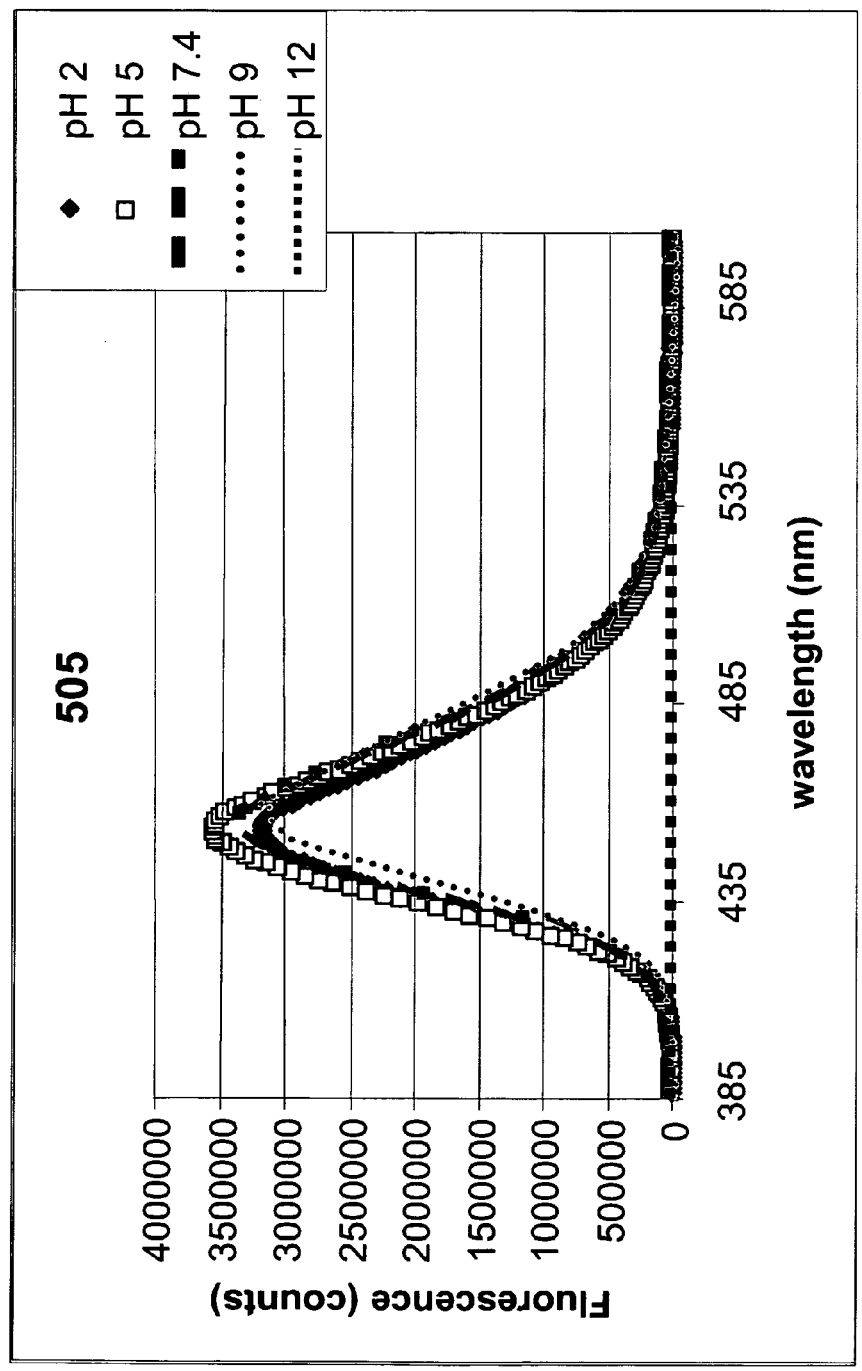
FIG. 16: pH dependency of fluorescence spectra for probe 505. Spectra measured at pH 2, 5, 7.4, 9 and 12.
Figure 17:
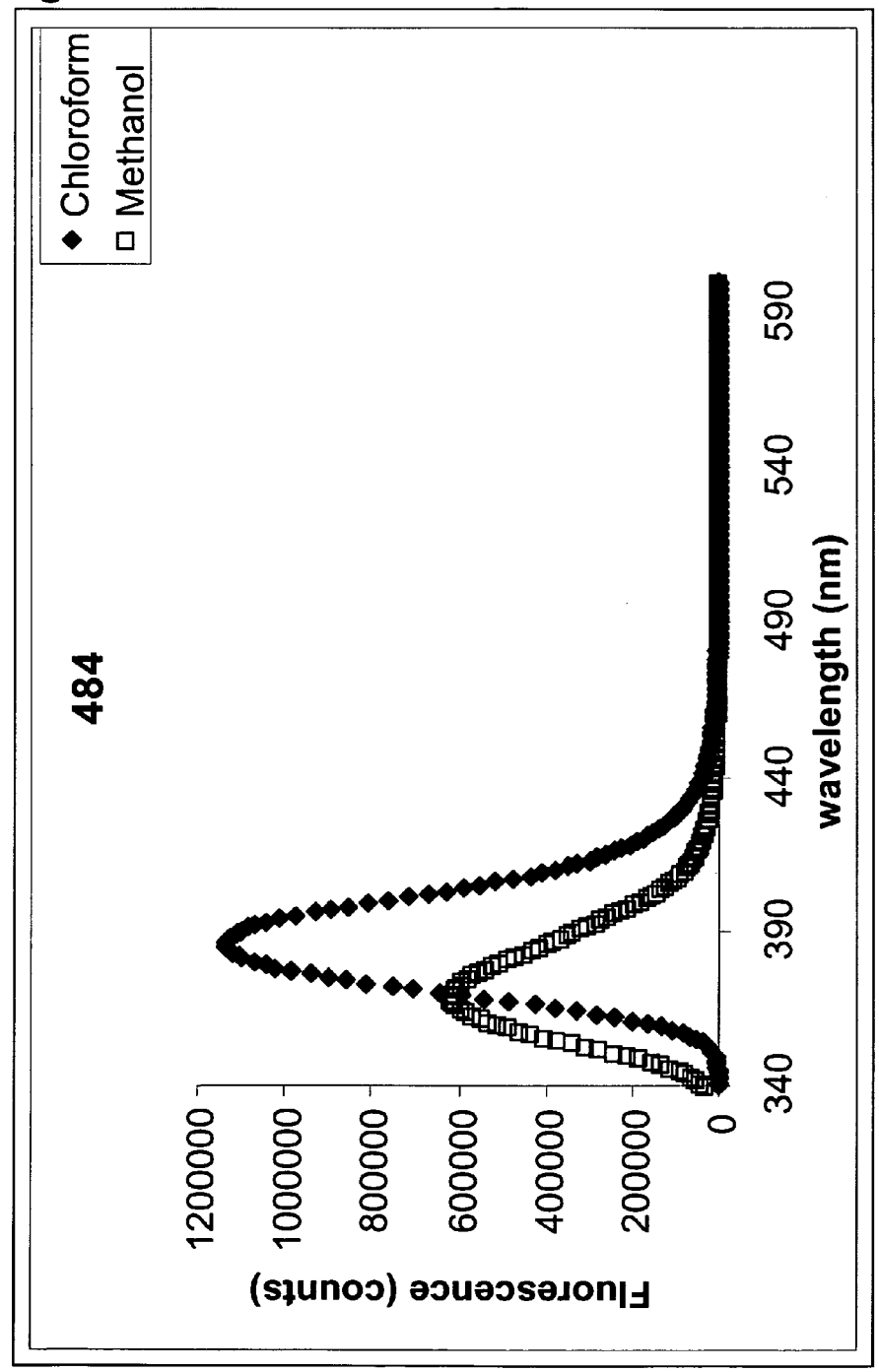
FIG. 17: Fluorescence spectra for Probe 484 as measured in chloroform and methanol.

Probes resembling serotonin (class I) and dopamine (class II), see FIG. 2, were synthesized, and the probes evaluated in terms of the physical and photophysical properties. The polarity is judged by the partition coefficient—a standard measure of a compound's polarity and a good indicator of membrane permeability. See FIG. 12. If necessary the coumarin moiety is substituted with additional hydroxy groups to match the probes' polarity with that of the natural neurotransmitters.

Figure 6:
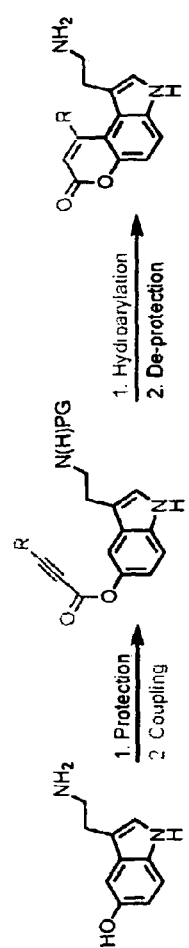
FIG. 6: Synthesis of a coumarin-based probe by hydroarylation of an aryl C—H bond across a point of unsaturation.

Serotonin analogs can be synthesized by hydroarylation of the appended alkyne (21, 22). In order to carry out such a transformation the substrate to be modified must possess a phenolic handle, which can be esterified with a propargyllic acid via known peptide coupling procedures (FIG. 6). The resulting tethered alkyne can then be inserted into the aryl C—H bond using an electrophilic metal catalyst such as $PtCl_2$ or $PtCl_4$, to result in the fluorescent coumarin moiety. It is likely that any free amines, such as the ethylamine present in serotonin, will require protection in order to prevent them from binding the catalyst.

Figure 7:
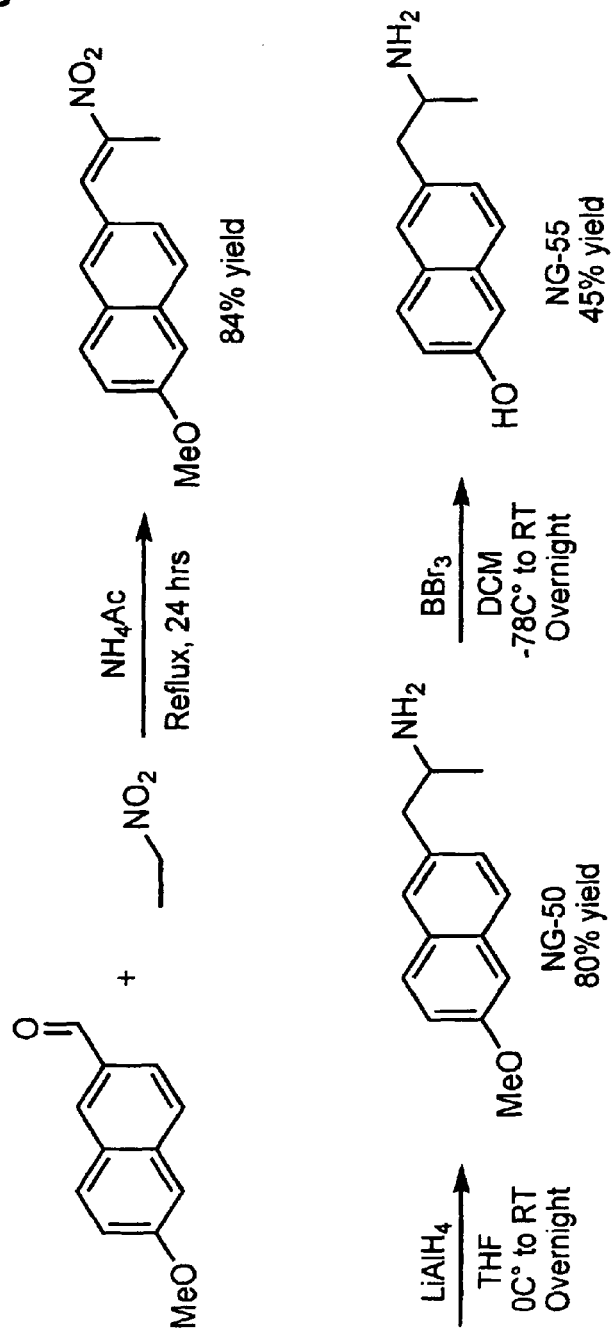
FIG. 7: Synthesis of naphthalene-based probe 50 which can be demethylated to probe 55.
Figure 8:
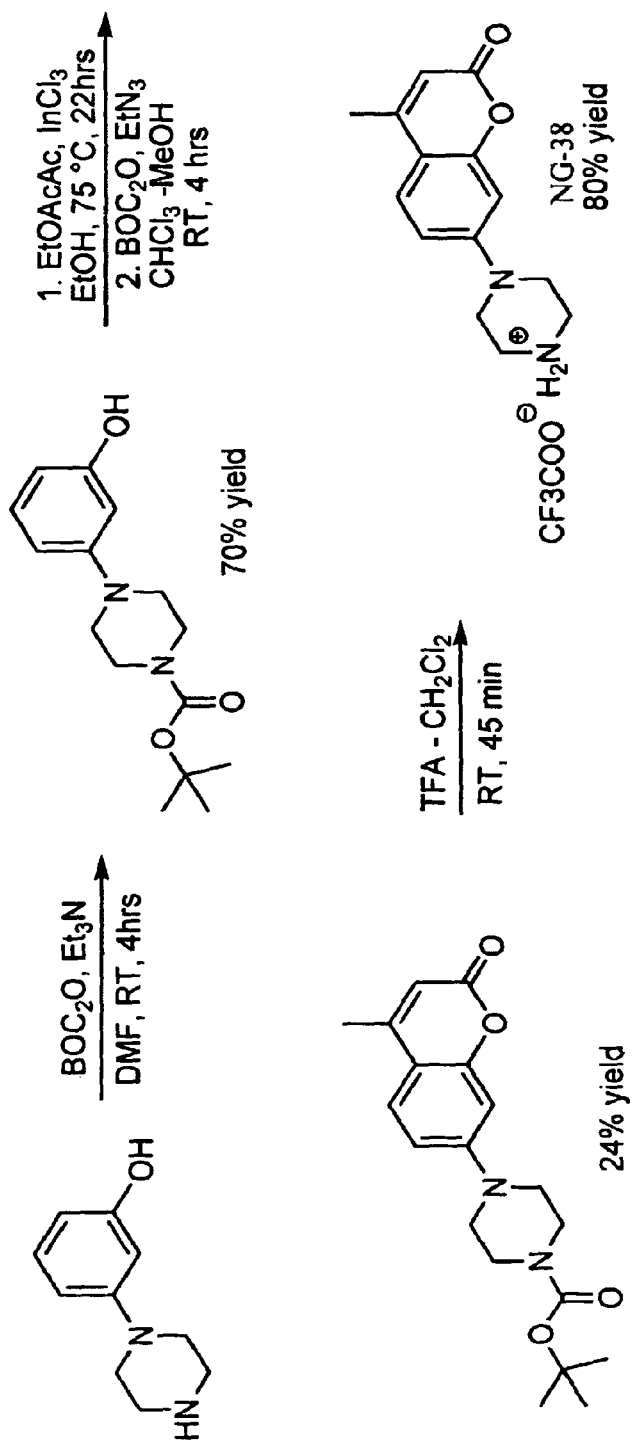
FIG. 8: Synthesis of coumarin-based probes using a di-tert-butyl pyrocarbonate protecting group.
Figure 9:
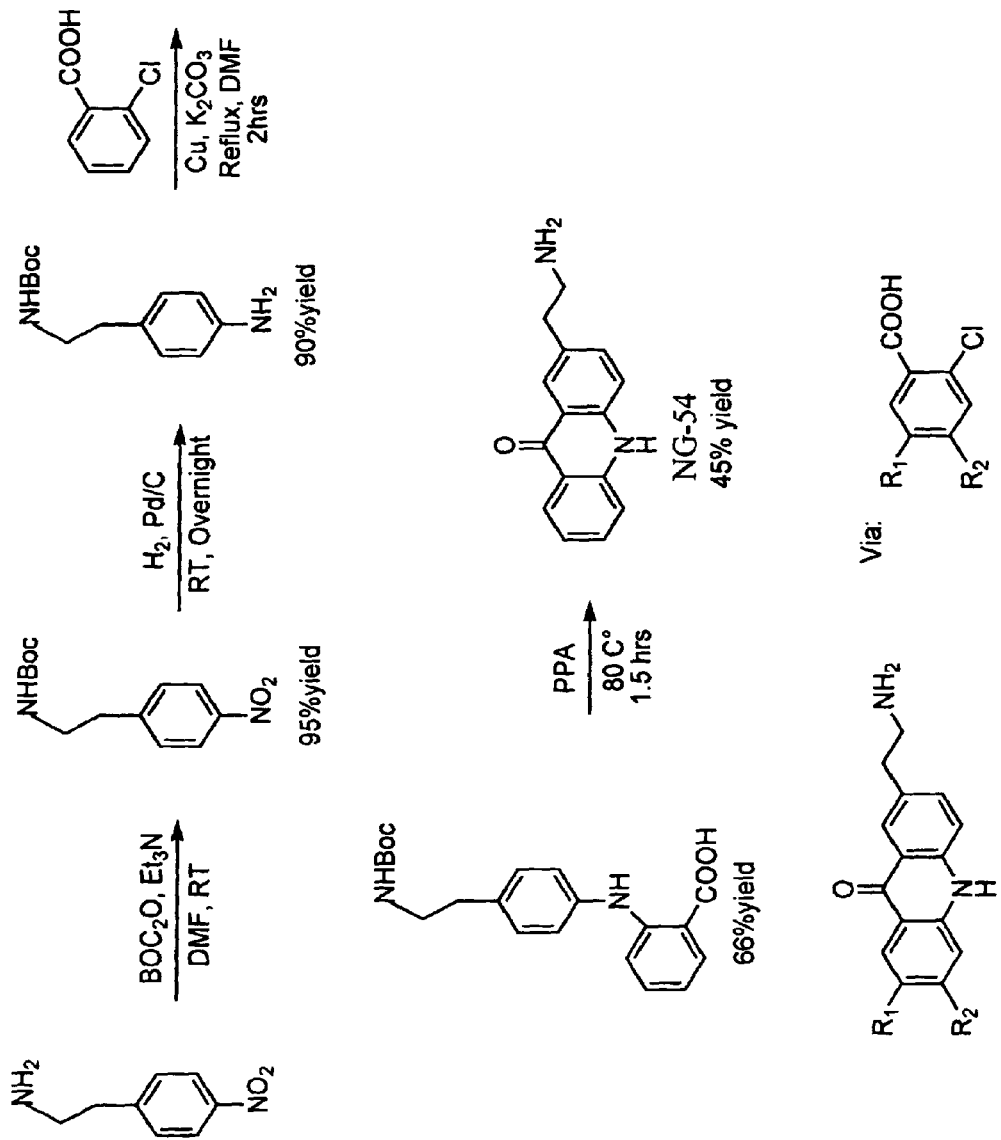
FIG. 9: Synthesis of acridinone-based probes using a di-tert-butyl pyrocarbonate protecting group and a Pd/C catalyst.
Figure 10:
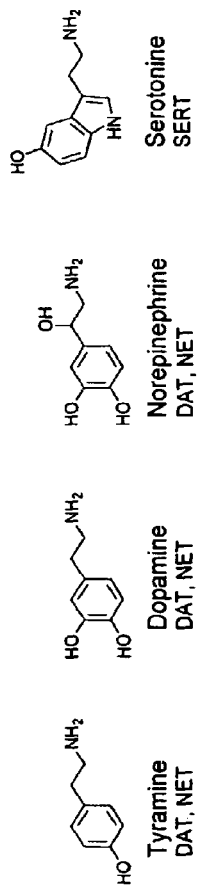
FIG. 10: Various monoamine transporter substrates. Endogenous substrates include tyramine, transported by DAT and NET, dopamine transported by the DAT and NET, norepinephrine, transported by DAT and NET, and serotonin transported by SERT. Synthetic substrates and their known and predicted transporters.
Figure 10:
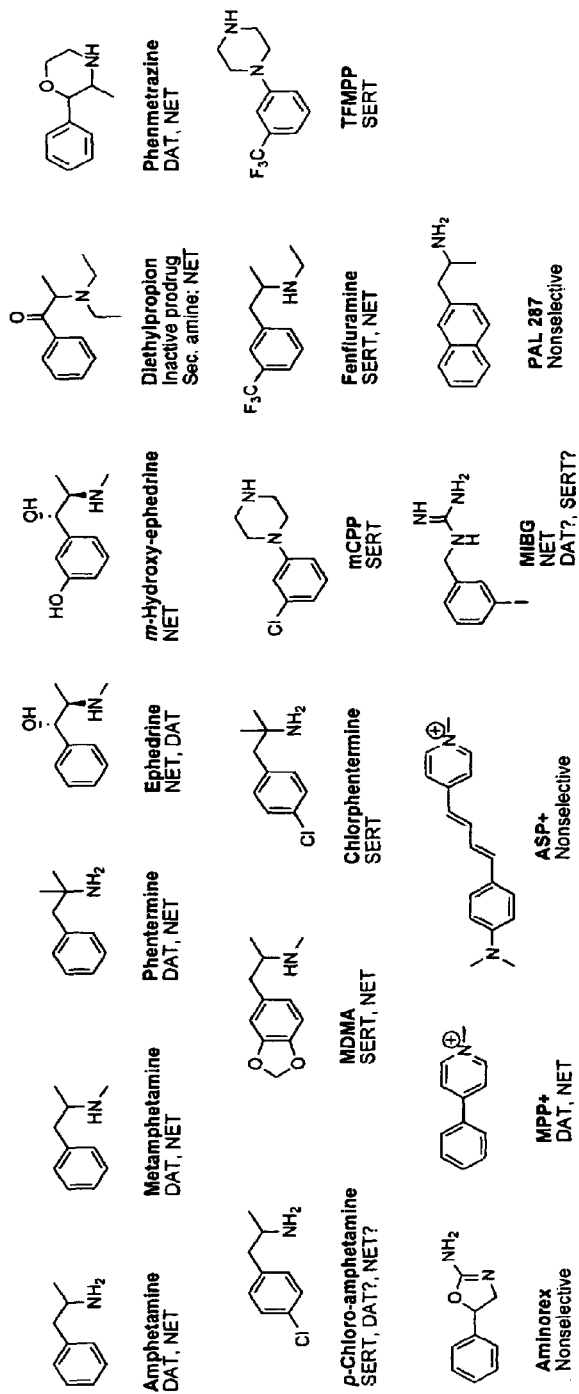
Figure 11:
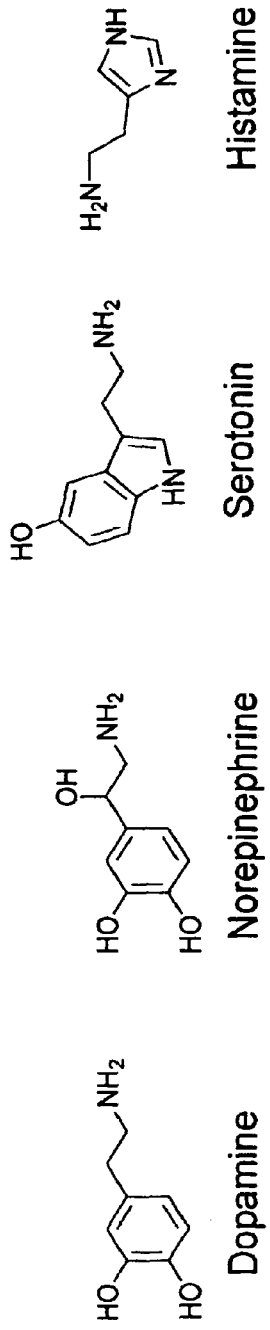
FIG. 11: Various VMAT substrates. Endogenous substrates include dopamine, norepinephrine, serotonin and histamine. Synthetic substrates include MDMA, MPP+, p-chloro-amphetamine and MIBG.
Figure 11:
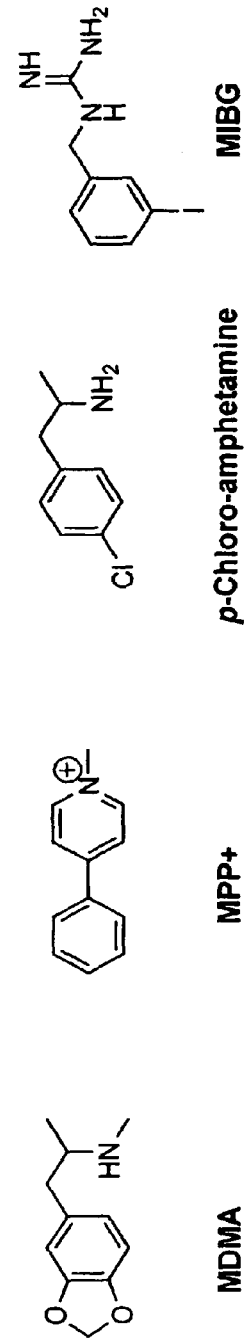

Specific syntheses for naphthalene, coumarin and acridinone probes are set forth in FIGS. 7, 8 and 9 respectively.

The emission wavelength, fluorescent intensity, and the pH dependence of the probes are determined using standard fluorimetric techniques. The emission properties may further be enhanced by the addition of an aromatic ring in the 3-position of the coumarin system (12).

Figure 5:
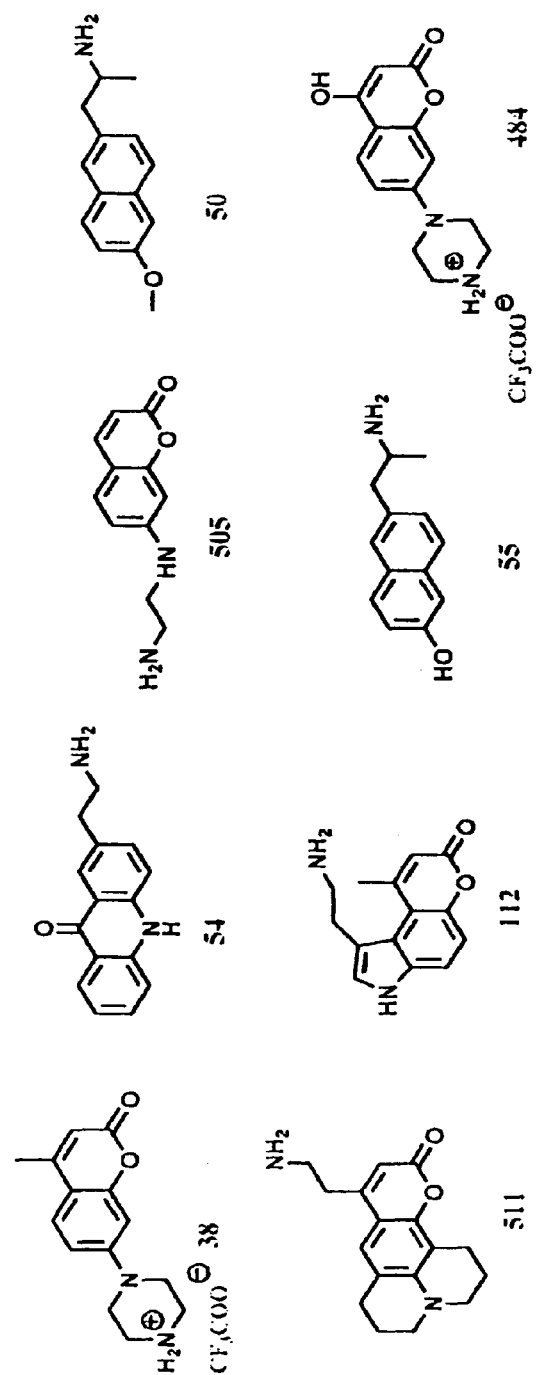
FIG. 5: Synthesized fluorescent monoamine transporter probes.
Figure 20:
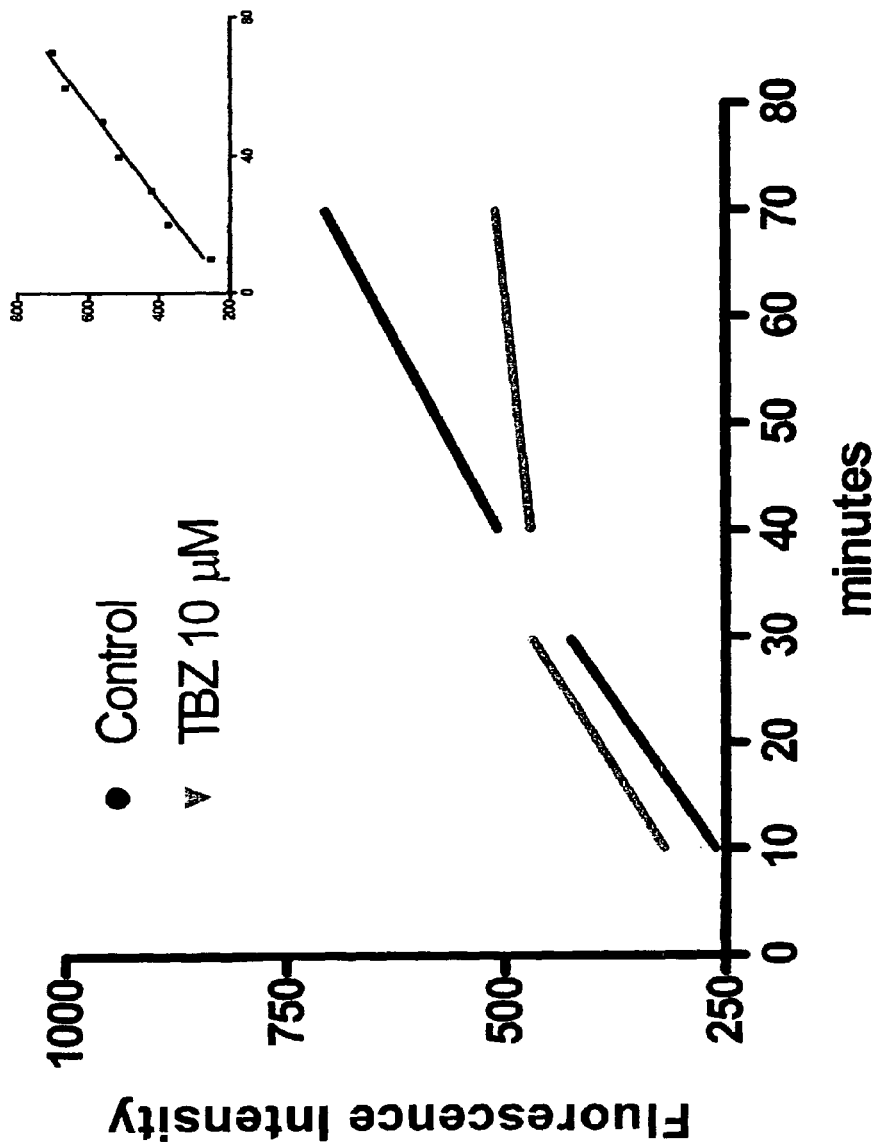
FIG. 20: Inhibition of VMAT uptake of probe 511 by tetrabenazene in chromaffin cells. Decreased uptake seen in presence of 10 uM tetrabenzene (TBZ). Tetrabenazene was added after 20 minutes and acts after 30 minutes. For the cells treated with tetrabenazene, there is a clear change in slope from the first 30 minutes to the remaining 30 minutes, compared to the control cells.

Examples of probes synthesized are shown in FIG. 5. The compounds in FIG. 5 were designed and synthesized to monitor Vesicular Monoamine Transporter (VMAT) activity in chromaffin cells and brain slices, as well as Dopamine Transporter (DAT) and Serotonin Transporter (SERT) activity in transfected oocytes. At 50 nM, probes 511 and 38 are actively taken up into chromaffin vesicles, a process that can be abolished by Tetrabenazine, an established VMAT 1 and 2 inhibitor (17), and see FIG. 20. As found by cyclic voltammetry in transfected oocytes, at 10 µM probes 50 and 55 show transport currents for DAT but not for SERT.

Figure 18:
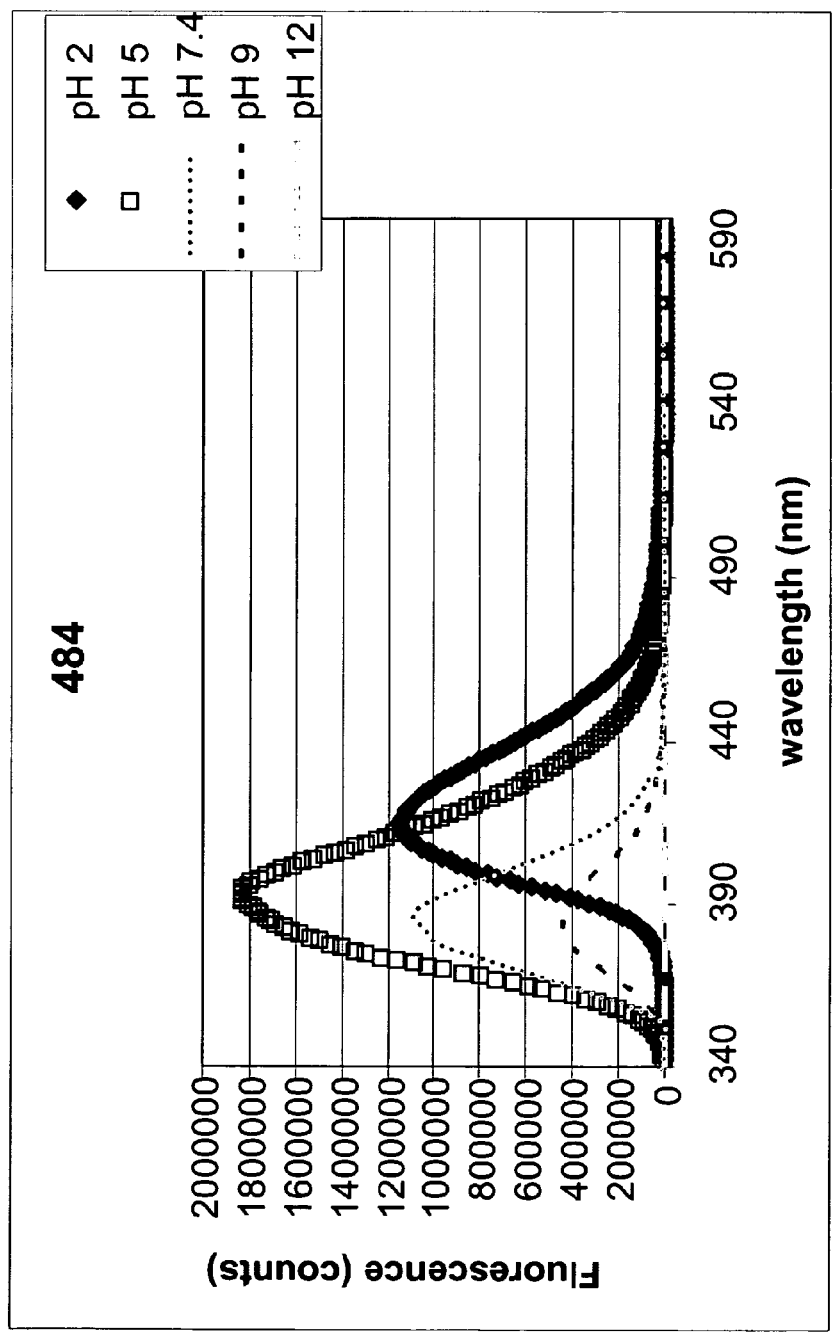
FIG. 18: pH dependency of fluorescence spectra for Probe 484. Spectra measured at pH 2, 5, 7.4, 9 and 12, with a shift in fluorescence emission maxima seen with changing pH.
Figure 21:
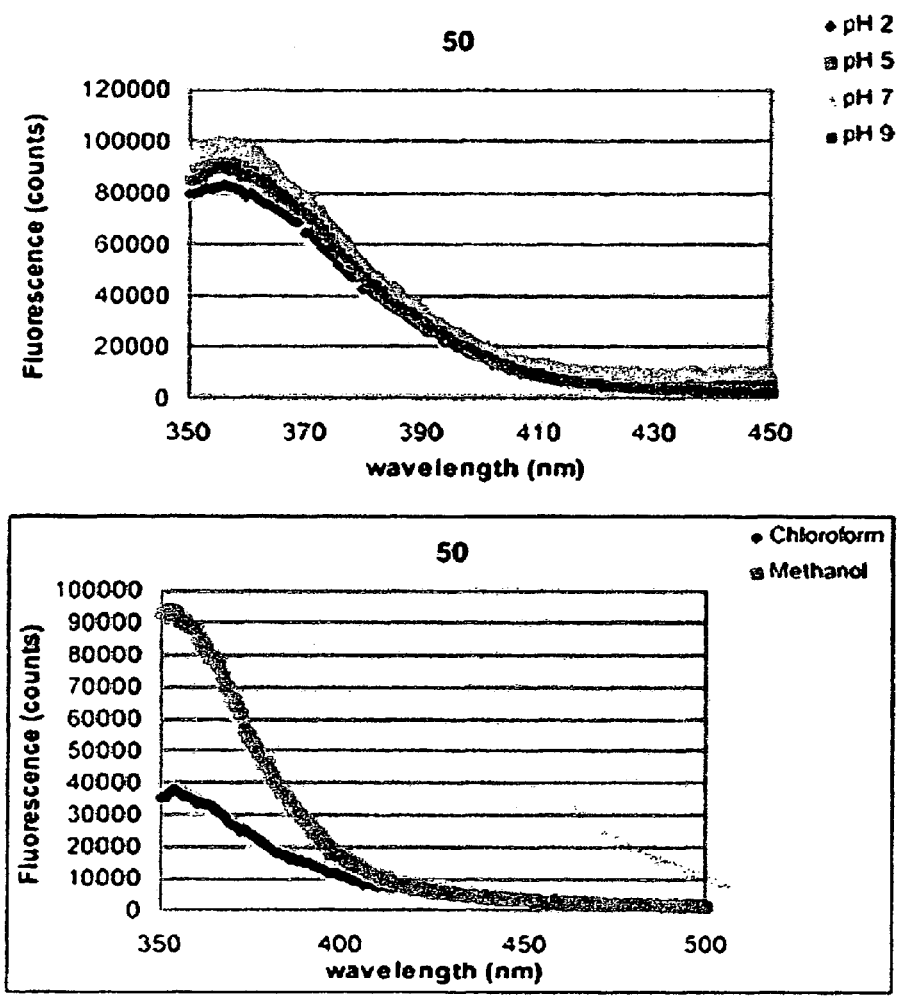
FIG. 21: Fluorescence spectra and pH dependency of fluorescence spectra for Probes 50 and 55, and extinction coefficients (M$^{-1}$cm$^{-1}$), $\lambda_{max}$ and $\lambda_{em}$ (nm) for each probe.
Figure 21:
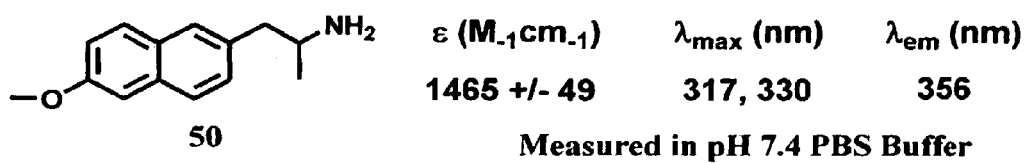
Figure 21:
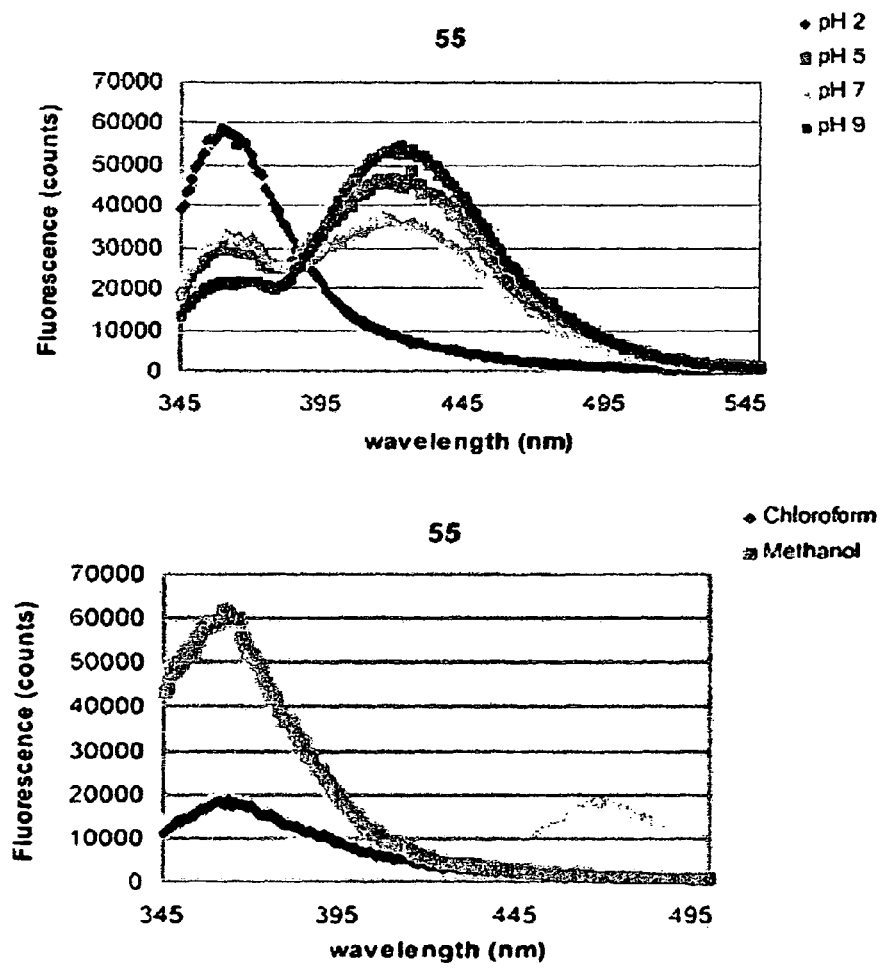
Figure 21:
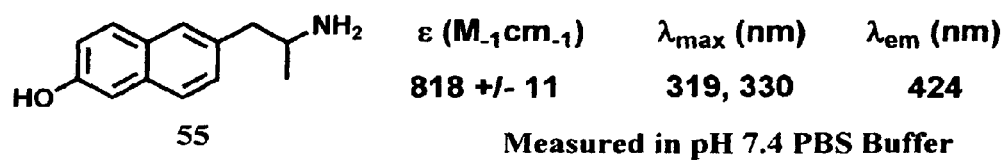

It was found that the probes' fluorescence did not drop in aqueous buffer solution. In contrast, the fluorescence of acridine orange and coumarin 1 (C1) drops in water. Probes 484 (FIG. 18) and 55 (FIG. 21) were found to possess pH-dependency, which considering the pH state of vesicles, could itself be a basis for measuring VMAT activity. For example, probe 484 may be measured as being transported from the synaptic cleft across the pre-synaptic membrane and then transported into vesicles, the different pH of each causing the fluorescence of the probe to change accordingly.

Figure 22:
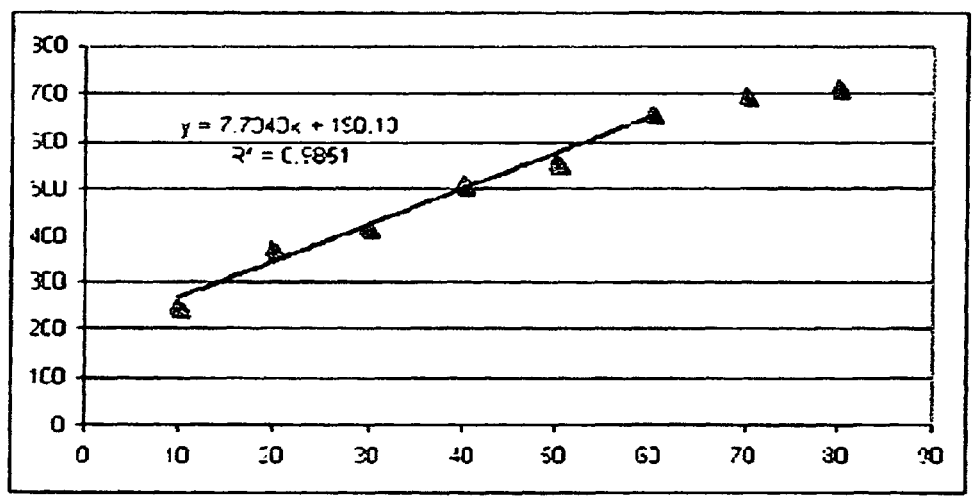
FIG. 22: At 500 nM in physiological saline solution, the intracellular concentration of probe 511, as judged by fluorescence, increases linearly for at least 60 minutes.
Figure 22:
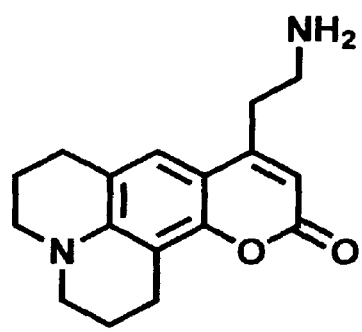

Probes 484, 511 and 54 showed a linear concentration dependency at up to 50 µM (see FIG. 22 for probe 511). It was also determined that the disclosed probes are more polar than acridine orange or coumarin 1 (see FIG. 12), but only as polar as, or less polar than, dopamine or serotonin.

The development of fluorescent neurotransmitter analogs, so called "optical false neurotransmitters" or "fluorescent false neurotransmitters", designed to act as a tracer of neurotransmitters during transport into vesicles via the Vesicular Monoamine Transporters (VMAT) as well DAT, SERT and NET, enables examination of the dynamics of neurotransmission and the neurotransmitter "life cycle", including storage, release, and reuptake, as well as monitoring of monoamine transporter activity in disease and healthy states, and identification of agents that inhibit or promote transporter activity as well as compete with the physiological substrates.

The ability to selectively load neurotransmitter vesicles with a molecular probe provides entirely new tools to study the "life cycle" of neurotransmitters and dynamics of neurotransmission. For example, a new method for localizing synapses is provided as well as monitoring vesicle trafficking and measuring the regulation of vesicle filling. This last phenomenon is clearly affected by psychostimulants, and seemingly by a variety of diseases including Parkinson's, and possibly by learned behavior (2 and 3). The fluorescent substrates proposed herein provide the best means to examine many of the questions in these areas of research that have not been directly approachable, and allow real-time monitoring of neurotransmission-related activity for, inter alia, disease state diagnoses, as well as, inter alia, enhancement or inhibition of VMAT activity.

Example 2

Figure 3:
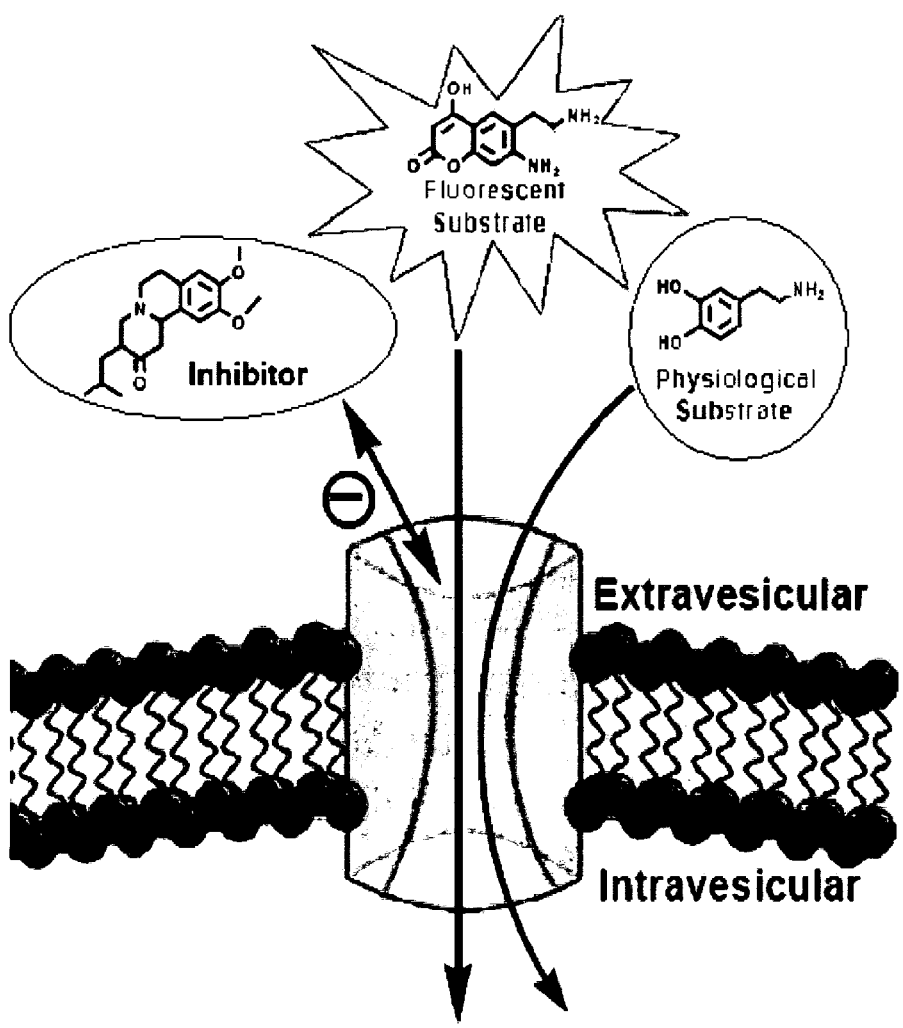
FIG. 3: Schematic showing that, in contrast to the competitive inhibitor, the fluorescent substrate competes with physiological substrates for vesicular transport.

Biological assays were designed to investigate the ability of the fluorescent probes to function as VMAT substrates. In designing such assays, it is important to differentiate between a competitive inhibitor and competitive substrate for VMAT; both bind to the transporter in the active site, but only the latter is transported into the vesicle (FIG. 3).

Chromaffin cells are an excellent model system as the cytoplasm of these cells in culture is almost completely filled with large dense core vesicles that accumulate catecholamines by VMAT.

After establishing the probes as substrates for VMAT in isolated granules, the compounds were examined in chromaffin cells. If necessary, metabolism of the probes by MAO (present in mitochondria) may be reduced by the addition of a suitable inhibitor (deprenyl for MAO B, clorgyline for MAO A) or by simply methylating the α-position of the amine (10, 14). In accordance with this, the compounds as set forth in this disclosure and methylated at the α-position of the amine are encompassed within the scope of this invention.

Figure 19:
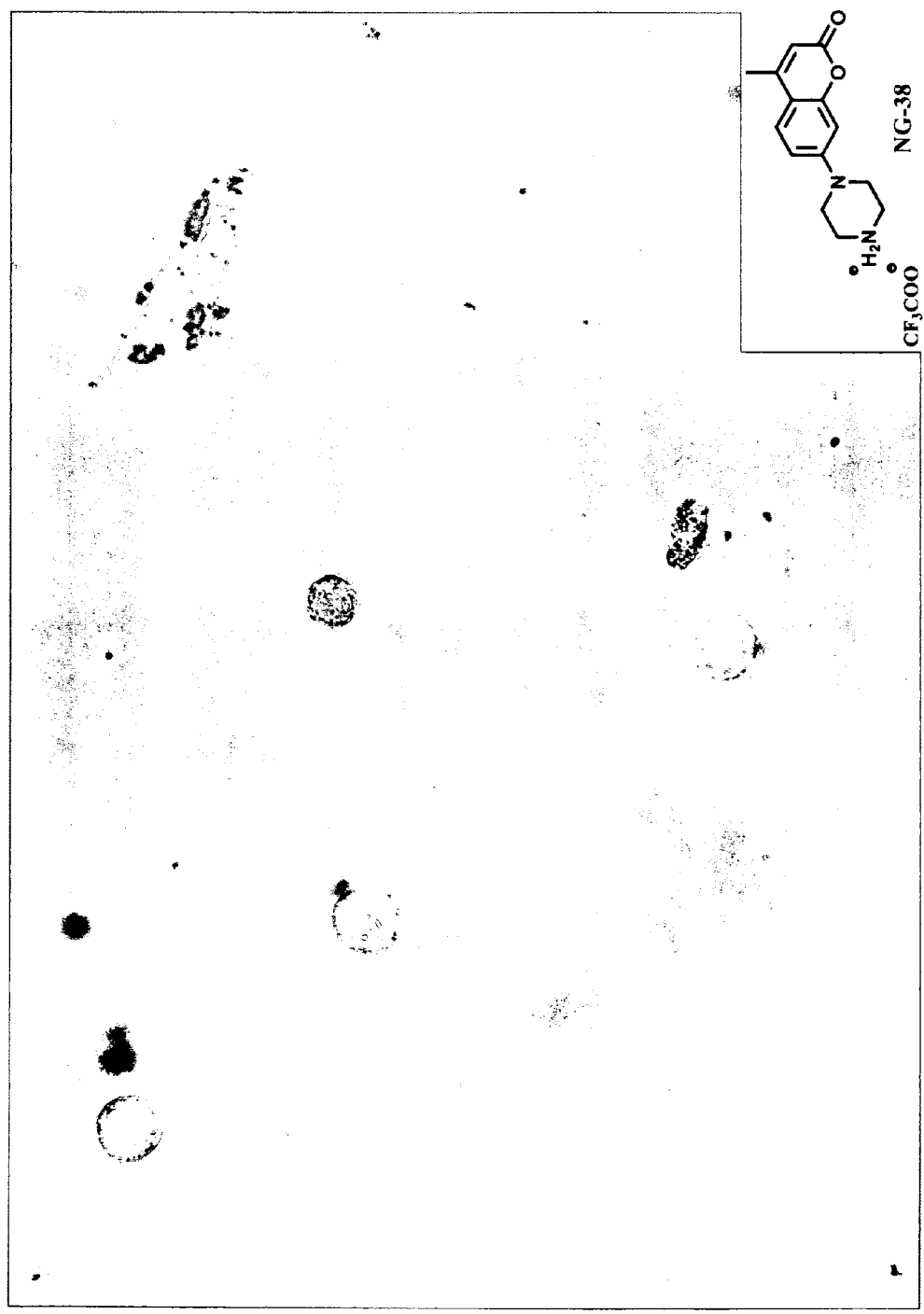
FIG. 19: Live and dead chromaffin cells are shown in this figure, but only live cells load with the probe 38 as determined by their fluorescence. Since probe 38 is only taken up by live chromaffin cells its uptake must be energy dependent. Probe 38 is at a concentration of 500 nM in physiological saline solution
Figure 23:
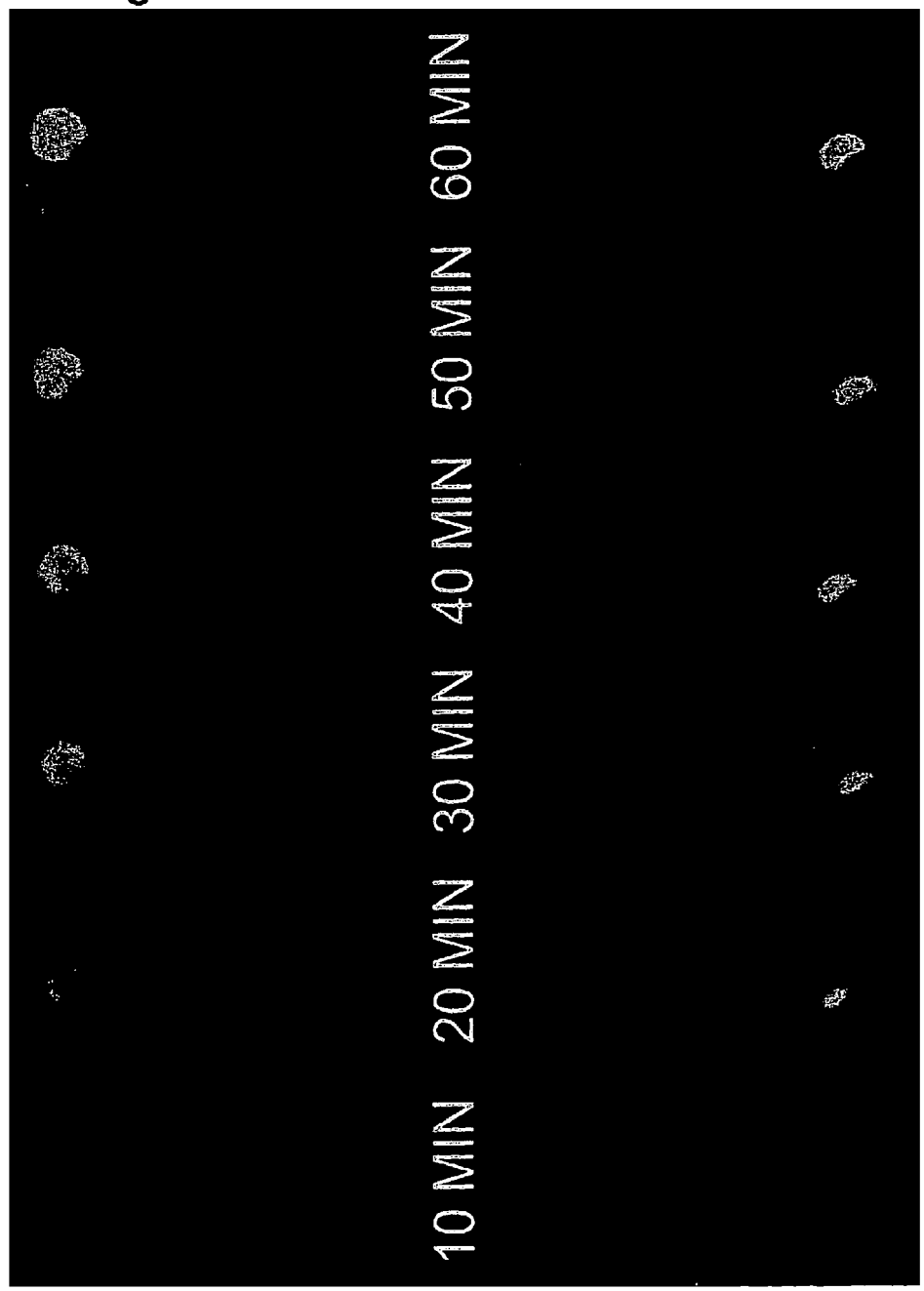
FIG. 23: Temporal series of fluorescence images shows probe uptake over time in chromaffin cells, corresponding to FIG. 22, demonstrating nuclear exclusion of the probe 511.
Figure 24:
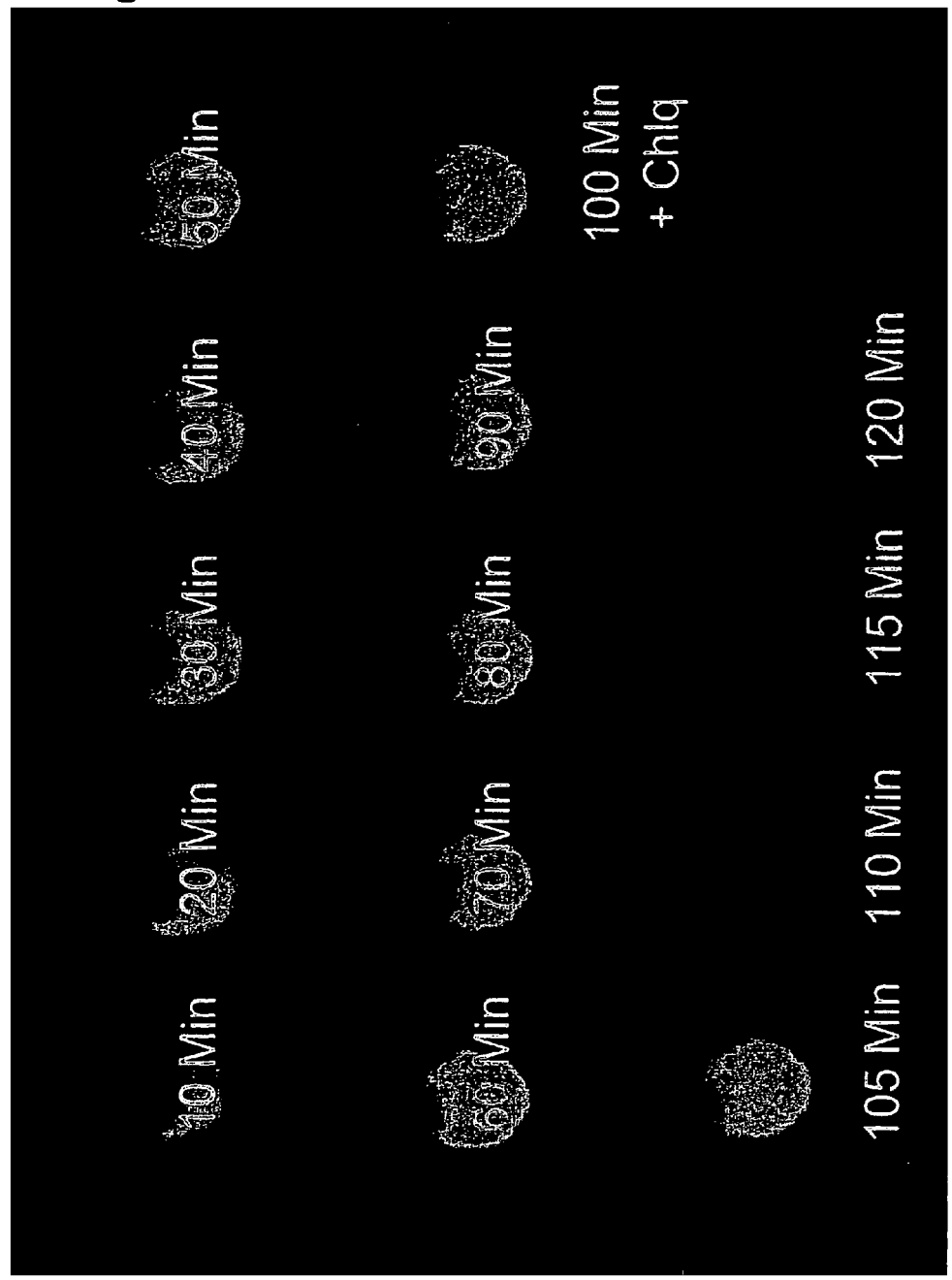
FIG. 24: Accumulation of probe in acidic compartments of a cell. Chloroquine is a weak base commonly used to dissipate the pH gradient across the vesicular membrane. After loading the cell with probe 511 at 500 nM for 90 minutes, chloroquine was added. The intracellular fluorescence subsequently dissipated, indicating that probe 511 is present in acidic compartments, such as vesicles, in the cell.
Figure 25:
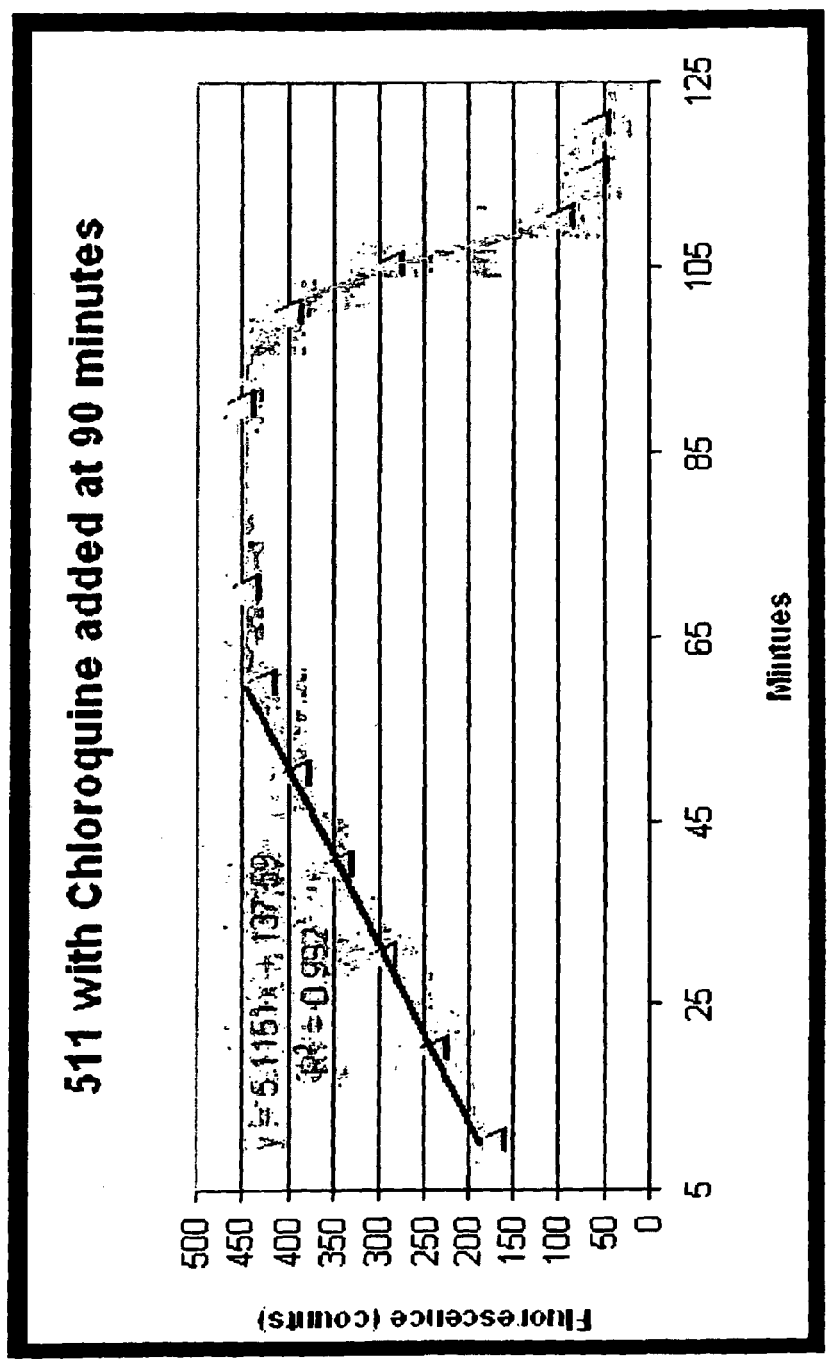
FIG. 25: Probe 511 contained in acidic compartments as demonstrated by a drop in cell fluorescence seen upon the addition of chloroquine at 90 mins (see images in FIG. 24). The intracellular fluorescence drops to background levels indicating that probe 511 almost exclusively stains acidic compartments.
Figure 26:
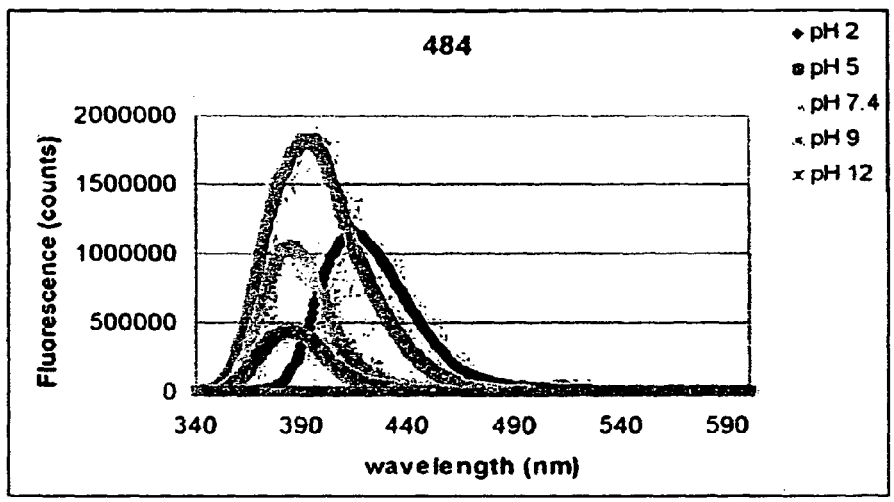
FIG. 26: Fluorescence spectra and pH dependency of fluorescence spectra for probes 484 and 38, and extinction coefficients (M$^{-1}$cm$^{-1}$), $\lambda_{max}$ and $\lambda_{em}$ (nm) for each probe.
Figure 26:
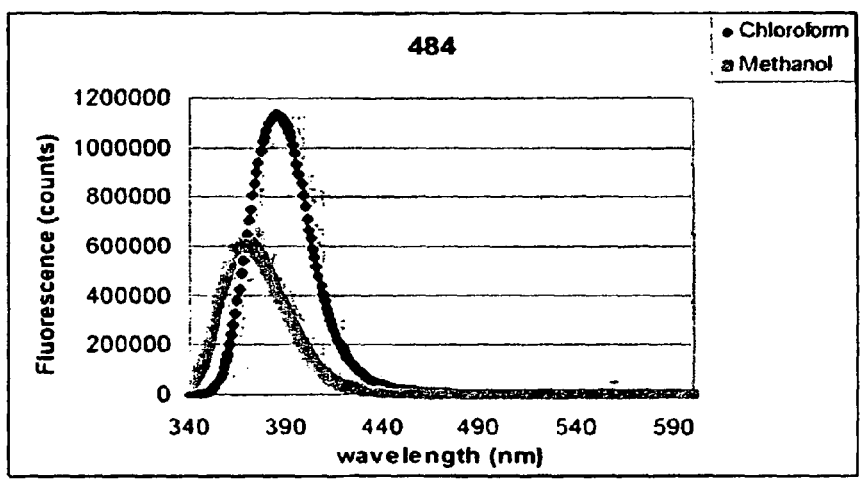
Figure 26:
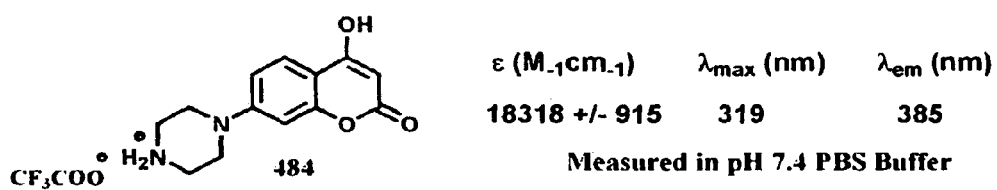
Figure 26:
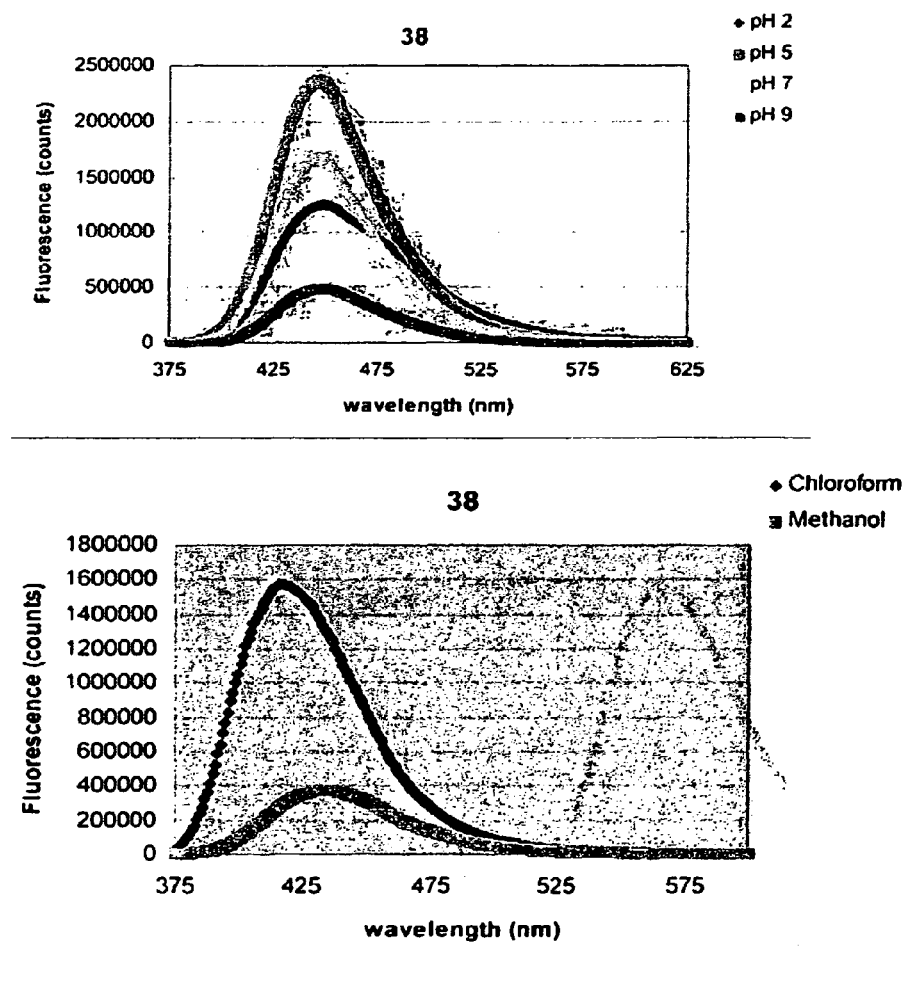
Figure 26:
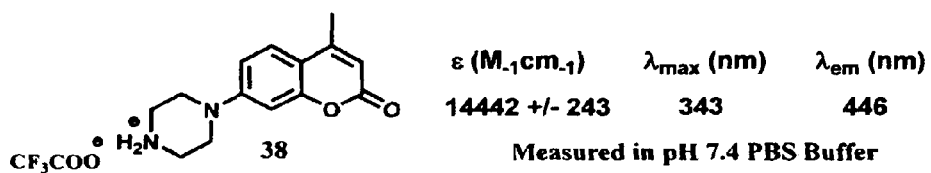
Figure 27:
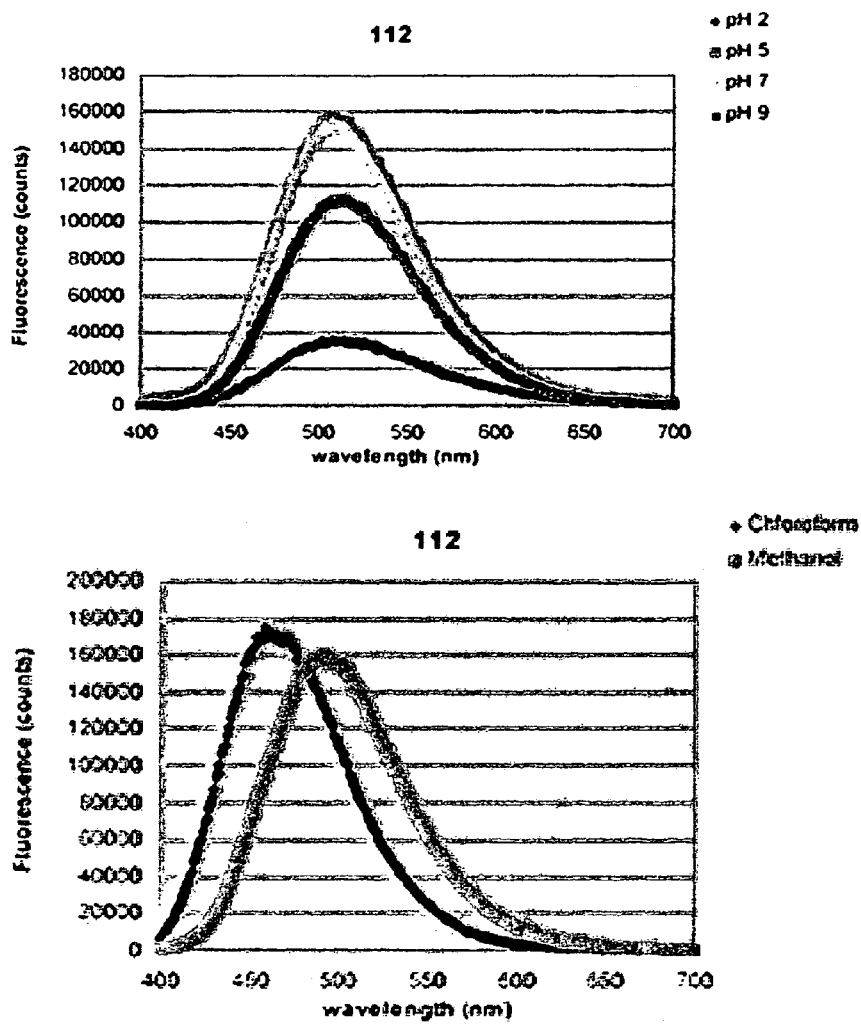
FIG. 27: Fluorescence spectra and pH dependency of fluorescence spectra for probe 112, and extinction coefficient (M$^{-1}$cm$^{-1}$), $\lambda_{max}$ and $\lambda_{em}$ (nm).
Figure 27:
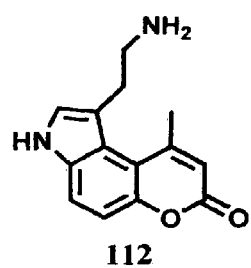
Figure 28:
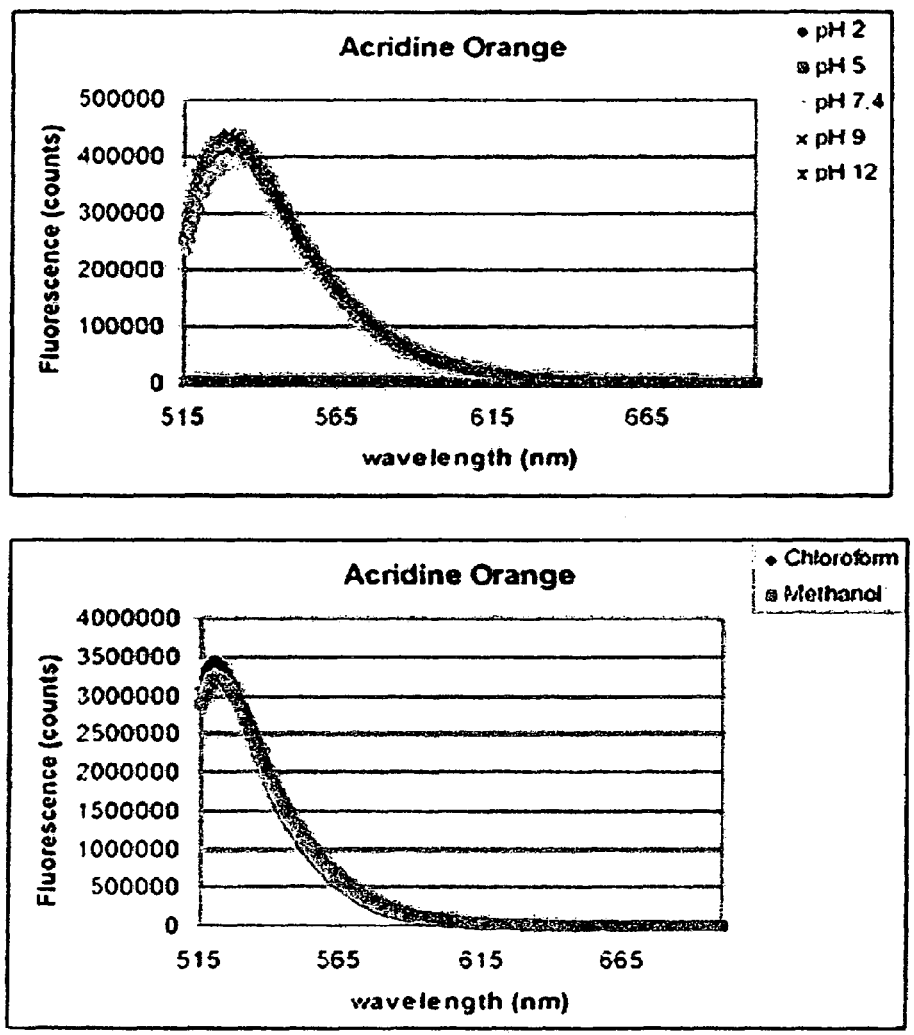
FIG. 28: Fluorescence spectra and pH dependency of fluorescence spectra for acridine orange and probe 54, and extinction coefficients (M$^{-1}$cm$^{-1}$), $\lambda_{max}$ and $\lambda_{em}$ (nm) for each.
Figure 28:
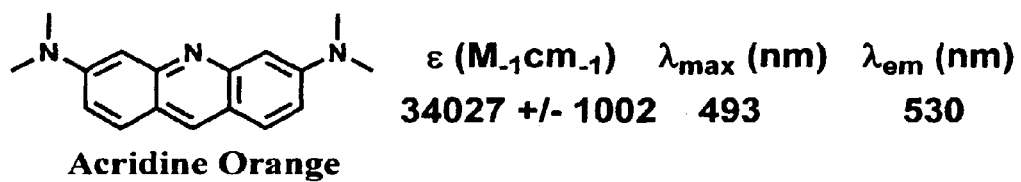
Figure 28:
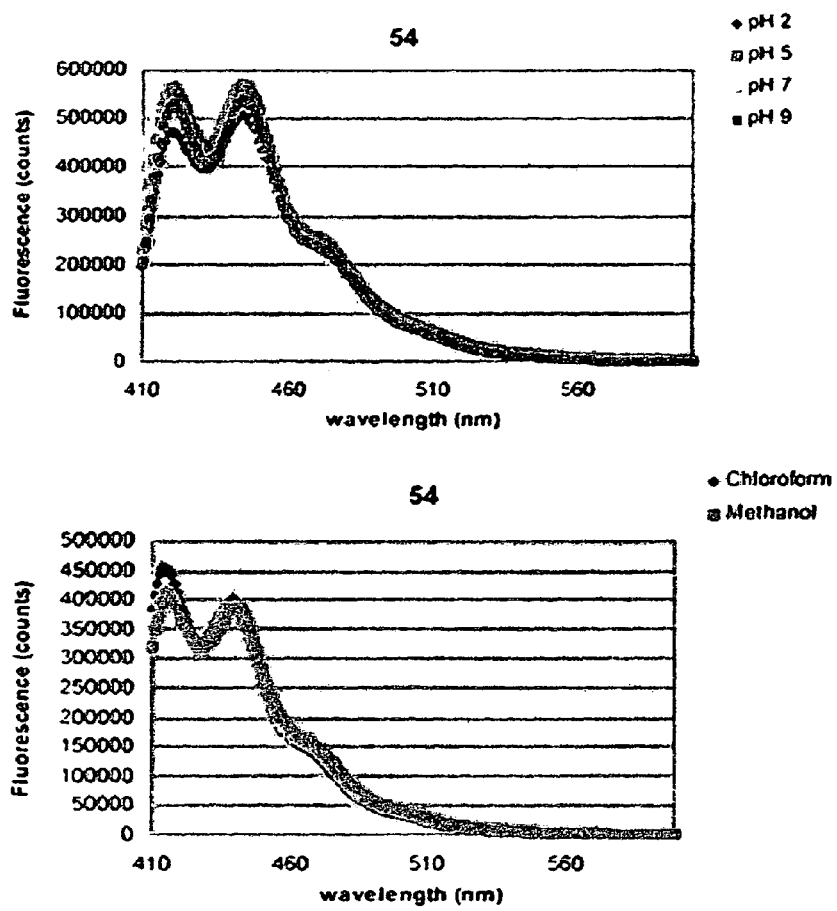
Figure 28:
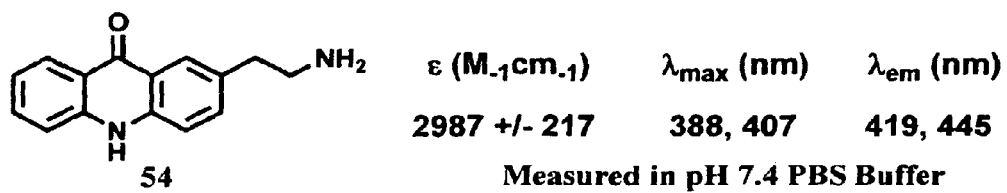
Figure 29:
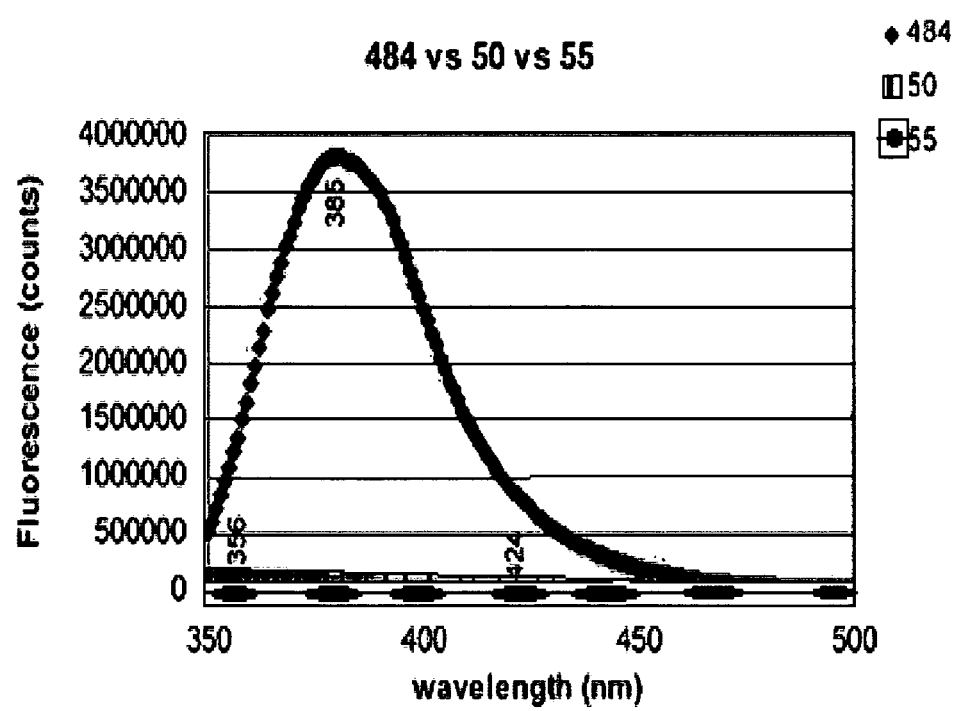
FIG. 29: Emission spectra for probes 484 ($\lambda_{ex}$=319 nm and $\lambda_{em}$=385 nm), 50 ($\lambda_{ex}$=330 nm and $\lambda_{em}$=356nm), and 55 ($\lambda_{ex}$=330nm and $\lambda_{em}$=424 nm).
Figure 30:
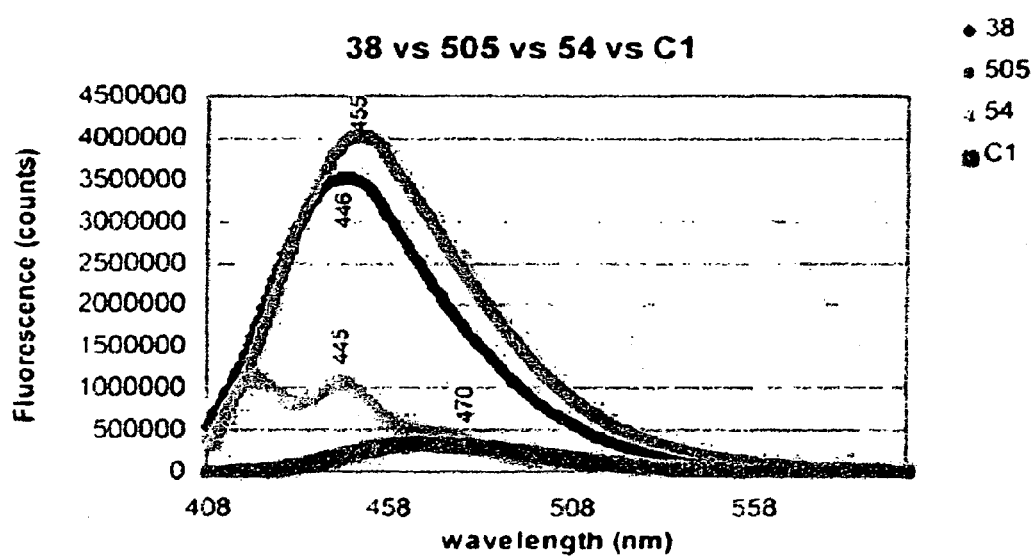
FIG. 30: Emission spectra for probes 38 ($\lambda_{ex}$=343 nm and $\lambda_{em}$=446 nm), 505 ($\lambda_{ex}$=361 nm and $\lambda_{em}$=455 nm), 54 ($\lambda_{ex}$=388 nm and $\lambda_{em}$=445 nm) and Coumarin 1 ($\lambda_{ex}$=384 nm and $\lambda_{em}$=470 nm).
Figure 31:
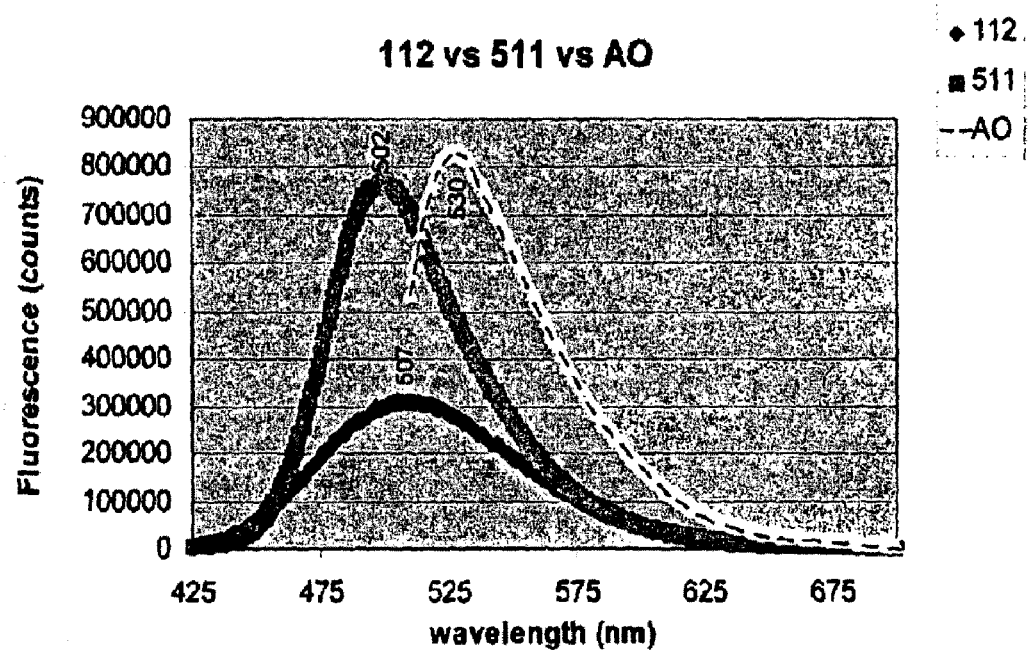
FIG. 31: Emission spectra for probes 112, 511 and acridine orange.
Figure 31:
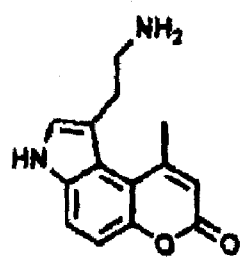
Figure 31:
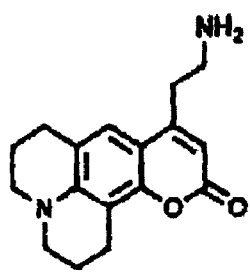
Figure 31:
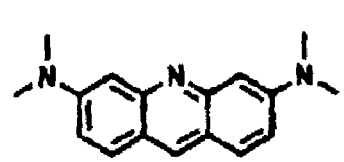
Figure 32:
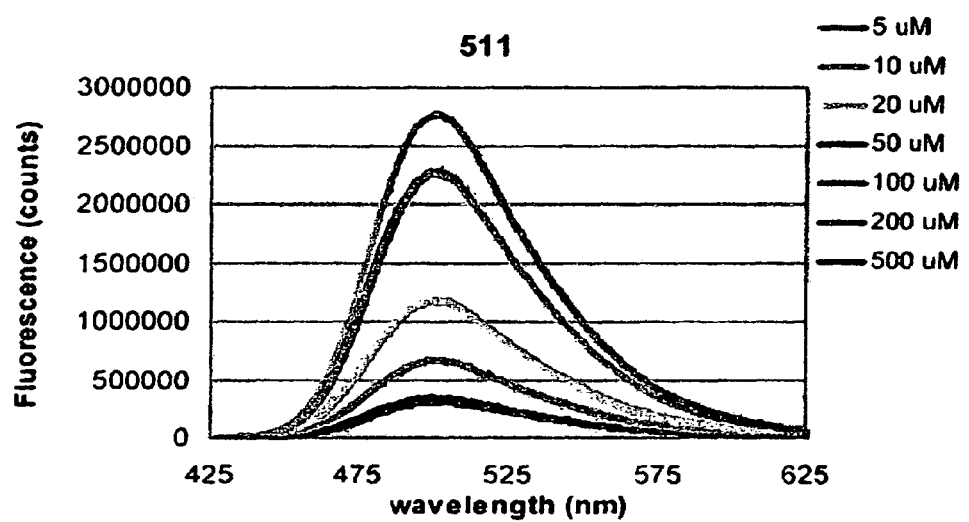
FIG. 32: Behavior of probe 511 at increasing concentrations in phosphate buffer. The estimated concentration of neurotransmitters in the intravesicular matrix is 150000 times higher than that of the cytosol. Therefore the behavior of probe 511 was investigated at increasing concentrations. The results indicate that in phosphate buffer, the fluorescence of probe 511 increases linearly up to 50 μM along with its concentration.
Figure 32:
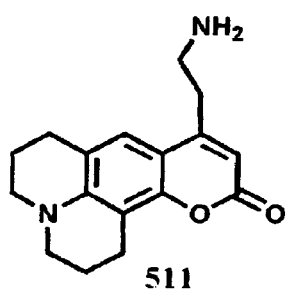
Figure 33:
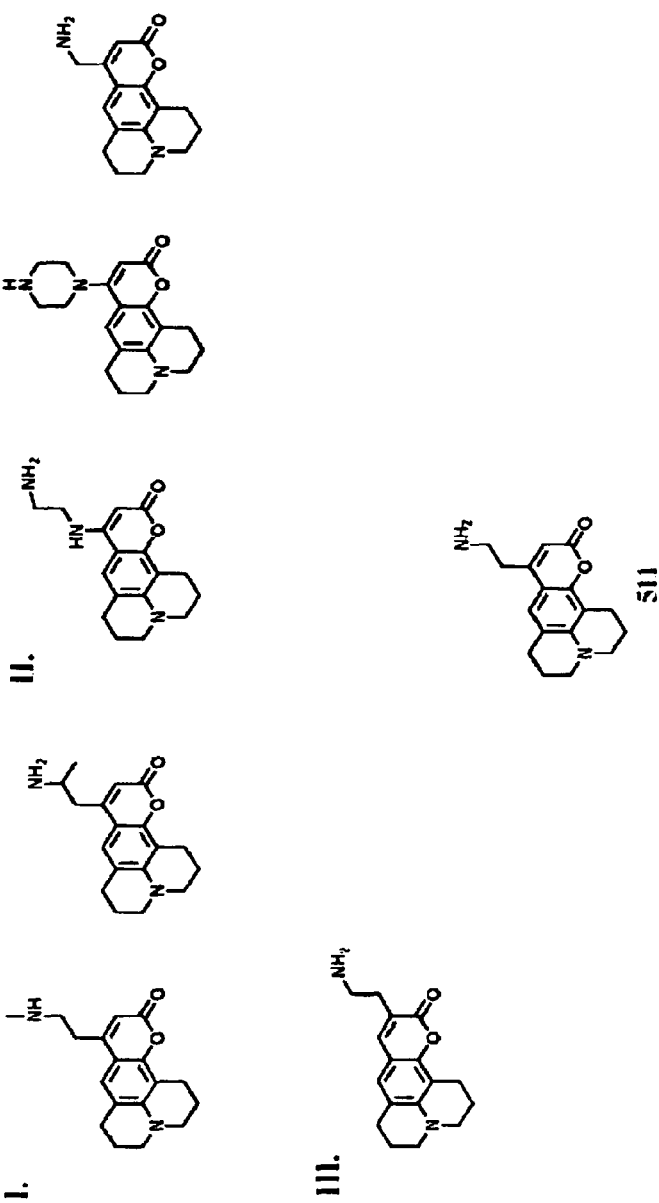
FIG. 33: Probe 511 derivatives.
Figure 34:
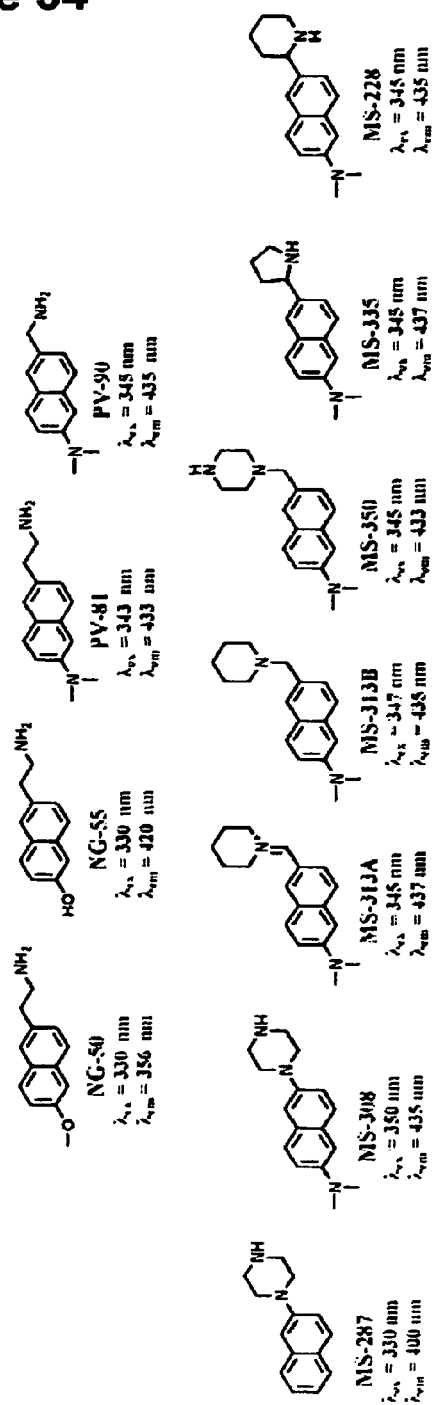
FIG. 34: Synthesized SERT and DAT fluorescent substrates.

It was found that probes 38 and 511 selectively label healthy chromaffin cells, see FIGS. 19A and 19B and FIG. 23, and that 511 accumulates in acidic compartments of the cells. Probe 38 was found not to stain the nuclei of cells. This acidic compartmentalization could be abolished by chlorquine exposure, see FIGS. 24 and 25. It was also found that uptake of 38 and 511 was inhibited by tetrabenazene (uptake was significantly inhibited compared to control, p=0.001). Probes 112 and 54 were found not to significantly label chromaffin cells.

Figure 35:
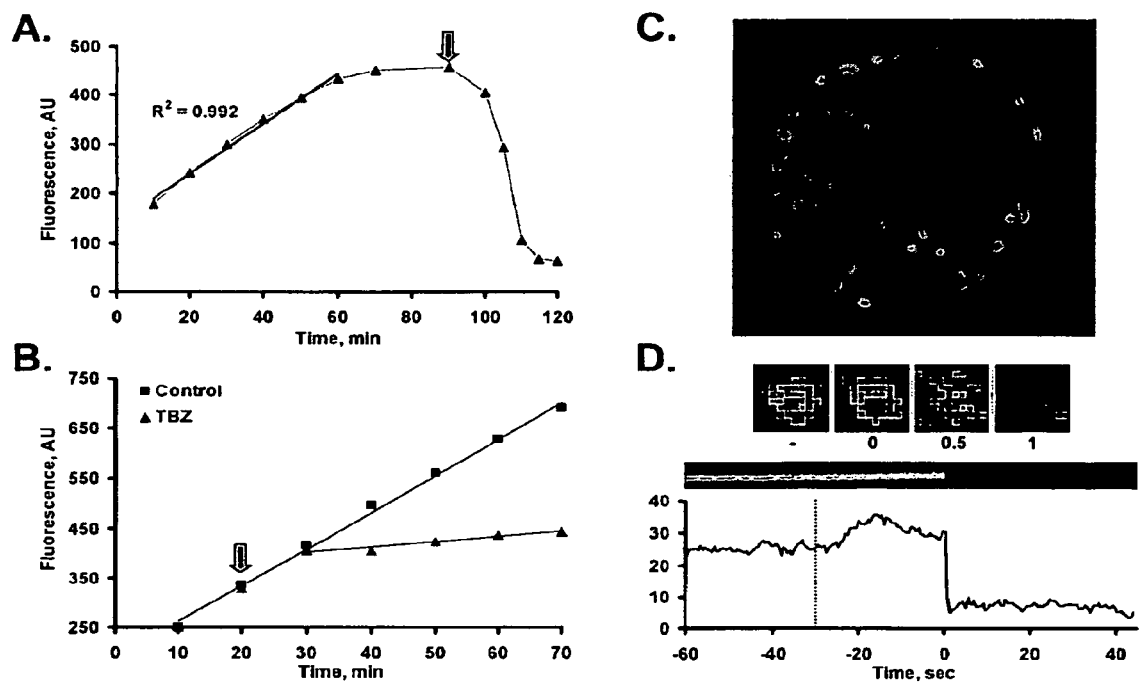
FIGS. 35A-35D: In mouse chromaffin cells, FFN 511 is taken up by large dense core vesicles (LDCVs) in a VMAT-dependent manner and released by exocytosis. (A) Two-photon image of a chromaffin cell reveals granular localization of FFN 511. (B) Uptake of FFN 511 (500 nM) measured by fluorescence microscopy of single chromaffin cells, was linear within 10-60 min. The labeling was abolished by addition of lipophilic base chloroquine (100 μM, arrow). (C) FFN 511 accumulation was inhibited by VMAT inhibitor tetrabenazine (TBZ, 10 μM). (D) The time course of FFN 511 exocytosis from a single LDCV observed with TIRF. Images from chromaffin cells stimulated with high potassium (the beginning of the stimulation is indicated by dotted line on the lower panel) were taken at 500 ms intervals. Upper row shows consecutive images of a single vesicle. Orthogonal section though this vesicle and its integrated intensity are in the middle and lower panels

On the basis of initial encouraging results, compound FFN 511 was submitted to rigorous investigation, from which it emerged as a promising imaging probe. Catecholamines are stored in chromaffin large dense core vesicles (LDCVs), which contain vesicular monoamine transporter 1 (VMAT1). Although VMAT 1 and 2 are distinct proteins, they share many functional characteristics. FIG. 35A shows a two-photon image of a cultured mouse chromaffin cell stained with 500 nM FFN 511 for 30 min with distinctive granular localization of fluorescence. FFN 511 accumulated selectively in chromaffin cell LDCVs, and not in connective tissue cells lacking VMAT proteins. Further analysis revealed that the uptake of the compound was linear between 10-60 minutes while the resulting fluorescence was completely abolished by addition of the lipophilic weak base chloroquine, which collapses the vesicle pH gradient and redistributes catecholamines from vesicles to the cytoplasm (FIG. 35B) (35). Probe accumulation was also inhibited by the VMAT inhibitor tetrabenazine (FIG. 35C), confirming that FFN 511 accumulation is VMAT-dependent. Indeed, direct interaction between FFN 511 and VMAT was demonstrated by an in vitro competitive binding assay, which provided the apparent $IC_{50}$ of 2.5 µM for probe FFN 511, a value close to DA itself ($IC_{50}$ ~1 µM), as shown by inhibition of 5HT binding to membranes obtained from HEK cells stably transfected with VMAT2 (34).

Total internal reflectance fluorescence microscopy (TIRF) was used as a functional assay for the ability of FFN 511-loaded chromaffin granules to undergo stimulation-dependent exocytosis. TIRF allows for fluorescence excitation in a narrow ~100 nm thick layer of the cell immediately adjacent to the surface. FIG. 35D shows the time course of FFN 511 destaining during neurosecretory fusion of a single LDCV upon high potassium stimulated exocytosis.

Figure 4:
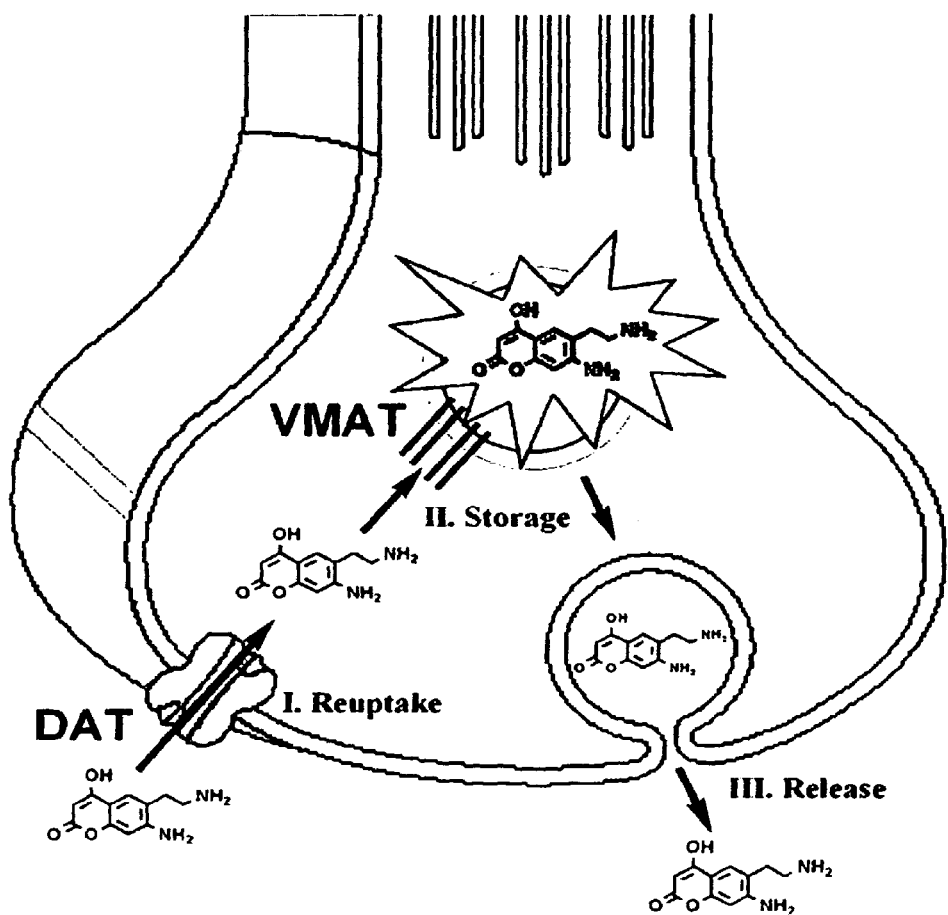
FIG. 4: Fluorescent probes mimicking neurotransmitters enable monitoring and imaging of the dynamics of uptake, storage and release of signaling molecules at the synapse. DAT, dopamine transporter; VMAT, vesicular monoamine transporter.

It is generally assumed that similar mechanisms operate in vesicles from less available cells such as neurons. Accordingly, the selective staining of vesicles in living neurons is also examined. The selective probes disclosed herein would allow for visualization and real-time monitoring of all key events of the neurotransmitter life cycle (FIG. 4). For example, after the probe is transported into the cytosol of the neuron by monoamine transporters (re-uptake) and then accumulated into vesicles by VMAT (storage), the vesicle's interior will increase in fluorescent intensity. The signal-induced exocytosis will cause the release of the probe into the synaptic cleft, which will be visualized as destaining or a decrease in intensity of the fluorescent puncta (synaptic terminals). (It should be noted that the fluorescent substrates provide a means to examine the activity of plasma membrane transporters (MATs), which are the sites of action of cocaine and common antidepressant drugs since the monoamine transporters seem to have similar substrate selectivity as VMATs. Further, since the dopamine and serotonin transporters (DAT and SERT) show selectivity towards their respective neurotransmitters, selective probes can be synthesized for either transporter subtypes (15, 16)).

Accordingly, further to the positive results in chromaffin cells, FFN 511 was examined in the mouse CNS. Gratifyingly, fluorescent labeling was clearly observed in presynaptic terminals in acute slices from striatum, the region with the richest dopaminergic innervation in the CNS, with no labeling in corpus callosum, and fainter fluorescence with patchy distribution in the cortex.

Figure 36:
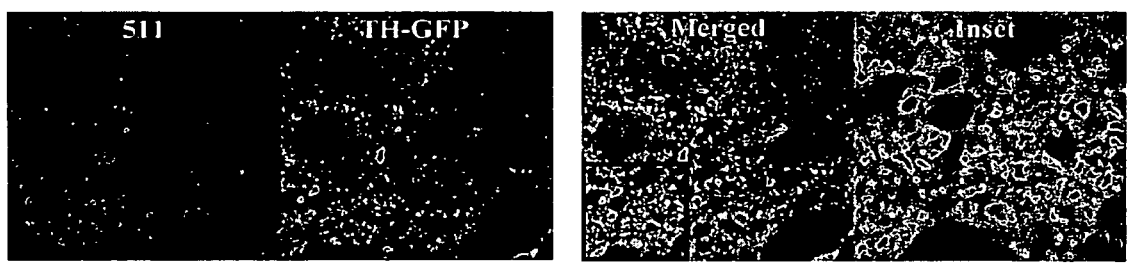
FIGS. 36A-36C: FFN 511 selectively labels DA terminals in live cortical-striatal acute slice. (A) FFN 511 (left hand side of 36A) label matches well with that of TH-GFP (right hand side of 36A). (B) FFN 511 labeling was strongly inhibited by VMAT inhibitor Reserpine (10 μM, 2 hours). (C) Striatal FFN 511 label after unilateral 6-OHDA injection. Right panel: 6-OHDA lesion side; left panel: control side. Adult mice were injected 15 μg 6-OHDA/total weight at the right striatum and striatal slices were cut 21 days post-lesion and were examined by CV to confirm a complete lesion before 2p imaging.
Figure 36:
Figure 36:
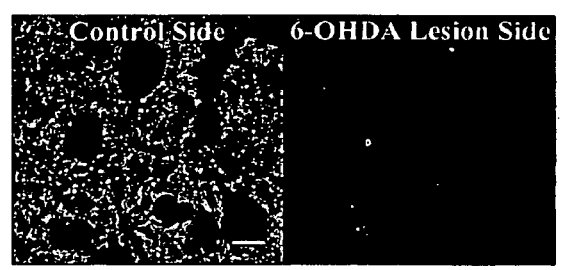

Incubation of a living striatal slice with FFN 511 affords an image where the size of fluorescent puncta correlates well with the size of axon terminals (~1 µm, FIG. 36). Distribution of FFN 511 was compared to DA neurons using striatal slices prepared from a transgenic mouse expressing GFP under the control of tyrosine hydroxylase (TH) promoter (36). Importantly, probe FFN 511 exhibits favorable photophysical properties that enable simultaneous imaging with GFP: although FFN 511 and GFP have similar emission profiles (emission maximum ~500 nm), the excitation wavelengths are sufficiently different for selective imaging of one probe without the contribution of the other. The overall pattern of FFN 511 label matches well with that of TH-GFP and detailed comparison provided excellent co-localization of the axonal terminals, illuminated in two different excitation channels—clearly demonstrating that FFN 511 selectively labels DA terminals (FIG. 36A). The two fluorophores do not display identical distributions, as GFP fills the axonal cytosol, while FFN 511 only labels synaptic vesicles, which are predominantly in presynaptic terminals. Thus, while FFN 511 is mostly colocalized with GFP, there are GFP labeled axonal spans that lack 511.

To further confirm that FFN 511 specifically labels DA terminals selective unilateral lesions of DA neurons were produced by in vivo injection of the selective dopaminergic neurotoxin 6-OHDA (6-hydroxydopamine) that results in a complete loss of evoked DA release) (37) and nearly completely abolished FFN 511 labeling in the injected hemisphere (FIG. 36C).

Multiple pharmacological agents were used to further examine probe 511 and its ability to report on presynaptic processes. Labeling by 511 was strongly inhibited by incubation with VMAT2 inhibitors reserpine and tetrabenazine (FIG. 36B) and the classic DA releaser amphetamine at pharmacologically relevant exposure (10 µM, 10 min) induced approximately a 50% loss of fluorescence, consistent with the drug's affect on evoked DA release (data not shown).

FFN 511 was destained by neuronal stimulation in a calcium-dependent manner under conditions identical to those that release DA as measured by simultaneous cyclic voltammetry. (FFN 511 is not oxidized and not measured by cyclic voltammetry). The stimulated destaining was completely dependent on the presence of calcium. Importantly, while the levels of FFN 511 sufficient to label the terminals did not alter evoked DA release as measured by cyclic voltammetry, higher concentrations reduced evoked DA release. The probe is thus sufficiently fluorescent to provide resolution of individual DA terminals at concentrations that do not interfere with normal catecholamine accumulation.

As FFN 511 was applied in a "pulse-chase" pattern, with the extracellular probe washed out following accumulation in the terminals, these experiments essentially measure the amount of DA remaining in the terminal and the released transmitter. The probability of release from a given terminal under a particular stimulus condition is simply the fractional destaining, i.e., $$P_{terminal} = F_t / (F_{t0} - F_{bkgnd})$$

$$P_{terminal} = 1 - (F_t - F_{bkg}) / (F_{t0} - F_{bkg}),$$

where $F_{t0}$ is the initial fluorescent intensity and $F_{bkgnd}$ is the label remaining after maximal stimulus is applied. $P_{terminal}$ approaches 0 in the absence of stimulation or with stimulation but in the absence of calcium, as expected. In the presence of calcium, at 4 Hz stimulation, it takes ~160 sec, i.e., 640 action potentials, to release about 50% of the terminal content with destaining well fit with a single exponential.

This parameter $P_{terminal}$ is similar but not identical to an estimate of the "readily releasable pool" and provides a direct means to estimate the fraction of synaptic vesicles that are released under different conditions: if vesicle fusion is all-or-none, i.e., if kiss-and-run fusion does not occur in these circumstances, the exponential decay of the signal indicates that ~0.1% of the synaptic vesicles that were competent to accumulate transmitter fused per stimulus.

These results were surprising in that prior electrochemical recordings of evoked DA release indicated that "refilling" the releasable pool following a single pulse stimulus requires ~1 minute, which would be consistent with a high release probability for each presynaptic terminal with substantial time before "stored vesicles" would become available for release. In contrast, the destaining data indicates, assuming that DA synaptic terminals generally contain fewer than 100 synaptic vesicles, that no more than 10% of the presynaptic terminals release a quantum of transmitter per stimulus.

In conclusion, the novel fluorescent false neurotransmitters disclosed herein are a class of imaging probes that enable the first means to optically measure several key presynaptic processes—including vesicular accumulation of a vesicle transporter substrate, transmitter redistribution, and release—with unprecedented spatial resolution. Probe FFW 511 was designed de novo and shown to selectively label DA terminals in the mouse CNS and LDCVs in chromaffin cells. Like dopamine, FFN 511 is taken up by synaptic vesicles in a manner dependent on VMAT and the pH gradient, and is released upon synaptic firing. Due to its high fluorescence, FFN 511 can be employed at low concentrations that do not interfere with DA release. Using FFN 511, we can directly measure the releasable pool of individual terminals, and thus enable detailed examination of mechanisms controlling this key parameter of synaptic plasticity. FFN 511 is also compatible with GFP-based tags and other optical tools, which will allow construction of fine resolution maps of synaptic microcircuitry. Furthermore, as vesicular transmitter uptake is energy dependent, FFN 511 will be able to indicate altered metabolic states and early degeneration of the presynaptic terminals. Because of the importance of dopamine in the brain function and its involvement in a number of neurological and psychiatric disorders, FFNs promise to contribute broadly neuroscience, neuropharmacology and disease diagnosis.

Therapeutic Applications

As well as the uses already disclosed herein, certain ring substituted compounds disclosed herein are thought to be dopamine receptor agonists. An advantage of the compounds is that unlike L-Dopa, the compounds do not oxidize and may be less toxic. In addition, unlike dopamine receptor agonists, they are accumulated in dopamine synaptic vesicles as they are VMAT substrates, and are thus released at the appropriate time and location, rather than acting everywhere and at all times in the brain. As such, these compounds are useful for the treatment of Parkinson's disease as dopamine replacements.

The compounds disclosed which are antagonists for dopamine or serotonin receptors are expected to be improved drugs for schizophrenia and affective disorders like depression. This is because current antipsychotics are mostly D2 antagonists, and also have no temporal or spatial selectivity. In contrast, the probes would be released from synaptic vesicles at the appropriate time and location as they are treated in the brain as dopamine or serotonin. Thus the probes disclosed here are both site-specific and activity-specific, and are therefore expected to have significantly less side-effects compared to, for example, L-dopa. Hypertension and blood pressure could be similarly treated (with the physiological effects arising in the hypothalamus and adrenal gland).

These properties are based on the observations that the compounds are VMAT substrates, unlike L-DOPA or any antipsychotic, antidepressant, or hypertensive agents. The compounds disclosed herein are useful to follow synaptic and vesicular release of neurotransmitters by fluorescence means. For example, terminal (or vesicular) destaining can be followed and measured using the probes. In addition, the efficacy of a therapy which acts on monoamine neurotransmitters may be followed and assayed using the probes as fluorescent false neurotransmitters.

Materials and Methods $^1$H and $^{13}$C NMR spectra were recorded on Bruker 300 Fourier transform NMR spectrometers. Spectra were recorded in CDCl$_3$ solutions referenced to solvent residual peak, unless otherwise indicated. Low Resolution Mass Spectra were obtained on a JOEL JMS-HX110 HF mass spectrometer. Flash chromatography was performed on SILI-CYCLE silica gel (230-400 mesh). All chemicals were purchased from Aldrich or Sigma and used as received. All reactions were monitored by Thin Layer Chromatography.

Photophysical Characterization

Ultraviolet spectra were measured on a Molecular Devices SPECTRAmax Plus 384 UV-Visible spectrophotometer operated through a Dell Pentium PC by SOFTmax software. All spectra were recorded in 100 mM sodium phosphate (pH 7.4) unless otherwise indicated. Recorded $\lambda_{max}$ is that of the longest wavelength transition. Extinction coefficients were reported as the average of at least three independent preparations of the probes. Fluorescence measurements were taken on a Jobin Yvon Fluorolog fluorescence spectrofluorometer in 100 mM sodium phosphate pH 7.4 at a concentration of 10 uM in probe, excited at their respective $\lambda_{max}$. See FIGS. 13-18 and 26-32.

Synthesis

Scheme 1.

Probe VB484

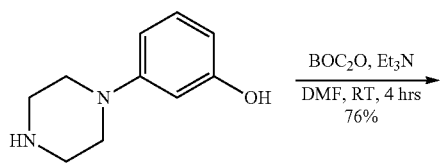

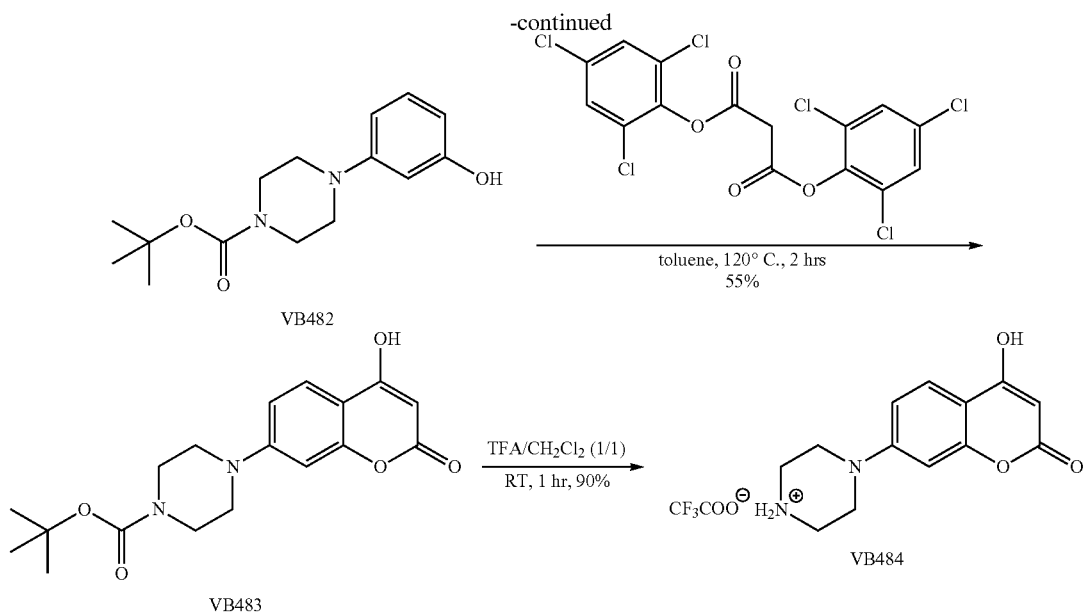

N-BOC-3-piperazin-1-yl-phenol (V9482)

BOC$_2$O (1.38 g, 6.3 mmol) and Et$_3$N (0.92 ml, 6.6 mmol) were subsequently added to a solution of 3-(1-piperazino)phenol (1.07 g, 6.0 mmol) in DMF (35 ml) and the resulting mixture was stirred at room temperature for 4 hrs. The mixture was diluted with EtOAc, washed with H$_2$O and the organic layer dried over Na$_2$SO$_4$. Solvent was removed in vacuo and the residue was purified by column chromatography on silica gel (eluent gradient: CH$_2$Cl$_2$-EtOAc 1:0 to 8:2) to afford pure VB482 (1.27 g, 76%).

NMR $^1$H (300 MHz, CDCl$_3$) δ ppm:

7.09 (t, 1H, J=8.1 Hz); 6-48 (dd, 1H, J1=8.2 Hz, J2=1.9 Hz); 6.39 (t, 1H, J=2.3 Hz); 6.33 (dd, 1H, J1=7.9 Hz, J2=2.3 Hz); 5.15 (8, 1H); 3.55 (t, 4H, J=5.2 Hz); 3.11 (t, 4H, J=5.2 Hz); 1.48 (s, 9H).

NMR $^{13}$C (75 MHz, CDCl$_3$) δ ppm:

157.0; 154.9; 152.6; 130.1; 108.8; 107.3; 103.6; 80.3; 49.1; 49.1; 28.4.

IR (NaCl, cm$^{-1}$) 3342; 2977; 2822; 1695; 1664; 1599; 1455; 1430; 1367; 1252; 1167; 1132; 997; 975; 760.

LRMS (APCI$^+$): 279 (C$_{15}$H$_{23}$N$_2$O$_3$, M+H).

N-BOC-4-hydroxy-7-piperazin-1-yl-coumarin (VB483)

A mixture of VB482 (835 mg, 3.0 mmol) and bis(2,4,6-trichlorophenyl) malonate (1389 mg, 3.0 mmol) in dry toluene (9 ml) was heated in a sealed tube at 120° C. for 2 hrs. The resulting suspension was cooled and filtered, the solids were washed with hot hexanes and dried in vacuo to give pure coumarin VB483 (568 mg, 55%).

NMR $^1$H (300 MHz, DMSO) δ ppm:

12.05 (s, 1H); 7.59 (d, 1H, J=8.9 Hz); 6.93 (dd, 1H, J1=8.9 Hz, J2=2.3 Hz); 6.76 (d, 1H, J=2.2 Hz); 5.33 (s, 1H); 3.45 (m, 4H); 3.32 (m, 4H); 1.43 (s, 9H).

NMR $^{13}$C (75 MHz, DMSO) δ ppm:

166.2; 162.6; 155.6; 153.8; 153.7; 123.9; 111.0; 106.2; 100.2; 87.5; 79.1; 46.6; 46.6; 28.0.

IR (NaCl, cm$^{-1}$) 2974; 1696; 1607; 1477; 1420; 1390; 1314; 1244; 1222; 1176; 996; 876.

LRMS (APCI$^+$): 347 (C$_{18}$H$_{23}$N$_2$O$_5$, M+H).

4-(4—Hydroxy-coumarin-7-yl)-piperazin-1-ium trifluoroacetate (VB484)

TFA (4.0 ml) was added to a solution of VB482 (200 mg, 0.58 mmol) in dry CH$_2$Cl$_2$ (8.00 ml) and the resulting mixture was stirred at room temperature for 1 hr. Solvent was removed in vacuo and the residue triturated with CH$_2$Cl$_2$. Precipitate was filtered off, powdered, washed with CH$_2$Cl$_2$ and dried in vacuo to provide pure VB484 (188 mg, 90%).

NMR $^1$H (300 MHz, DMSO) δ ppm:

12.28 (bs, 1H); 8.84 (bs, 2H); 7.63 (d, 1H, J=8.9 Hz); 6.98 (dd, 1H, J1=8.9 Hz, J2=2.3 Hz); 6.87 (d, 1H, J=2.2 Hz); 5.38 (s, 1H); 3.55 (m, 4H); 3.23 (bs, 4H).

NMR $^{13}$C (75 MHz, DMSO) δ ppm:

166.2; 162.6; 158.5 (q, JCP=34.3 Hz); 155.5; 152.9; 124.1; 116.3 (q, J$_{CF}$=294.7 Hz); 111.3; 107.1; 100.9; 87.9; 44.2; 42.3.

IR (NaCl, cm$^{-1}$) 2925; 2725; 1701; 1607; 1453; 1373; 1321; 1289; 1248; 1181; 1140.

LRMS (APCI$^+$): 247 (C$_{13}$H$_{15}$N$_2$O$_3$, M+H).

Scheme 2.

Probe VB505

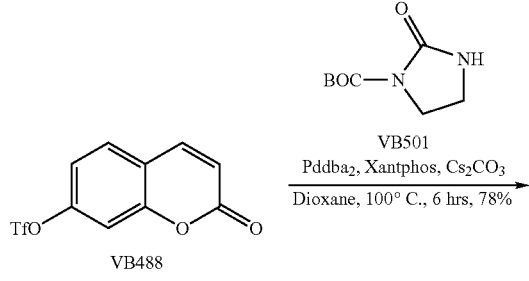

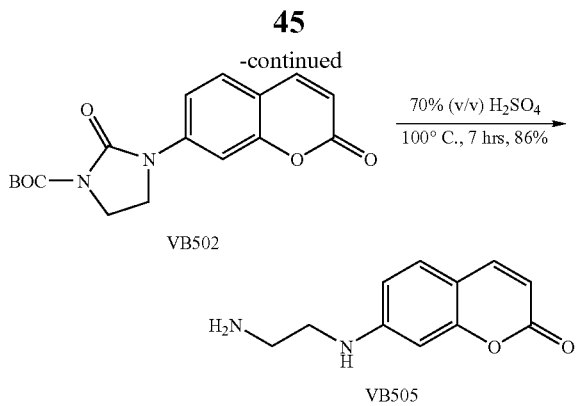

1-BOC-3-(coumarin-7-yl)-imidazolidin-2-one (VB502)

CB$_2$CO$_3$ (543 mg, 1.67 mmol) was dried in a Schlenk flask under vacuum at 150° C. for 5 hrs. The flask was charged with argon, cooled and triflate VB488 (23) (350 mg, 1.19 mmol), cyclic urea VB501 (24) (266 mg, 1.43 mmol), Pddba$_2$ (14 mg, 0.024 mmol), Xantphos (21 mg, 0.036 mmol) and toluene (12 ml) were added. The reaction mixture was then heated to 100° C. and stirred at this temperature for 24 hrs. The cooled mixture was diluted with CHCl$_3$ (300 ml:), washed with H$_2$O and the organic layer dried over Na$_2$SO$_4$. Solvent was removed in vacuo and the residue was purified by column chromatography on silica gel (eluent gradient: CH$_2$Cl$_2$-MeOH 1:0 to 99:1) to give VB502 (307 mg, 78%).

NMR $^1$H (300 MHz, CDCl$_3$) δ ppm:

7.83 (dd, 1H, J1=8.7 Hz, J2=2.1 Hz); 7.64 (d, 1H, J9.5 Hz); 7.44 (d, 1H, J=8.7 Hz); 7.31 (d, 1H, J=2.0 Hz); 6.32 (d, 1H, J=9.5 Hz); 3.91 (m, 4H); 1.57 (s, 9H).

NMR $^{13}$C (75 MHz, CDCl$_3$) δ ppm:

Not measured, because of the compound's low solubility.

IR (NaCl, cm$^{-1}$) 2975; 1768; 1711; 1696; 1612; 1365; 1313; 1298; 1228; 1059; 834.

HRMS (FAB): 331.1292 (C$_{17}$H$_{19}$N$_2$O$_5$, M+H; calc. 331.1294).

7-(2-Amino-ethylamino)-coumarin (VB505)

VB502 (158 mg, 0.48 mmol) was dissolved in 70% H$_2$SO$_4$ (5.0 ml) and heated at 100° C. until the hydrolysis was completed (7 hrs). The solution was diluted with H$_2$O (15 ml) and neutralized with solid NaHCO$_3$. Resulting mixture was extracted multiple times with CHCl$_3$, combined organic fractions were dried over Na$_2$SO$_4$ and solvent evaporated.

The crude product purified by column chromatography on silica gel (eluent gradient: CH$_2$Cl$_2$-MeOH 99:1 to 95:5) and recrystallized from CHCl$_3$-hexanes to afford VB505 (84 mg, 86%).

NMR $^1$H (300 MHz, MeOD) δ ppm:

7.74 (d, 1H, J=9.3 Hz); 7.31 (d, 1H, J=8.6 Hz); 6.62 (dd, 1H, J1=8.6 Hz, J2=2.2 Hz); 6.47 (d, 1H, J=2.1 Hz); 6.00 (d, 1H, J=9.3 Hz); 3.27 (t, 2H, J=6.3 Hz); 2.88 (t, 2H, J=6.3 Hz).

NMR $^{13}$C (75 MHz, MeOD) δ ppm:

164.6; 158.1; 154.4; 146.4; 130.2; 112.2; 110.5; 109.1; 97.9; 46.3; 41.3.

IR (NaCl, cm$^{-1}$) 3342; 2936; 1700; 1616; 1557; 1412; 1240; 1134; 822.

LRMS (APCI$^+$): 205 (C$_{11}$H$_{13}$N$_2$O$_2$, M+H).

Scheme 3.

Probe VB511

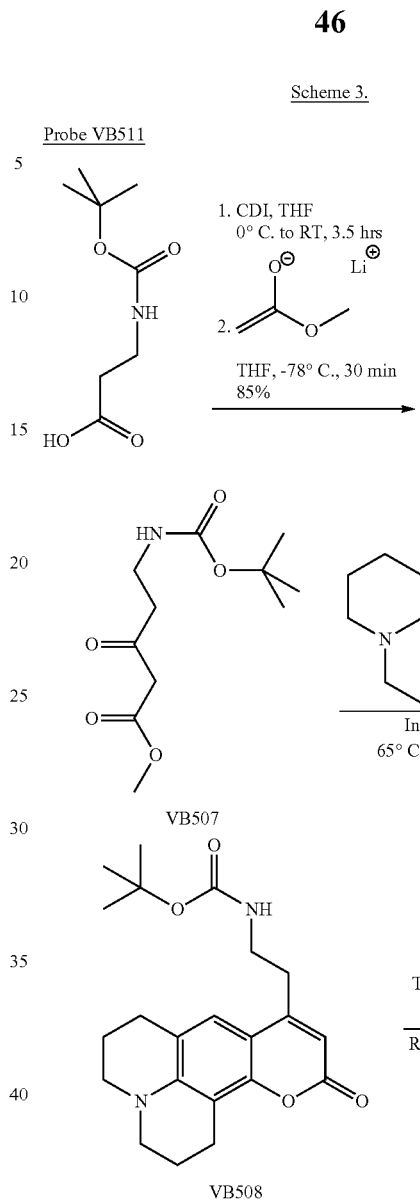

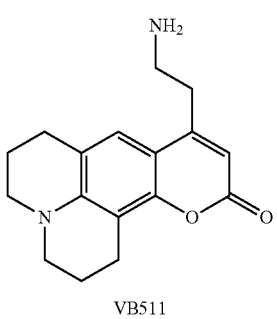

Methyl 5-tert-butoxycarbonylamino-3-oxo-pentanoate (VB507)

β-Ketoester VB507 was prepared by carbonyldiimidazole induced coupling of N-BOC-β-alanine and lithium enolate generated from methyl acetate (25). Spectral data were consistent with those previously published (26).

8-(2-tert-Butoxycarbonylamino-ethyl)-2,3,5,6-tetrahydro-1H,4H-11-oxa-3a-aza-benzo[de]anthracen-10-one (VB508)

A mixture of β-ketoester VB507 (60 mg, 0.25 mmol), 8-hydroxyjulolidine (47 mg, 0.25 mmol) and InCl$_3$ (5.4 mg, 0.025 mmol) was heated under argon at 65° C. for 24 hrs. Cooled mixture was dissolved in CHCl$_3$, washed with H$_2$O and dried over Na$_2$SO$_4$. Solvent was removed in vacuo and the residue was purified by column chromatography on silica gel (eluent gradient: CH$_2$Cl$_2$-EtOAc 1:0 to 9:1) to give VB508 (46 mg, 486).

NMR $^1$H (300 MHz, CDCl$_3$) δ ppm:
7.02 (s, 1H); 5.87 (s, 1H); 4.63 (bs, 1H); 3.42 (m, 2H); 3.25 (m, 4H); 2.87 (m, 4H); 2.77 (t, 2H, J=6.3 Hz); 1.97 (m, 4H), 1.44 (s, 9H).

NMR $^{13}$C (75 MHz, CDCl$_3$) δ ppm:
162.3; 155.7; 153.8; 151.4; 145.9; 121.5; 118.1; 107.8; 107.8; 106.9; 79.5; 49.9; 49.4; 39.7; 32.3; 28.4; 27.8; 21.5; 20.6; 20.4.

IR (NaCl, cm$^{-1}$) 3346; 2938; 2846; 1702; 1612; 1555; 1519; 1430; 1379; 1312; 1180.

LRMS (APCI$^+$) : 385 (C$_{22}$H$_{29}$N$_2$O$_4$, M+H).

8-(2-Amino-ethyl)-2,3,5,6-tetrahydro-1H,4H-11-oxa-3a-aza-benzo[de]anthracen-10-one (VB511)

TFA (0.75 ml) was added to a solution of VB508 (65 mg, 0.17 mmol) in dry CH$_2$Cl$_2$ (1.5 ml) and the resulting mixture was stirred at room temperature for 45 minutes.

The solvent was removed and saturated aqueous NaHCO$_3$ was added. Resulting mixture was extracted multiple times with CHCl$_3$, combined organic fractions were dried over Na$_2$SO$_4$ and solvent evaporated. The crude product purified by column chromatography on silica gel (eluent gradient: CH$_2$Cl$_2$-MeOH 99:1 to 95:5) and recrystallized from CHCl$_3$-hexanes to afford VB511 (48 mg, 92%).

NMR $^1$H (300 MHz, CDCl$_3$) δ ppm: 7.00 (s, 1H); 5.90 (s, 1H); 3.24 (m, 4H); 3.04 (m, 2H); 2.88 (t, 2H, J=6.5 Hz); 2.78 (m, 4H); 1.97 (m, 4H); 1.50 (bs, 2H).

NMR $^{13}$C (75 MHz, CDCl$_3$) δ ppm:
162.4; 154.1; 151.4; 145.8; 121.4; 118.0; 107.9; 107.7; 107.0; 49.9; 49.5; 41.2; 35.7; 27.7; 21.5; 20.6; 20.5.

IR (NaCl, cm$^{-1}$) 2939; 2845; 1702; 1612; 1553; 1519; 1428; 1378; 1312; 1182; 729.

LRMS (APCI$^+$): 285 (C$_{17}$H$_{21}$N$_2$O$_2$, M+H).

References

1. Sulzer, D.; Edwards, R. H. *Neuron.* 2005 Apr. 7; 46 (1) :1-2, "Antidepressants and the monoamine masquerade".

2. Henry, J. P.; Sagne, C.; Bedet, C. Gasnier, B. *Neurochem. Int* 1998, 32, 227-246, "The vesicular monoamine transporter: from chromaffin granule to brain".

3. Larsen, K. E.; Fon, E. A.; Hastings, T. G.; Edwards, R. H.; Sulzer, D. *J Neurosci.* 2002 Oct. 15; 22(20):8951-60, "Methamphetamine-induced degeneration of dopaminergic neurons involves autophagy and upregulation of dopamine synthesis".

4. Kahlig, K. M.; Galli, A. *Eur. J. Pharmacol.* 2003 Oct. 31; 479(1-3):153-8, "Regulation of dopamine transporter function and plasma membrane expression by dopamine, amphetamine, and cocaine".

5. Sulzer, D.; Rayport, S. *Neuron.* 1990, 5, 797-808. "Amphetamine and other psychostimulants reduce pH gradients in midbrain dopaminergic neurons and chromaffin granules: a mechanism of action".

6. Schwartz, J. W.; Blakely, R. D.; DeFelice, L. J. *J. Biol. Chem.* 2003 Mar. 14; 278(11):9768-77, "Binding and transport in norepinephrine transporters. Real-time, spatially resolved analysis in single cells using a fluorescent substrate".

7. Yee, D. J.; Balsanek, V.; Sames, D. *J. Am. Chem. Soc.* 2004 Mar. 3; 126(8):2282-3, "New tools for molecular imaging of redox metabolism: development of a fluorogenic probe for 3 alphahydroxysteroid dehydrogenases".

8. Tremblay, M. S.; Sames, D. *Org. Lett.* 2005 Jun. 9; 7(12):2417-20, "A new fluorogenic transformation: development of an optical probe for coenzyme Q".

9. Chen, G.; Yee, D. J.; Gubernator, N. G.; Sames, D. *J. Am. Chem. Soc.* 2005 Apr. 6; 127(13):4544, "Design of optical switches as metabolic indicators: new fluorogenic probes for monoamine oxidases (MAO A and B)".

10. Johnson, R. *Physiological Reviews.* 1988 January; 68(1): 232-307, "Accumulation of biological amines into chromaffin granules: a model for hormone and neurotransmitter transport".

11. Liu, Y.; Edwards, R. H. *Annu. Rev. Neurosci.* 1997; 20:125-56, "The role of vesicular transport proteins in synaptic transmission and neural degeneration".

12. Dorlars, A.; Schellhammer, C. W.; Schroeder, J: *Angew. Chem. Internat. Edit.*, 1975 665-679, "Heterocycles as structural units in new optical brighteners".

13. Henry, J. P.; Botton, D.; Sagne, C.; Isambert, M. F.; Desnos, C.; Blanchard, V.; Raisman-Vozari, R.; Krejci, E.; Massoulie, J.; Gasnier, B. *J Exp Biol.* 1994 November; 196: 251-62, "Biochemistry and molecular biology of the vesicular monoamine transporter from chromaffin granules".

14. Kalgutkar, A. S.; Dalvie, D. K.; Castagnoli, N., Jr.; Taylor, T. J. *Chem. Res. Toxicol.* 2001, 14, 1139-1162, "Interactions of nitrogen-containing xenobiotics with monoamine oxidase (MAO) isozymes A and B: SAR studies on MAO substrates and inhibitors"

15. Rothman, R. B.; Bauman, M. H.; *Eur. J. Pharmacol.* 2003, 479, 23-40, "Monoamine transporters and psychostimulant drugs".

16. Torres, G. E.; Gainetdinov, R. R.; Caron, M. G.; Nature Reviews Neuroscience, 2003, 4, 13-25, "Plasma membrane monoamine transporters: structure regulation and function".

17. Reinhard, J. F. Jr.; Diliberto, E. J. Jr.; Viveros, O. H.; Daniels, A. J., Subcellular compartmentalization of 1-methyl-4-phenylpyridinium with catecholamines in adrenal medullary chromaffin vesicles may explain the lack of toxicity to adrenal chromaffin cells. *Pron Natl Acad Sci USA.* 1987, 84, 8160-4.

18. Henry, J. P.; Sagne, C.; Bedet, C.; Gasnier, B., The vesicular monoamine transporter: from chromaffin granule to brain. *Neurochem. Int.* 1998, 32, 227-246.

19. Torres, G. E.; Gainetdinov, R. R.; Caron, M. G., Plasma membrane monoamine transporters: structure, regulation and function. *Nat. Rev. Neurosci.* 2003 January; 4(1) :13-25.

20. Volkow, N. D.; Fowler, J. S.; Wang, G. J. Logan, J.; Schlyer, D.; MacGregor, R.; Hitzemann, R.; Wolf, A. P., Decreased dopamine transporters with age in health human subjects. *Ann Neurol.* 1994, 36,237-9.

21. Steyer, J. A.; Horstmann, H.; Almers, W., Transport, docking and exocytosis of single secretory granules in live chromaffin cells. Nature, 1997, 388, 474-8.

22. Schwartz, J. W.; Novarino, G.; Piston, D. W.; DeFelice, L. J., Substrate binding stoichioetry and kinetics of the norepinephrine transporter. J Biol Chem., 2005, 280, 19177-84.

23. Cacchi, S.; Fabrizi, G.; Parisi, L. M. *Synthesis* 2004, 11, 1889-1894.

24. Patchett, A. A.; Rodan, G. A. *PCT Int. Appl.* 1998, 9846220.

25. Murakami, N.; Tamura, S.; Wang, W.; Takagi, T.; Kobayashi, M. *Tetrahedron* 2001, 57, 4323-4336.

26. Hashiguchi, S.; Kawada, A.; Natsugari, H. *Synthesis* 1992, 4, 403-408.

27. W. J. Betz, F. Mao, C. B. Smith, *Curr. Opinion Neurobiol.* 6, 365 (1996).

28. G. Miesenbock, D. A. De Angelis, J. E. Rothman, Nature 394, 192 (1998)

29. L. Tabares, E. Ales, M. Lindau, G. Alvarez de Toledo, J. Biol. Chem. 276, 39974 (2001).

30. B. G. Croft, G. D. Fortin, A. T. Corera, R. H. Edwards, A. Beaudet, L. E. Trudeau, E. A. Fon, Mol. Biol. Cell. 16, 306 (2005)

31. I. J. Kopin, Annu. Rev. Pharmacol. 8, 377 (1968)

32. J. P. Henry, C. Sagné, C. Bedet, B. Gasnier, Neurochem. Int. 32, 227, (1998)

33. J. S. Partilla, A. G. Dempsey, A. S. Nagpal, B. E. Blough, M. H. Baumann, R. B. Rothman, J. Pharmacol. Exp. Ther. 319, 237 (2006).

34. Y. Liu, D. Peter, A. Roghani, S. Schuldiner, G. G. Prive, D. Eisenberg, N. Brecha, R. H. Edwards, Cell, 70, 539 (1992).

35. D. Sulzer, S. Rayport, Neuron 5, 797 (1990).

36. K. Sawamoto, N. Nakao, K. Kobayashi, N. Matsushita, H. Takahashi, K. Kakishita, A. Yamamoto, T. Yoshizaki, T. Terashima, F. Murakami, T. Itakura, H. Okano, Proc. Natl. Acad. Sci. USA 98, 6423 (2001). 37. T. F. Oo, R. Siman, R. E. Burke, Exp. Neurol. 175 1 (2002).

38. Venton, B. J., Zhang, H., Garris, P. A., Phillips, P. E., Sulzer, D., and Wightman, R. M. (2003). Real-time decoding of dopamine concentration changes in the caudate-putamen during tonic and phasic firing. J Neurochem 87, 1284-1295.

39. Iversen, S. D., and Iversen, L. L. (2007). Dopamine: 50 years in perspective. Trends Neurosci 30, 188-193.

40. Sulzer, D., and Pothos, E. N. (2000). Presynaptic mechanisms that regulate quantal size. Reviews in the Neurosciences 11, 159-212.

What is claimed is:

1. A compound having the following structure:

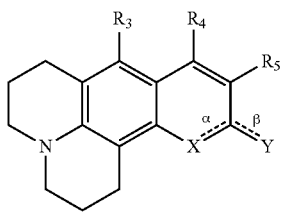

wherein

Y is O, X is O, bond α is absent and bond β is present;

$R_3$ is —H, —OH, alkyl, alkenyl, alkynyl, or halo, $R_4$ is —H, —$R_{11}N(R_{35})_2$, —$N(R_{35})R_{17}N(R_{35})_2$, —$R_{17}N(H)R_{18}$, —$R_{11}NR_{13}R_{14}$, —$N(R_{35})$ alkyl, or a piperazine group, wherein $R_{11}$ is a straight or a branched chain $C_2$-$C_6$ alkylene, $C_2$-$C_6$ alkenylene or $C_2$-$C_6$ alkynylene, and wherein the $(R_{35})_2$ group may be attached to any carbon atom of the $R_{11}$ group, wherein $R_{13}$ or $R_{14}$ or both are, independently, methyl or ethyl, wherein $R_{17}$ is a straight or a branched chain $C_2$-$C_6$ alkylene, $C_2$-$C_6$ alkenylene or $C_2$-$C_6$ alkynylene, wherein $R_{18}$ is a straight or a branched chain alkyl, alkenyl or alkynyl, where each occurrence of $R_{35}$ is, independently, —H, —$CH_3$ or —$C_2H_5$;

$R_5$ is —H, —$R_{12}N(R_{36})_2$, $R_{11}NR_{15}R_{16}$, —$N(R_{36})$ alkyl, —$N(R_{36})_2$, a piperazine group, a mono-substituted heterocyclyl or —$R_{19}W$, wherein $R_{12}$ is a straight or a branched chain $C_1$-$C_6$ alkylene, $C_1$-$C_6$ alkenylene or $C_1$-$C_6$ alkynylene, and wherein the $NH_2$ group may be attached to any carbon atom of the $R_{12}$ group, wherein $R_{15}$ or $R_{16}$ or both are, independently, methyl or ethyl, wherein $R_{19}$ is a straight or a branched chain $C_1$-$C_6$ alkylene, $C_1$-$C_6$ alkenylene or $C_1$-$C_6$ alkynylene, wherein W is a mono- or di-substituted heterocyclyl group or a mono-substituted heterocyclyl cation, where each occurrence of $R_{36}$ is, independently, —H, —$CH_3$ or —$C_2H_5$;

when one of $R_4$ or $R_5$ is —H, then the other of $R_4$ or $R_5$ is other than —H; and wherein the compound contains an $N(R_x)$ or $N(R_x)_2$ group wherein each occurrence of $R_x$ is, independently, —H, —$CH_3$ or —$C_2H_5$ or a salt of the compound.

2. The compound of claim 1, wherein $R_5$ is a mono-substituted heterocyclyl group wherein the heteroatom is nitrogen.

3. The compound of claim 1, wherein W is a mono-substituted heterocyclyl group wherein the heteroatom is nitrogen.

4. The compound of claim 1, wherein W is a di-substituted heterocyclyl group wherein the heteroatoms are each nitrogen.

5. The compound of claim 1, wherein W is a piperazine group.

6. The compound of claim 1 having the structure:

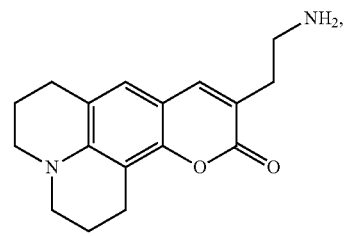

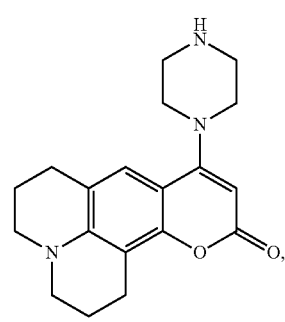

-continued

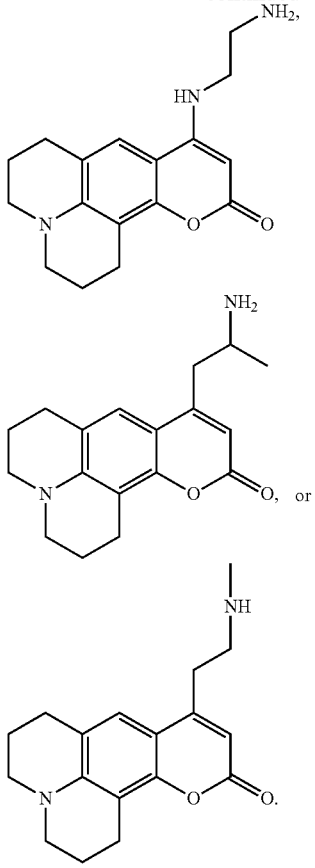

7. The compound of claim 1,
wherein
Y is O, X is O, bond α is absent and bond β is present;
$R_3$ is —H, —OH, alkyl, alkenyl, alkynyl, or halo,
$R_4$ is —H, or —$R_{11}NH_2$,
  wherein $R_{11}$ is a straight or a branched chain $C_2$-$C_6$ alkylene, $C_2$-$C_6$ alkenylene or $C_2$-$C_6$ alkynylene, and
  wherein the $NH_2$ group may be attached to any carbon atom of the $R_{11}$ group;
$R_5$ is —H, or —$R_{12}NH_2$,
  wherein $R_{12}$ is a straight or a branched chain $C_1$-$C_6$ alkylene, $C_2$-$C_6$ alkenylene or $C_2$-$C_6$ alkynylene, and
  wherein the $NH_2$ group may be attached to any carbon atom of the $R_{12}$ group; and
wherein the compound contains an $NH_2$ group.

8. The compound of claim 1, having the structure:

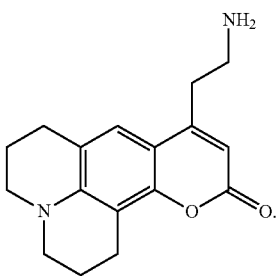

* * * * *